(12) United States Patent
Colamonici et al.

(10) Patent No.: US 7,662,924 B2
(45) Date of Patent: Feb. 16, 2010

(54) BETA CHAIN-ASSOCIATED REGULATOR OF APOPTOSIS

(75) Inventors: Oscar Colamonici, Chicago, IL (US); Shahid Siddiqui, Wilmette, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/267,986

(22) Filed: Nov. 7, 2005

(65) Prior Publication Data

US 2006/0121505 A1    Jun. 8, 2006

Related U.S. Application Data

(63) Continuation-in-part of application No. 10/373,228, filed on Feb. 24, 2003, now abandoned.

(60) Provisional application No. 60/359,144, filed on Feb. 22, 2002, provisional application No. 60/625,745, filed on Nov. 5, 2004.

(51) Int. Cl.
    C07K 17/00    (2006.01)
    G01N 33/53    (2006.01)

(52) U.S. Cl. .................... 530/387.1; 435/7.1

(58) Field of Classification Search ............... 530/387.1
    See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,376,110 A | 3/1983 | David et al. |
| 4,816,567 A | 3/1989 | Cabilly et al. |
| 4,892,538 A | 1/1990 | Aebischer et al. |
| 4,945,050 A | 7/1990 | Sanford et al. |
| 4,970,154 A | 11/1990 | Chang |
| 5,011,472 A | 4/1991 | Aebischer et al. |
| 5,106,627 A | 4/1992 | Aebischer et al. |
| 5,234,784 A | 8/1993 | Aslam et al. |
| 5,252,714 A | 10/1993 | Harris et al. |
| 5,272,071 A | 12/1993 | Chappel |
| 5,364,791 A | 11/1994 | Vegeto et al. |
| 5,399,346 A | 3/1995 | Anderson et al. |
| 5,464,758 A | 11/1995 | Gossen et al. |
| 5,489,743 A | 2/1996 | Robinson et al. |
| 5,514,578 A | 5/1996 | Hogness et al. |
| 5,545,807 A | 8/1996 | Surani et al. |
| 5,557,032 A | 9/1996 | Mak |
| 5,585,089 A | 12/1996 | Queen et al. |
| 5,593,875 A | 1/1997 | Wurm et al. |
| 5,631,236 A | 5/1997 | Woo et al. |
| 5,635,399 A | 6/1997 | Krieger et al. |
| 5,650,298 A | 7/1997 | Bujard et al. |
| 5,654,168 A | 8/1997 | Bujard et al. |
| 5,672,344 A | 9/1997 | Kelly et al. |
| 5,672,510 A | 9/1997 | Eglitis et al. |
| 5,676,954 A | 10/1997 | Brigham |
| 5,679,559 A | 10/1997 | Kim et al. |
| 5,693,762 A | 12/1997 | Queen et al. |
| 5,723,323 A | 3/1998 | Kauffman et al. |
| 5,741,679 A | 4/1998 | George et al. |
| 5,763,192 A | 6/1998 | Kauffman et al. |
| 5,814,476 A | 9/1998 | Kauffman et al. |
| 5,817,483 A | 10/1998 | Kauffman et al. |
| 5,824,469 A | 10/1998 | Horwitz et al. |
| 5,834,186 A | 11/1998 | George et al. |
| 6,783,961 B1 * | 8/2004 | Edwards et al. ............ 435/91.1 |

FOREIGN PATENT DOCUMENTS

| | | |
|---|---|---|
| EP | 0036676 | 4/1981 |
| EP | 0133988 | 3/1985 |
| EP | 0154316 | 9/1985 |
| EP | 0088046 | 10/1986 |
| EP | 0143949 | 10/1986 |
| EP | 0058481 | 8/1988 |
| EP | 0401384 | 12/1990 |
| EP | 0505500 | 7/1991 |
| EP | 0546073 | 5/1994 |
| WO | WO 90/04036 | 4/1990 |
| WO | WO 91/09955 | 7/1991 |

(Continued)

OTHER PUBLICATIONS

Stephens et al (Immunology, Aug. 1995, 85:668-674).*
Yang et al (Mar. 15, 1999, Cancer Research, 56:1236-1243).*
U.S. Appl. No. 10/373,228, filed Feb. 24, 2003, Coamonici O et al.
Adames et al., 1985, Nature 318:533-38.
Adams et al., 1995, Sem. Cancer Biol 6:99.
Aebischer et al., 1991, Exper. Neurol. 111:269-75.
Alexander et al., 1987, Mol. Cell. Biol., 7:1436-44.
Altschul et al., 1990, J. Mol. Biol. 215:403-10.
Anderson et al., Nucleic Acid Hybridisation: A Practical Approach Ch. 4 (IRL Press Limited).
Aridor et al., 2000, Science 287:816-17.
Bates et al., 1998. Nature 395:124.

(Continued)

Primary Examiner—Sean E Aeder
(74) Attorney, Agent, or Firm—McDonnell Boehnen Hulbert & Berghoff LLP

(57) ABSTRACT

The present invention provides β-subunit-Associated Regulator of Apoptosis, or BARA, polypeptides and nucleic acid molecules encoding the same. The invention also provides selective binding agents, vectors, host cells, non-human transgenic animals, devices and methods for producing BARA polypeptides. The invention further provides compositions comprising BARA nucleic acids, polypeptides, and fusions or derivatives thereof. The invention further provides methods for treating, preventing, or ameliorating a medical disease, condition, or disorder comprising administering BARA or BARA compositions, as well as methods of diagnosing a pathological condition related to BARA. Still further, the invention provides methods of modulating levels of BARA expression and methods of determining whether a compound stimulates or inhibits BARA polypeptide activity or BARA polypeptide production.

8 Claims, 18 Drawing Sheets

FOREIGN PATENT DOCUMENTS

| | | |
|---|---|---|
| WO | WO 91/10425 | 7/1991 |
| WO | WO 91/10470 | 7/1991 |
| WO | WO 91/10741 | 7/1991 |
| WO | WO 93/03162 | 2/1993 |
| WO | WO 93/15722 | 8/1993 |
| WO | WO 94/02602 | 2/1994 |
| WO | WO 94/20069 | 9/1994 |
| WO | WO 94/28122 | 12/1994 |
| WO | WO 95/05452 | 2/1995 |
| WO | WO 95/34670 | 12/1995 |
| WO | WO 96/33735 | 10/1996 |
| WO | WO 96/37609 | 11/1996 |
| WO | WO 96/40911 | 12/1996 |
| WO | WO 96/40958 | 12/1996 |
| WO | WO 96/41865 | 12/1996 |
| WO | WO 97/10337 | 3/1997 |
| WO | WO 97/31898 | 9/1997 |
| WO | WO 97/31899 | 9/1997 |
| WO | WO 97/38117 | 10/1997 |
| WO | WO 99/10494 | 3/1999 |
| WO | WO 99/15650 | 4/1999 |
| WO | WO 99/25044 | 5/1999 |
| WO | WO 01/53455 | 7/2001 |

OTHER PUBLICATIONS

Baubonis and Sauer, 1993, Nucleic Acids Res. 21:2025-29.
Bayer et al., 1990, Meth. Enz. 184:138-63.
Bernoist and Chambon, 1981, Nature 290:304-10.
Bowie et al., 1991, Science, 253:164-70.
Boxen et al., 2002, Current Biol. 12:906-911.
Brenner et al., 1997, Curr, Opin. Struct. Biol. 7:369-76.
Brinster et al., 1982, Nature 296:39-42.
Brodeur et al., Monoclonal Antibody Production Techniques and Applications 51-63 (Marcel Dekker, Inc., 1987).
Bromberg et al., 1996, Proc. Natl. Acad. Sci. USA, 93:7673.
Bruggermann et al., 1993, Year in Immuno. 7:33.
Capon et al., 1989, Nature 337:525-31.
Carillo et al., 1988, SIAM J. Applied Math., 48:1073.
Carnero et al., 2000, Nat. Cell Biol. 2:148-55.
Chou et al., 1974, Biochemistry 13:211-222.
Chou et al., 1974, Biochemistry 13:222-45.
Chou et al., 1978, Adv. Enzymol. Relat. Areas Mol. Biol. 47:45-48.
Chou et al., 1978, Ann. Rev. Biochem. 47:251-276.
Chou et al., 1979, Biophys. J. 26:367-84.
Chu et al., 1981, Gene 13:197.
Darnell et al., 1994, Science 264:1415.
Davis et al., Basic Methods in Molecular Biology (Elsevier, 1986).
Dayhoff et al., (5) Atlas of Protein Sequence and Structure (Supp. 3, 1978).
DeBoer et al., 1983, Proc. Natl. Acad. Sci. U.S.A., 80:21-25.
Devereux et al., 1984, Nucleic Acids Res. 12:387.
DiCiommo et al., 2000, Sem. Cancer Biol. 10:255.
Doetschman et al., 1987, Nature 330:576-78.
Doetschman et al., 1988, Proc. Natl. Acad. Sci. U.S.A. 85:8583-87.
Engels et al., 1989, Angew. Chem. Intl. Ed. 28:716-34.
Eppstein et al., 1985, Proc. Natl. Acad. Sci. USA 82:3688-92.
Fawell et al., 1994, Proc. Natl. Acad. Sci. U.S.A. 91:664-68.
Graham et al., 1973, Virology 52:456.
Gribskov et al., 1987, Proc. Nat. Acad. Sci. U.S.A. 84:4355-58.
Gribskov et al., 1990, Methods Enzymol. 183:146-59.
Grosschedl et al., 1984, Cell 38:647-58.
Hammer et al., 1987, Science 235:53-58.
Hanahan, 1985, Nature 315:115-22.
Hefti 1994, Neurobiology 25:1418-35.
Henikoff et al., 1992, Proc. Natl. Acad. Sci USA 89:10915-19.
Holm et al., 1999, Nucleic Acids Res. 27:244-247.
Hoogenboom et al., 1991, J. Mol. Biol. 227:381.

Houghten et al., 1985, Proc Natl Acad. Sci. USA 82:5132.
Hsieh et al., 1999, Mol. Cell 3:181.
Ihle et al., 1994, TIBS, 19:222.
Jakobovits et al., 1993, Nature 362:255-58.
Jakobovits et al., 1993, Proc. Natl. Acad. Sci. 90:2551-55.
Jones et al., 1986, Nature 321:522-25.
Jones, 1997, Curr. Opin. Struct. Biol. 7:377-87.
Kelsey et al., 1987, Genes and Devel. 1:161-71.
Kitts et al., 1993, Biotechniques, 14:810-17.
Kohler et al., 1975, Nature 256:495-97.
Kollias et al., 1986, Cell 46:89-94.
Kozbor, 1984, J. Immunol. 133:3001.
Krumlauf et al., 1985, Mol. Cell. Biol., 5:1639-48.
Kucherlapati, 1989, Prog. in Nucl. Acid Res. & Mol. Biol. 36:301.
Kyte et al., 1982, J. Mol. Biol. 157:105-31.
Langer et al., 1981, J. Biomed. Mater. Res. 15:267-277.
Langer, 1982, Chem. Tech. 12:98-105.
Leder et al., 1986, Cell 45:485-95.
Leonard et al., 1998, Annu. Rev. Immunol. 16:293.
Lozano and Hulboy, 1995, Methods (San Diego) 8: 215-224.
Lucklow et al., 1993, J. Virol., 67:4566-79.
Lucklow, 1993, Curr. Opin. Biotechnol. 4:564-72.
MacDonald, 1987, Hepatology 7:425-515.
Magram et al., 1985, Nature 315:338-40.
Marks et al., 1991, J. Mol. Biol. 222:581.
Marston et al., 1990, Meth. Enz., 182:264-75.
Mason et al., 1986, Science 234:1372-78.
Merrifield et al., 1963, J. Am. Chem. Soc. 85:2149.
Morrison et al., 1985, Proc. Natl. Acad. Sci. 81:6851-55.
Moult, 1996, Curr. Opin. Biotechnol. 7:422-27.
Nagahara et al., 1998, Nat. Med. 4:1449-52.
O'Gorman et al., 1991, Science 251:1351-55.
Ornitz et al., 1986, Cold Spring Harbor Symp. Quant. Biol. 50:399-409.
Pinkert et al., 1987, Genes and Devel. 1:268-76.
Prendergast, 1999, Oncogene 18:2967.
Qin et al., 1994, Proc Natl Acad Sci USA 91:10918.
Readhead et al., 1987, Cell 48:703-12.
Riechmann et al., 1998, Nature 332:323-27.
Rivera et al., 2000, Science 287:826-30.
Roberts et al., 1997, Proc. Natl. Acad. Sci. U.S.A. 94:12297-303.
Roberts, 1999, Curr. Opin. Chem. Biol. 3:268-73.
Rubinstein et al., 1998, Cytokine Growth Factor Rev, 9:175.
Sauer, 1993, Methods Enzymol., 225:890-900.
Sauer, 1994, Curr. Opin. Biotechnol., 5:521-27.
Schwarze et al., 1999, Science 285:1569-72.
Sellers et al., 1997, J Clin Oncol 15:3301.
Shani, 1985, Nature 314:283-86.
Sherr et al., 2000, Current Opinion Gen. Develop. 10:94.
Sherr, 1996, Science 274:1672.
Sidman et al., 1983, Biopolymers 22:547-56.
Sippl et al., 1996, Structure 4:15-19.
Straus, 1999, Science 285:1466-67.
Swift et al., 1984, Cell 38:639-46.
Thomas and Capecchi, 1987, Cell 51:503-12.
Thomas et al., 1986, Cell 44:419-28.
Tresco et al., 1992, ASAIO 38:17-23.
Urlaub et al., 1980, Proc. Natl. Acad. Sci. 97:4216-20.
Verhoeyen et al., 1988, Science 239:1534-36.
Vidal et al., 2000, Gene 247:1.
Villa-Kamaroff et al., 1978, Proc. Natl. Acad. Sci. U.S.A., 75:3727-31.
Wagner et al., 1981, Proc. Natl. Acad. Sci. U.S.A. 78:1444-45.
Winn et al., 1991, Exper. Neurol. 113:322-29.
Yamamoto et al., 1980, Cell 22:787-97.
Zola, Monoclonal Antibodies: A Manual of Techniques 147-158 (CRC Press, Inc., 1987).
Zuo et al., 2002, Genes Develop. 16:2923-2934.

* cited by examiner

Figure 7

BETA CHAIN-ASSOCIATED REGULATOR OF APOPTOSIS

This application is a continuation-in-part of U.S. patent application Ser. No. 10/373,228, filed Feb. 24, 2003, now abandoned which claims the benefit of U.S. Provisional Patent Application No. 60/359,144, filed Feb. 22, 2002, the entirety of which is hereby incorporated by reference. This application also claims the benefit of U.S. Provisional Patent Application No. 60/625,745, filed Nov. 5, 2004, the entirety of which is hereby incorporated by reference. This invention was made with government support under GM054709 awarded by the National Institutes of Health. The government has certain rights in the invention.

BACKGROUND OF THE INVENTION

1. Field of the Invention

This invention relates to β-subunit-Associated Regulator of Apoptosis, or BARA, polypeptides and nucleic acid molecules encoding the same. The invention also relates to selective binding agents, vectors, host cells, non-human transgenic animals, devices and methods for producing BARA polypeptides. The invention further relates to compositions comprising BARA nucleic acids, polypeptides, and fusions or derivatives thereof. The invention further relates to methods for treating, preventing, or ameliorating a disease, condition, or disorder comprising administering BARA or BARA compositions, as well as methods of diagnosing a pathological condition related to BARA. Still further, the invention relates to methods of modulating levels of BARA expression and methods of determining whether a compound stimulates or inhibits BARA polypeptide activity, BARA gene expression or BARA polypeptide production.

2. Background of the Related Art

The causes of benign and malignant neoplasms are complex and poorly understood. Cellular DNA can be altered or damaged in response to internal or external stimuli, which alteration or damage then acts as neoplastic perturbations in gene expression, resulting in disruption of otherwise normal cell division and proliferation. Such disruption, when resulting in unfettered cell proliferation (defined as the increase in number of cells resulting from completion of the cell cycle), can cause cancer.

Neoplasms manifest when the normal progression of and orderly relationship between cell division and cell differentiation malfunctions. Usually, cell proliferation is restricted to non-differentiated stem cells, which ordinarily differentiate and reproduce to provide a replacement for aged dying cells. In neoplasia, any cell can become uncoupled from the normal control mechanisms. The result is uncontrolled growth.

Extracellular or intracellular factors can determine whether a quiescent cell will begin to proliferate and also whether a normal proliferating cell in the G1 phase of the cell cycle will begin to cycle or will revert to quiescence. In benign and malignant neoplasms, control of proliferation is lost. Exemplary carcinogenic factors of external origin that act inside the cell include physical carcinogens such as ionizing or ultraviolet radiation and foreign substances such as cigarette smoke and asbestos. Carcinogenic substances include various chemicals, natural or man-made, which can alter or damage cellular DNA, directly or indirectly, to elicit an oncogenic event. Exemplary internal carcinogens can be biological substances such as bacteria, viruses, parasites, hormones and cytokines.

Although most mammalian tissues and organs are capable of giving rise to neoplasms, the fundamental processes resulting in tumors of diverse origins appear to be quite similar. Normal cells proliferate or reproduce in rigorous compliance with programmed guidance from parental or adjacent cells. Such unceasing, disciplined instruction ensures that each tissue maintains a size, architecture and function appropriate to the body's needs.

Neoplastic cells, in distinct contrast, become unresponsive to the usual controls of parental or adjacent cells with respect to proliferation, architecture and/or function. These neoplastic cells frequently (i) migrate from the site where they began, (ii) invade nearby tissues, and (iii) travel through the blood and lymphatic circulatory systems to form metastatic lesions at distant sites in the body. These lesions become lethal when they disrupt the normal function of other tissues or organs essential for the patient survival.

Normally, the body's tissues prevent excessive proliferation of cells by depriving them of excessive amounts of growth-stimulating factors, or by flooding the cells with antiproliferative factors derived from adjacent or parental cells which block the actions of the growth stimulating factors. However, certain cellular proteins, through their intrinsic ability to regulate a host of other genes involved in the control of cell proliferation, can reorganize and redirect a cell's normal or abnormal fate. Thus, the loss of these growth-controlling genes by deletion or mutation is a common occurrence in neoplasias (Lozano and Hulboy, 1995, Methods (San Diego) 8: 215-224.)

The majority of chemotherapeutic anti-neoplasia agents in current clinical practice disrupt major intracellular systems such as DNA synthesis and essential enzymes systems. They are toxic compounds and exert their greatest anti-neoplasia effect when employed at the maximum tolerated dose. Using these chemotherapeutic agents, toxic actions to normal tissue can greatly limit the amount that can be safely administered. To date, the most commonly utilized agents are only partially selective in their toxicity. Thus, they are damaging to both normal and neoplastic cells. Nevertheless treatment of neoplastic disease is predicated on exploiting the small differences between healthy normal cells and neoplastic cells.

There is thus a need in the art to provide anti-neoplastic and chemotherapeutic agents that are more selective and specific for tumor cells and less toxic to normal cells for treating neoplasia.

SUMMARY OF THE INVENTION

This invention provides reagents and methods for identifying and characterizing compounds that decrease cellular, particularly neoplastic cell proliferation, by, inter alia, inducing apoptosis, senescence or both. The invention further provides methods for treating, preventing, or ameliorating a medical disease, condition, or disorder associated with abnormal or pathological cellular proliferative conditions, including for example benign and malignant cancerous growths. In particular, the invention provides a selective binding agents or fragment thereof that specifically binds a polypeptide of the invention, including immunological reagents having antigenic specificity for a polypeptide encoded by all or a portion of a nucleic acid as disclosed herein.

In a first aspect, the invention provides isolated nucleic acid molecules encoding the polypeptide as set forth in SEQ ID NO: 4, SEQ ID NO: 5, SEQ ID NO: 6, or SEQ ID NO: 10. In particular embodiments, the invention provides isolated nucleic acids comprising a nucleotide sequence as set forth in SEQ ID NO: 1, SEQ ID NO: 2, SEQ ID NO: 3, or SEQ ID NO: 9. Generally, the invention provides nucleic acids that hybridize under at least moderately stringent conditions, and more preferably high stringency conditions, to the complement of the nucleotide sequence of either (a) or (b), wherein the nucleic acid molecule encodes a polypeptide having an antigenic, biological or enzymatic activity of the polypeptide set forth in SEQ ID NO: 4, SEQ ID NO: 5, SEQ ID NO: 6, or SEQ ID NO: 10. Thus, the invention also provides nucleic acids complementary to the nucleotide sequence of any of the preceding embodiments.

In additional embodiments of this aspect, the invention provides isolated nucleic acid molecules comprising a nucleotide sequence encoding a polypeptide that is at least about 70 percent identical to the polypeptide as set forth in SEQ ID NO: 4, SEQ ID NO: 5, SEQ ID NO: 6, or SEQ ID NO: 10, wherein the encoded polypeptide has an antigenic, biological or enzymatic activity of the polypeptide set forth in SEQ ID NO: 4, SEQ ID NO: 5, SEQ ID NO: 6, or SEQ ID NO: 10. In yet further additional embodiments, the invention provides nucleic acids comprising a nucleotide sequence encoding an allelic variant or splice variant of a polypeptide set forth in SEQ ID NO: 4, SEQ ID NO: 5, SEQ ID NO: 6, or SEQ ID NO: 10, or of a nucleotide sequence as set forth in SEQ ID NO: 1, SEQ ID NO: 2, SEQ ID NO: 3, or SEQ ID NO: 9. In other embodiments, the invention provides nucleic acids comprising a less than full length portion or polypeptide motif-encoding region of a nucleic acid encoding a polypeptide set forth in SEQ ID NO: 4, SEQ ID NO: 5, SEQ ID NO: 6, or SEQ ID NO: 10, more particularly a nucleotide sequence as set forth in SEQ ID NO: 1, SEQ ID NO: 2, SEQ ID NO: 3, or SEQ ID NO: 9, wherein the portion or region encodes a polypeptide fragment of at least about 50 amino acid residues, and wherein the polypeptide fragment has an antigenic, biological or enzymatic activity of the polypeptide set forth in SEQ ID NO: 4, SEQ ID NO: 5, SEQ ID NO: 6, or SEQ ID NO: 10, or is antigenic. Alternatively, the nucleic acid comprises a region of the nucleotide sequence of SEQ ID NO: 1, SEQ ID NO: 2, SEQ ID NO: 3, or SEQ ID NO: 9 or the nucleotide sequence of any of the aforesaid embodiments comprising a fragment of at least about 30 nucleotides. Other embodiments comprise nucleic acids that hybridize under at least moderately stringent conditions to the complement of the nucleotide sequence of any of the embodiments of the invention set forth herein, wherein the nucleic acid molecule encodes a polypeptide having an antigenic, biological or enzymatic activity of the polypeptide set forth in SEQ ID NO: 4, SEQ ID NO: 5, SEQ ID NO: 6, or SEQ ID NO: 10. Nucleic acid comprising a nucleotide sequence complementary to the nucleotide sequence of any of the embodiments of the invention set forth herein are also provided.

The invention further provides an isolated nucleic acid molecule comprising a nucleotide sequence encoding a polypeptide as set forth in SEQ ID NO: 4, SEQ ID NO: 5, SEQ ID NO: 6, or SEQ ID NO: 10 with at least one conservative amino acid substitution, amino acid insertion, amino acid deletion, or C- and/or N-terminal truncation, wherein the encoded polypeptide has an antigenic, biological or enzymatic activity of the polypeptide set forth in SEQ ID NO: 4, SEQ ID NO: 5, SEQ ID NO: 6, or SEQ ID NO: 10. The invention also provides such embodiments of the nucleic acids disclosed herein comprising a fragment of at least about 30 nucleotides. Nucleic acid molecules attached to a solid support are also provided, as is an array of nucleic acid molecules comprising at least one nucleic acid molecule of the invention. Further provided are nucleic acids of any such embodiments that hybridize under at least moderately stringent conditions to the complement of the nucleotide sequence of any of these embodiments of the nucleic acid disclosed herein, wherein the nucleic acid molecule encodes a polypeptide having an activity of the polypeptide set forth in SEQ ID NO: 4, SEQ ID NO: 5, SEQ ID NO: 6, or SEQ ID NO: 10. Nucleic acids complementary to the nucleotide sequence of any of these embodiments of the nucleic acid disclosed herein are also provided.

The invention further provides vectors comprising and operably linked to any of the nucleic acid molecules disclosed herein, as well as host cells comprising the vector. Suitable host cells of the invention can be eukaryotic cells or prokaryotic cells. Preferably, the vectors of the invention comprise sequences operably linked to a nucleic acid molecule of the invention and effective for expressing the nucleic acid in a host cell.

The invention further provides a method for producing a BARA polypeptide comprising culturing host cells comprising a nucleic acid embodiment of the invention, most preferably further comprising a vector operably linked to said nucleic acid embodiment, above under suitable conditions to express the polypeptide. In the practice of the methods of the invention for producing a BARA polypeptide, the methods advantageously further include the step of isolating the polypeptide from the culture. Accordingly, the invention further provides isolated BARA polypeptides encoded by the nucleic acid embodiments and produced according the methods of the invention.

The invention also provides methods for identifying and characterizing compounds that inhibit BARA polypeptide activity, BARA gene expression or BARA polypeptide production comprising the step of incubating or culturing a host cell of the invention in the presence and absence of the compound and comparing BARA polypeptide activity or BARA polypeptide production in the host cell in the presence and absence of the compound.

In a second aspect, the invention further provides isolated polypeptides comprising the amino acid sequence as set forth in SEQ ID NO: 4, SEQ ID NO: 5, SEQ ID NO: 6, or SEQ ID NO: 10. In addition, the invention provides isolated polypeptides comprising an amino acid sequence that is at least about 70 percent identical to the amino acid sequence of SEQ ID NO: 4, SEQ ID NO: 5, SEQ ID NO: 6, or SEQ ID NO: 10, wherein the polypeptide has an antigenic, biological or enzymatic activity of the polypeptide set forth in SEQ ID NO: 4, SEQ ID NO: 5, SEQ ID NO: 6, or SEQ ID NO: 10. The invention further provides less than full length fragments of the amino acid sequence set forth in SEQ ID NO: 4, SEQ ID NO: 5, SEQ ID NO: 6, or SEQ ID NO: 10 comprising at least about 30 amino acid residues, wherein the fragment has an antigenic, biological or enzymatic activity of the polypeptide set forth in SEQ ID NO: 4, SEQ ID NO: 5, SEQ ID NO: 6, or SEQ ID NO: 10, or is antigenic. In further embodiments, the invention provides polypeptides comprising an amino acid sequence of an allelic variant or splice variant of the amino acid sequence as set forth in SEQ ID NO: 4, SEQ ID NO: 5, SEQ ID NO: 6, or SEQ ID NO: 10, having an antigenic, biological or enzymatic activity of the polypeptide set forth in SEQ ID NO: 4, SEQ ID NO: 5, SEQ ID NO: 6, or SEQ ID NO: 10.

In additional embodiments of this aspect, the invention provides an isolated polypeptide comprising an amino acid sequence as set forth in SEQ ID NO: 4, SEQ ID NO: 5, SEQ ID NO: 6, or SEQ ID NO: 10 with at least one conservative amino acid substitution; or with at least one amino acid insertion; or with at least one amino acid deletion; or that has a C- and/or N-terminal truncation; or with at least one modification that is an amino acid substitution, amino acid insertion, amino acid deletion, C-terminal truncation, or N-terminal truncation, wherein the polypeptide has an activity of the polypeptide set forth in SEQ ID NO: 4, SEQ ID NO: 5, SEQ ID NO: 6, or SEQ ID NO: 10. Also, the invention provides an isolated polypeptide encoded by the nucleic acid molecules recited above, wherein the polypeptide has an activity of the polypeptide set forth in SEQ ID NO: 4, SEQ ID NO: 5, SEQ ID NO: 6, or SEQ ID NO: 10. Further, the invention provides polypeptide derivatives of the polypeptide embodiments of the invention disclosed herein, wherein the derivative comprises a modification that can be a covalent modification with a water-soluble polymer such as polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

The invention further provides fusion polypeptides comprising a polypeptide of the invention fused to a heterologous amino acid sequence. In preferred embodiments, the heterologous amino acid sequence of the fusion polypeptide can be an IgG constant domain or fragment thereof.

In a third embodiment, the invention provides a selective binding agent or fragment thereof that specifically binds a polypeptide of the invention. A selective binding agent or fragment thereof may specifically bind a polypeptide comprising the amino acid sequence as set forth in SEQ ID NO: 4, SEQ ID NO: 5, SEQ ID NO: 6, or SEQ ID NO: 10, or a fragment thereof. The selective binding agent can be polyclonal antisera or more preferably monoclonal antibodies or fragments thereof. Particular embodiments of this aspect of the invention include human or humanized antibodies or fragment thereof; polyclonal antibodies or fragment thereof; monoclonal antibodies or fragment thereof; chimeric antibodies or fragment thereof; CDR-grafted antibodies or fragment thereof; anti-idiotypic antibodies or fragment thereof; and variable region fragments including Fab or Fab' fragments.

The selective binding agent or fragment thereof can comprise at least one complementarity determining region with specificity for a polypeptide having the amino acid sequence of SEQ ID NO: 4, SEQ ID NO: 5, SEQ ID NO: 6, or SEQ ID NO: 10. Also, the selective binding agent can be bound to a detectable label. The invention provides for selective binding agents that act as agonists or antagonists of BARA polypeptide biological activity, preferentially as agonists.

The invention further provides a method for treating, preventing, or ameliorating a BARA polypeptide-related disease, condition, or disorder comprising administering to a patient an effective amount of a selective binding agent of the invention. Such selective binding agent can be produced, inter alia by immunizing an animal with a polypeptide comprising an amino acid sequence of SEQ ID NO: 4, SEQ ID NO: 5, SEQ ID NO: 6, or SEQ ID NO: 10. Hybridomas producing selective binding agents capable of binding a polypeptide of the invention are also provided.

The invention also provides a method of detecting or quantitating the amount of BARA polypeptide in a sample, preferably a biological sample, using anti-BARA antibodies of the invention or fragments thereof.

In a fourth aspect, the invention provides compositions comprising a polypeptide of the invention and a pharmaceutically acceptable formulation agent, wherein the pharmaceutically acceptable formulation agent can be a carrier, adjuvant, solubilizer, stabilizer, or anti-oxidant.

A composition of the invention can also comprise a nucleic acid molecule of the invention and a pharmaceutically acceptable formulation agent, which nucleic acid can be contained in a vector such as a viral or retroviral vector.

The invention provides methods for diagnosing a pathological condition or a susceptibility to a pathological condition in a subject comprising the steps of determining the presence or amount of expression of a polypeptide of the invention or the polypeptide encoded by a nucleic acid molecule of the invention in a sample; and diagnosing a pathological condition or a susceptibility to a pathological condition based on the presence or amount of expression of the polypeptide. In these methods of diagnosing a medical disease, condition, or disorder, expression or lack thereof of a BARA polypeptide or abnormal activity of a BARA polypeptide of the invention is detected in cells or a tissue affected by the disease, condition or disorder. In preferred embodiments, the disease, disorder or condition relates to pathological cell proliferation, most preferably being or malignant neoplasia. In preferred embodiments, BARA polypeptide expression or activity is detected using a specific binding agent of the invention. In preferred embodiments, the specific binding agents are used for in situ immunohistochemistry, ELISA or radio-immunoassay, and in these embodiments the agents are either themselves detectably labeled or are further reacted with detectably-labeled immunological reagent. In alternative preferred embodiments, BARA polypeptide expression or activity is detected using a nucleic acid of the invention, preferably a fragment thereof comprising from about 15 to about 200 nucleotides. In preferred embodiments, the nucleic acids of the invention are used in situ hybridization assays. In alternative preferred embodiments, the nucleic acids of the invention are used as probes for immobilized hybridization. In these embodiments, the nucleic acid or fragment thereof is preferably detectable labeled.

The invention also provides methods for treating, preventing, or ameliorating a medical disease, condition, or disorder comprising the step of administering to a patient in need thereof an effective amount of a polypeptide of the invention or the polypeptide encoded by a nucleic acid of the invention. In preferred embodiments, the disease, disorder or condition relates to pathological cell proliferation, most preferably benign or malignant neoplasia.

A method of identifying a compound that binds to a BARA polypeptide comprising the steps of contacting a polypeptide of the invention with a compound; and determining the extent of binding of the BARA polypeptide to the compound is provided. Such method can further comprise determining the activity of the polypeptide when bound to the compound. Further, a method of modulating levels of a polypeptide in an animal comprising administering to the animal a nucleic acid molecule of the invention is provided.

A transgenic non-human mammal comprising a nucleic acid molecule of the invention is provided as is a process for determining whether a compound stimulates or inhibits BARA polypeptide activity or BARA polypeptide production comprising exposing a transgenic mammal as described hereinto the compound, and measuring BARA polypeptide activity or BARA polypeptide production in the transgenic mammal.

Specific preferred embodiments of the present invention will become evident from the following more detailed description of certain preferred embodiments and the claims.

BRIEF DESCRIPTION OF THE FIGURES

FIG. 7 shows an amino acid sequence alignment of members of the LIN9 family.

DETAILED DESCRIPTION OF THE INVENTION

Figure 1:
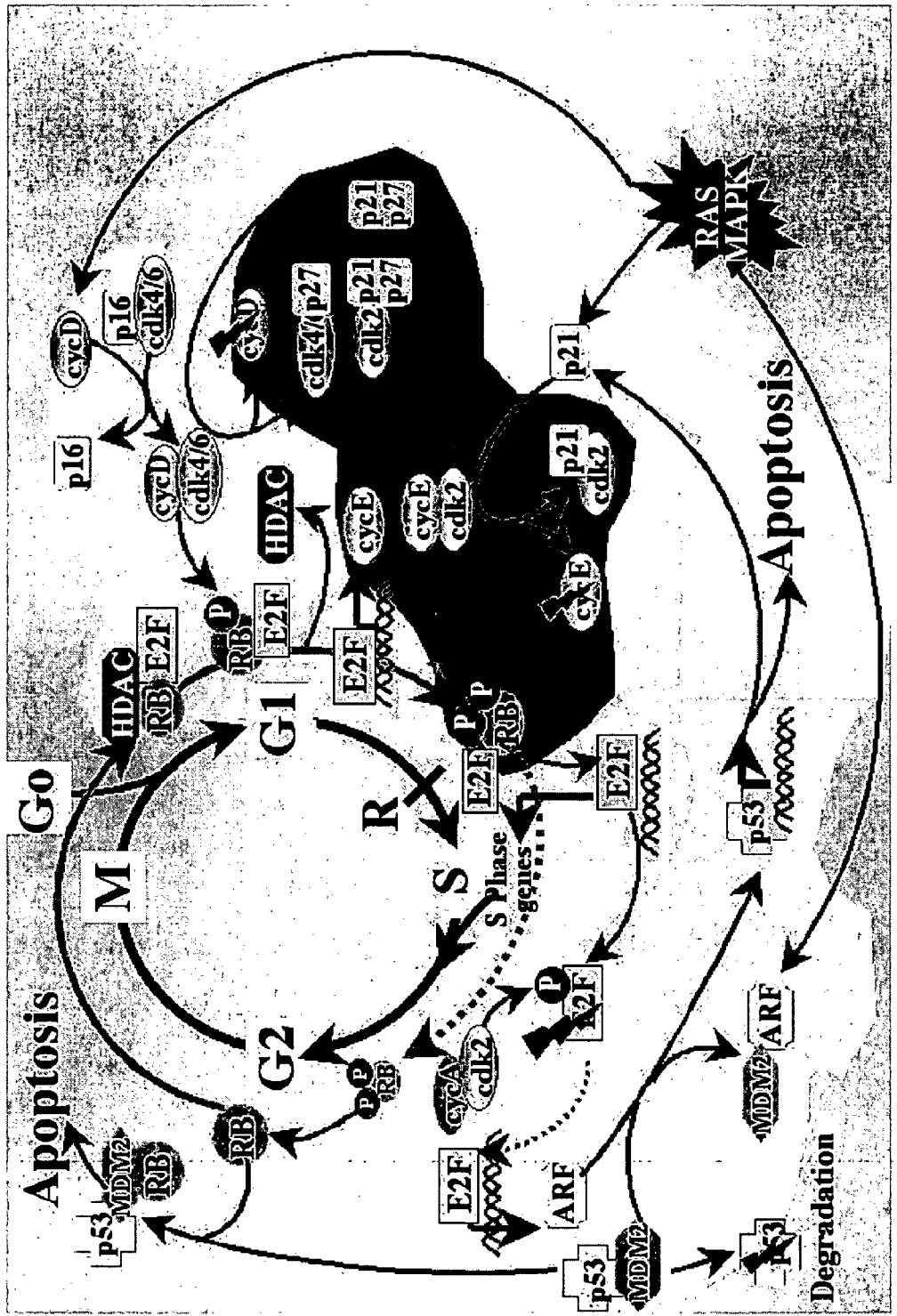
FIG. 1 shows a schematic representation of the cell cycle and its regulation.

The section headings used herein are for organizational purposes only and are not to be construed as limiting the subject matter described. All references cited in this application are expressly incorporated by reference herein.

Definitions

The terms "BARA gene" or "BARA nucleic acid molecule" or "BARA polynucleotide" refer to a nucleic acid molecule comprising a human or mouse nucleotide sequence as set forth in SEQ ID NO: 1, SEQ ID NO: 2, SEQ ID NO: 3, or SEQ ID NO: 9, a nucleotide sequence encoding the polypeptide as set forth in SEQ ID NO: 4, SEQ ID NO: 5, SEQ ID NO: 6, or SEQ ID NO: 10, and nucleic acid molecules as defined herein. Included in this definition are: BARA polypeptide allelic variants, which are one of a plurality of naturally occurring alternate forms of a gene occupying a particular locus on a chromosome of an organism or a population of organisms, preferably a mammal and most preferably a human; and BARA polypeptide splice variants, that are nucleic acid molecules, usually an RNA molecule, generated by alternative processing of intron sequences in an RNA transcript encoding a BARA polypeptide amino acid sequence as set forth in SEQ ID NO: 4, SEQ ID NO: 5, SEQ ID NO: 6, or SEQ ID NO: 10.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell, particularly wherein said coding information is in the form of a nucleic acid that is from a different cell than the host cell.

The term "expression vector" refers to a vector that is suitable for transferring coding information into a host cell and contains nucleic acid sequences that direct and/or control the expression of inserted heterologous nucleic acid sequences. Expression includes, but is not limited to, cellular processes such as transcription, translation, and RNA splicing, if introns are present.

The term "operably linked" is used herein to refer to an arrangement of nucleic acid sequences wherein the sequences so described are configured or assembled so as to perform a desired function. Thus, a flanking sequence operably linked to a coding sequence may be capable of effecting replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell that has been transformed, or is capable of being transformed with a nucleic acid sequence and then of expressing a gene of interest, preferably encoded by the transferred nucleic acid sequence. The term includes the progeny of the parent cell, whether or not the progeny is identical in morphology or in genetic make-up to the original parent, so long as the gene is present.

The term "BARA polypeptide" refers to a polypeptide comprising the amino acid sequence of SEQ ID NO: 4, SEQ ID NO: 5, SEQ ID NO: 6, or SEQ ID NO: 10 and related polypeptides. Related polypeptides include BARA polypeptide fragments, BARA polypeptide variants, and BARA polypeptide derivatives, which possess at least one activity of the polypeptide as set forth in SEQ ID NO: 4, SEQ ID NO: 5, SEQ ID NO: 6, or SEQ ID NO: 10. BARA polypeptides may be mature polypeptides, as defined herein, and may or may not have an amino-terminal methionine residue, depending on the method by which they are prepared.

The term "BARA polypeptide" also includes BARA polypeptide fragments, BARA polypeptide variants, BARA polypeptide derivatives, mature BARA polypeptide, BARA fusion polypeptide, and biologically active BARA polypeptides.

BARA polypeptide fragments, include polypeptides that comprise a truncation at the amino-terminus (with or without a leader sequence), a truncation at the carboxyl-terminus of the polypeptide as set forth in SEQ ID NO: 4, SEQ ID NO: 5, SEQ ID NO: 6, or SEQ ID NO: 10, or both. BARA polypeptide fragments also include amino-terminal and/or carboxyl-terminal truncations of BARA polypeptides or to amino-terminal and/or carboxyl-terminal truncations of the polypeptides encoded by BARA polypeptide allelic variants or BARA polypeptide splice variants. BARA polypeptide fragments may result from alternative RNA splicing or from in vivo protease activity. Membrane-bound forms of BARA polypeptides are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids, or more than about 200 amino acids. Such BARA polypeptide fragments may optionally comprise an amino-terminal methionine residue. It will be appreciated that such fragments can be used, for example, to generate antibodies to BARA polypeptides.

BARA polypeptide variants inlcudes BARA polypeptides comprising amino acid sequences having one or more amino acid sequence substitutions, deletions (such as internal deletions and/or BARA polypeptide fragments), and/or additions (such as internal additions and/or BARA fusion polypeptides) as compared to the BARA polypeptide amino acid sequence set forth in SEQ ID NO: 4, SEQ ID NO: 5, SEQ ID NO: 6, or SEQ ID NO: 10 (with or without a leader sequence). Variants may be naturally occurring (e.g., BARA polypeptide allelic variants and BARA polypeptide splice variants) or artificially constructed. Such BARA polypeptide variants may be prepared from the corresponding nucleic acid molecules having a DNA sequence that varies accordingly from the DNA sequence as set forth in SEQ ID NO: 1, SEQ ID NO: 2, SEQ ID NO: 3, or SEQ ID NO: 9. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

BARA polypeptide derivatives include polypeptides as set forth in SEQ ID NO: 4, SEQ ID NO: 5, SEQ ID NO: 6, or SEQ ID NO: 10, BARA polypeptide fragments, or BARA polypeptide variants, as defined herein, that have been chemically modified. The term "BARA polypeptide derivatives" also refers to polypeptides encoded by BARA polypeptide allelic variants or BARA polypeptide splice variants, as defined herein, that have been chemically modified as disclosed herein and known to those with skill in the art.

Mature BARA polypeptides include BARA polypeptides lacking a leader sequence. A mature BARA polypeptide may also include other modifications such as proteolytic processing of the amino-terminus (with or without a leader sequence) and/or the carboxyl-terminus, cleavage of a smaller polypeptide from a larger precursor, N-linked or O-linked glycosylation or both, and the like.

BARA fusion polypeptides includes fusion of one or more amino acids (such as a heterologous protein or peptide) at the amino- or carboxyl-terminus of the polypeptides as set forth in SEQ ID NO: 4, SEQ ID NO: 5, SEQ ID NO: 6, or SEQ ID NO: 10, BARA polypeptide fragments, BARA polypeptide variants, or BARA derivatives, as defined herein. The term "BARA fusion polypeptide" also refers to a fusion of one or more amino acids at the amino- or carboxyl-terminus of the polypeptide encoded by BARA polypeptide allelic variants or BARA polypeptide splice variants, as defined herein.

Biologically active BARA polypeptides includes BARA polypeptides having at least one activity characteristic of the polypeptide comprising the amino acid sequence of SEQ ID NO: 4, SEQ ID NO: 5, SEQ ID NO: 6, or SEQ ID NO: 10. In addition, a BARA polypeptide may be active as an immunogen; that is, the BARA polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, isolated polypeptides of the invention are substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to material that is not found in nature or that has been structurally modified or synthesized by man. When used in connection with nucleotides, the terms "naturally occurring" or "native" refer to the bases adenine (A), cytosine (C), guanine (G), thymine (T), and uracil (U). When used in connection with amino acids, the terms "naturally occurring" and "native" refer to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The terms "effective amount" and "therapeutically effective amount" each refer to the amount of a BARA polypeptide or BARA nucleic acid molecule used to support an observable level of one or more biological activities of the BARA polypeptides as set forth herein.

The term "pharmaceutically acceptable carrier" or "physiologically acceptable carrier" as used herein refers to one or more formulation materials suitable for accomplishing or enhancing the delivery of the BARA polypeptide, BARA nucleic acid molecule, or BARA selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a BARA polypeptide. As used herein, the terms, "specific" and "specificity" refer to the ability of the selective binding agents to bind to human BARA polypeptides and not to bind to human non-BARA polypeptides or to bind mouse BARA polypeptides and not to bind to mouse non-BARA polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain nucleic acid species not endogenous to the cell. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "anti-neoplastic" or "anti-tumor" as used herein refers to the inhibition or arrest of the growth, and/or the destruction of mammalian benign or malignant neoplasms.

The invention disclosed herein provides BARA-encoding nucleic acid, BARA polypeptides and reagents and methods related thereto relating to the biological role of BARA in events that lead to inhibition of cellular proliferation through senescence and/or apoptosis, i.e., cell death.

Regulation of Cell Cycle, Interferons (IFNs), Senescence and Relation to BARA

The RB gene was the first tumor suppressor gene identified (for review see DiCiommo et al., 2000, *Sem. Cancer Biol.* 10:255). RB regulates the passage from $G_1$ to S phase by tightly controlling the restriction point. Once cells pass the restriction point, they are committed to enter the synthesis or "S" phase of the cell cycle where DNA is duplicated before entering the final stage, mitosis (Id.). RB itself is regulated by well-defined phosphorylation events that occur during G₁ and lead to its functional inactivation (see FIG. 1, light and dark green).

RB phosphorylation is regulated by specific cyclin/CDK complexes. Different mitogens induce activation of the cyclin D-CDK4/6 complex, which is responsible for the initial phosphorylation of RB. This leads to the partial release of E2F and HDAC from the complex initially formed with RB (FIG. 1, light green), which in turn induces transcription of the cyclin E gene. Cyclin E forms a complex with CDK2 that accounts for additional phosphorylation of RB, whereby RB is completely inactivated and permits passage of the cell through the cell cycle restriction point (FIG. 1, dark green). At this point, transcriptional repression of RB-E2F complex is eliminated resulting in the induction of "S" phase genes. Thus, initial phosphorylation of RB by cyclin D/CDK4-6 is mitogen-dependent, while inactivation of RB by cyclin E/CDK2 is mitogen-independent and marks the "point of no return," the commitment of cells to enter S phase (see, for example, Adams et al., 1995, *Semin Cancer Biol* 6:99).

Cyclins are tightly regulated by ubiquitination and degradation (broken red arrow heads), and their levels of expression fluctuate along the cell cycle (Sherr, 1996, *Science* 274:1672). The cyclin/CDK complexes are also tightly regulated by inhibitors or CKIs (FIG. 1). For example, the INK4 family of proteins ($p16^{INK4a}$, $p15^{INK4b}$, $p18^{INK4c}$, and $p19^{INK4d}$) regulate cyclin D/CDK4-6 activity (light green area) while cyclin E/CDK2 is regulated by p21, p27 and p57 inhibitors (dark green area) (Vidal et al., 2000, *Gene* 247:1).

Factors that increase levels of p15, p16, p18 or p19 diminish activation of cyclin D/CDK4-6 complexes and initial phosphorylation of RB, while factors that induce p21, p27 or p57 inhibit cyclinE/CDK2 activity. TGFβ specifically induces p15 resulting in accumulation of cells in G₁. Other factors such as interferons (IFNs) also produce G₁ arrest.

Figure 2:
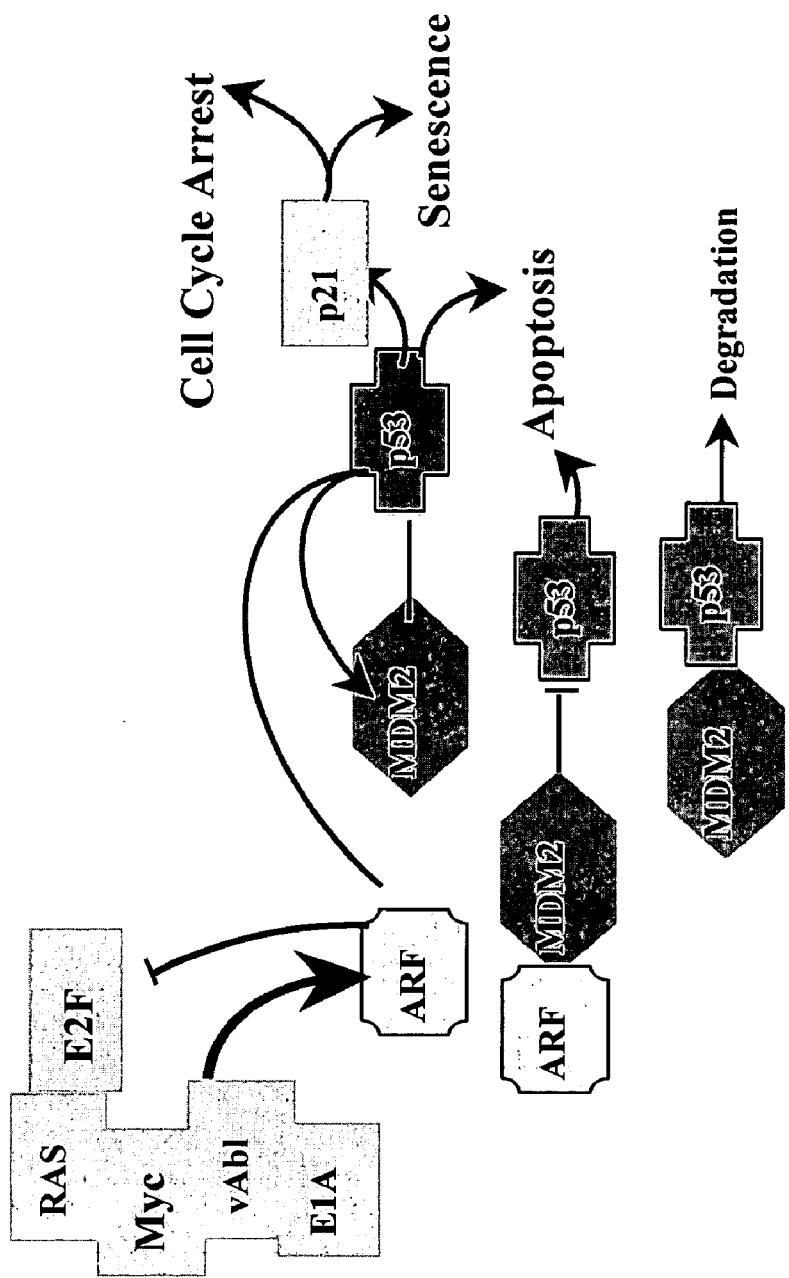
FIG. 2 shows regulation of the ARF-MDM2-p53 pathway by oncogenic signals. MDM2 targets p53 for degradation, and this process is inhibited by ARF.

Malignant transformation involves deregulation of a cell cycle restriction point by either the absence of functional RB, the amplification of cyclin D, or the loss of $p16^{INK4a}$ (see, for example, Sellers et al., 1997, *J Clin Oncol* 15:3301). However, additional events are required for emergence of a malignant phenotype due to built-in safety mechanisms that result in cell cycle arrest, senescence or apoptosis. These safety mechanisms are triggered by hyperproliferative signals such as oncogenic Ras, myc, E2F1, vAbl and E1A (FIG. 2). The main effector of this safety mechanism is the ARF-MDM2-p53 pathway. For example, the absence of RB leads to unleashed activity of E2F, which, if maintained after entrance into S phase, triggers transcription of $p19^{ARF}$ (FIG. 1, blue dotted line and yellow area and FIG. 1). Inhibition of MDM2 by $p19^{ARF}$ stabilizes p53, which in turn induces transcription of p21 and other genes that result in cell cycle arrest, senescence or apoptosis (see, for example, Qin et al., 1994, *Proc Natl Acad Sci USA* 91:10918). Interestingly, oncogenic RAS induces the ARF-MDM2-p53 pathway leading to transcription of p21 and senescence (see, for example, Bates et al., 1998. *Nature* 395:124), while activation of the ARF-MDM2-p53 pathway by E2F, c-MYC, E1A, and v-Abl results in apoptosis (see, for example, Prendergast, 1999, Oncogene 18:2967). These mechanisms explain why most tumors not only have alterations of the RB pathway (i.e. either inactivation of tumor suppressors RB or p16, or amplification of Cyclin D or CDK4/6), but also mutations in p53 or ARF allowing cells to escape cell cycle arrest and/or apoptosis. It has also been proposed that the RB and p53 pathways are interconnected since MDM2, the main regulator of p53, can interact with RB (FIG. 1, upper left corner) (Hsieh et al., 1999, *Mol. Cell* 3:181).

It has been proposed that since ARF and p53 are in the same linear pathway, tumor cells do not have to mutate both genes to escape the tumor surveillance mechanism (Sherr et al., 2000, *Current Opinion Gen. Develop.* 10:94). However, this concept has been challenged by the finding that mutation of ARF and p53 may coexist in some tumor cells and that ARF has p53-independent functions since ARF can induce cell cycle arrest in $p53^{-/-}$ cells through the regulation of p16-RB Carnero et al., 2000, *Nat. Cell Biol.* 2:148-55., 2000]. Murine embryonic fibroblasts (MEFs) null for p53 or ARF bypass the normal senescence mechanisms present in wild type cells, yet the concomitant deletion of ARF and CDK4 restores normal senescence and abrogates the ability of RAS to transform $ARF^{-/-}$ MEFs Zuo et al., 2002, *Genes Develop.* 16:2923-2934. This process involves induction of p21 and is reverted by siRNA against this CKI, which suggests that there are ARF-independent mechanisms downstream of CDK4 that regulate senescence.

Biological Functions of Type I IFNs

Interferons (IFN) were first described on the basis of their ability to "interfere" with viral infection. However, a wide variety of actions such as antiproliferative activity, modulation of the immune response, and boosting of natural killer cell activity have been assigned to IFNs. There are two types of IFNs: (i) type I IFNs that consist of IFNα, β, and co, and (ii) type II IFNs represented by IFNγ. The α subfamily includes several different subtypes (designated as α1, α2, etc), while there is only one IFNβ and ω. All type I IFNs (α, β, and ω) bind to the same cell surface receptor commonly designated as type I IFN receptor (type I IFN-R), IFNα receptor (IFNαR), or IFNαβR. The receptor for IFNγ (type II IFN) has been designated as the IFNγ receptor (IFNγR) or type II IFN-R (see, for example, Rubinstein et al., 1998, *Cytokine Growth Factor Rev,* 9:175).

Figure 3:
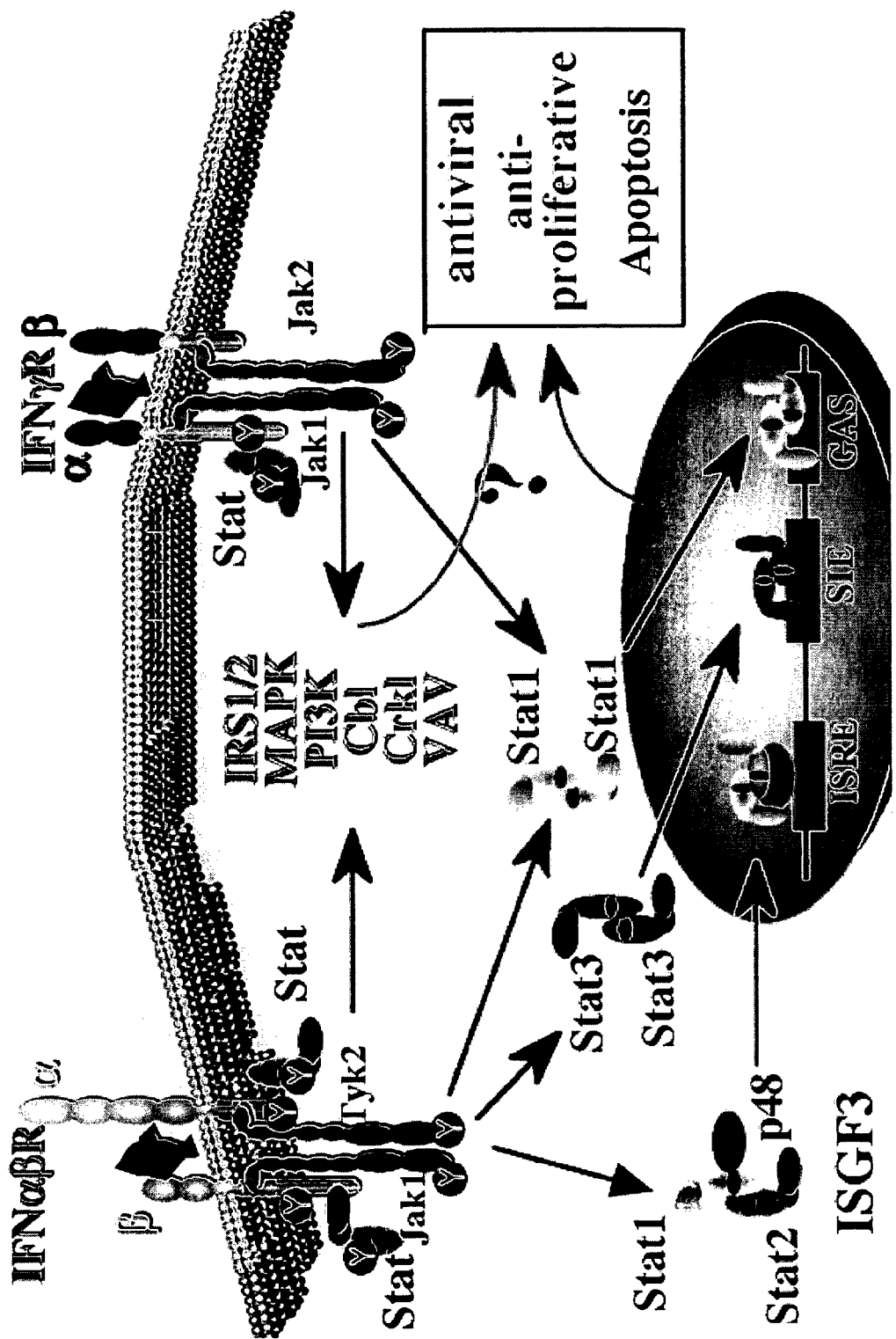
FIG. 3 shows signaling by Type I and Type II IFNs. The activation of the Jak-Stat pathway by IFNα/β and IFNγ systems is shown. IFNs activate Jak kinases. Jak1 and Tyk2 first phosphorylate the receptor. These phosphotyrosines serve as docking sites for Stats, which then phosphorylated by the Jaks. Phosphorylated Stat1 forms homodimers designated as GAF, which translocate to the nucleus where they bind gamma-activated sequence (GAS) to induce specific genes. In the IFNα system, Stat2 is constitutively associated with IFNαRβL after receptor activation. Heterodimers of Stat1/2 (ISGF3α) interact with a protein of the IRF family, p48/ISGF3γ/IRF9 to form ISGF3, which translocates to the nucleus where it binds the interferon-stimulated response element (ISRE). The activation of other signaling proteins by Type I and Type II IFNs is also shown.

The type I IFN system has played a central role in characterizing new signaling mechanisms that involve direct signaling from the cell membrane to the nucleus (see Darnell et al., 1994, *Science* 264:1415). FIG. 3 shows that binding of type I IFNs to a cell surface receptor results in activation of Jak kinases (Jak1 and Tyk2) that are responsible for tyrosine phosphorylation of latent cytoplasmic transcription factors designated as Stat1 and Stat2 (signal transducers and activators of transcription). Stat1, Stat2 and a protein of the IRF family, p48/IRF9, form the ISGF3 complex that translocates to the nucleus where it binds specific promoters to regulate gene transcription. Type I IFNs also induce the formation of STAT1-STAT1 and STAT1-STAT3 dimers that bind to specific DNA elements (see, for example, Leonard et al., 1998, *Annu. Rev. Immunol.* 16:293), and together with ISGF3 regulate transcription of specific genes responsible for the antiviral and antiproliferative effects of IFNs. Several cytokine systems whose receptors are members of the cytokine receptor superfamily use a similar signaling mechanism (see, for example, Ihle et al., 1994, *TIBS,* 19:222). As expected, the integrity of the Jak-Stat pathway is required for the antiviral and antiproliferative effects (see, for example, Bromberg et al., 1996, *Proc. Natl. Acad. Sci. USA,* 93:7673).

Figure 4:
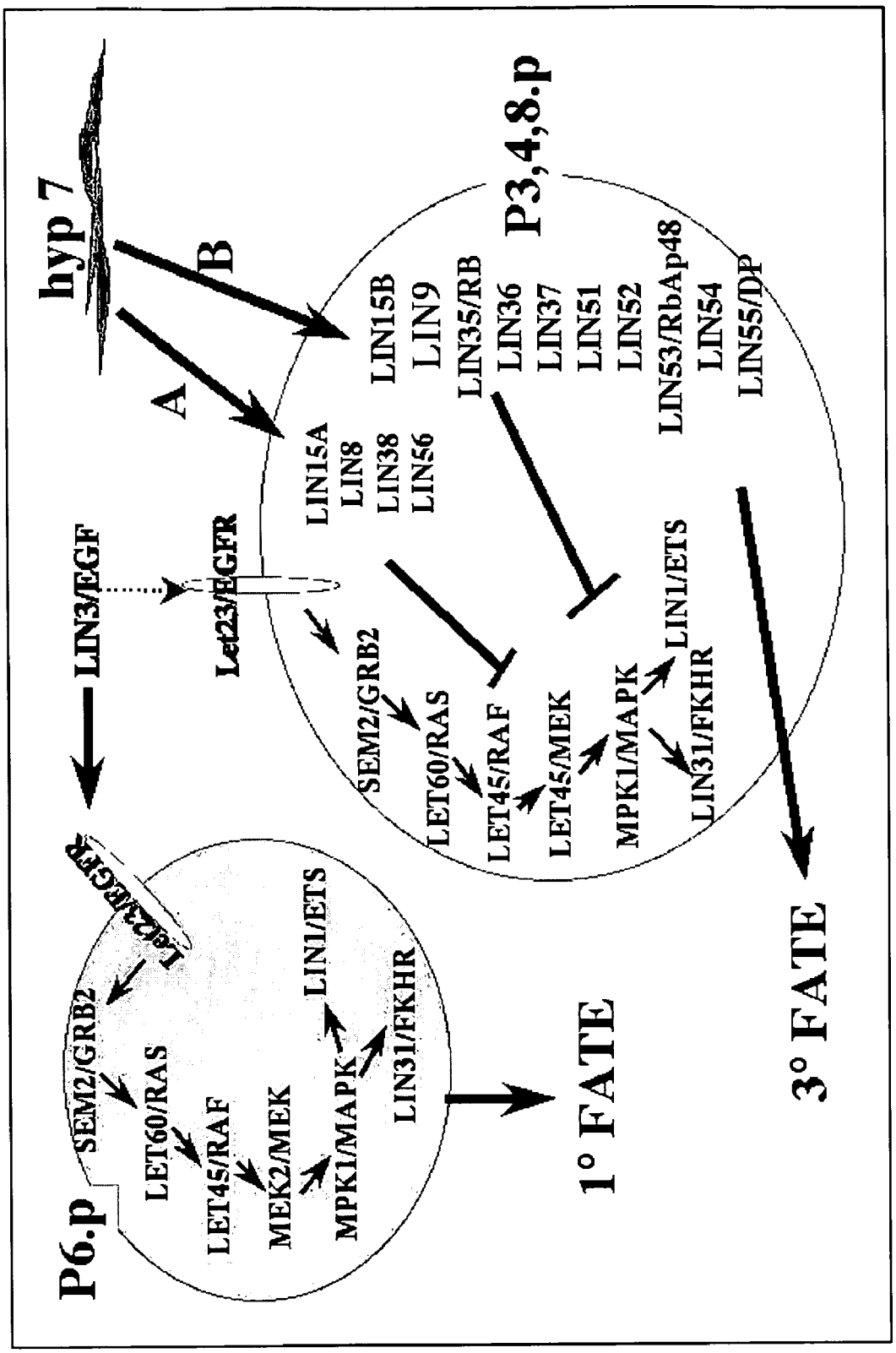
FIG. 4 shows a representation of the positive (RAS→MAPK in P6.p) and negative regulatory pathways (A and B that affect P3.p, P4.p and P8.p) responsible for vulva formation in C. elegans.
Figure 5:
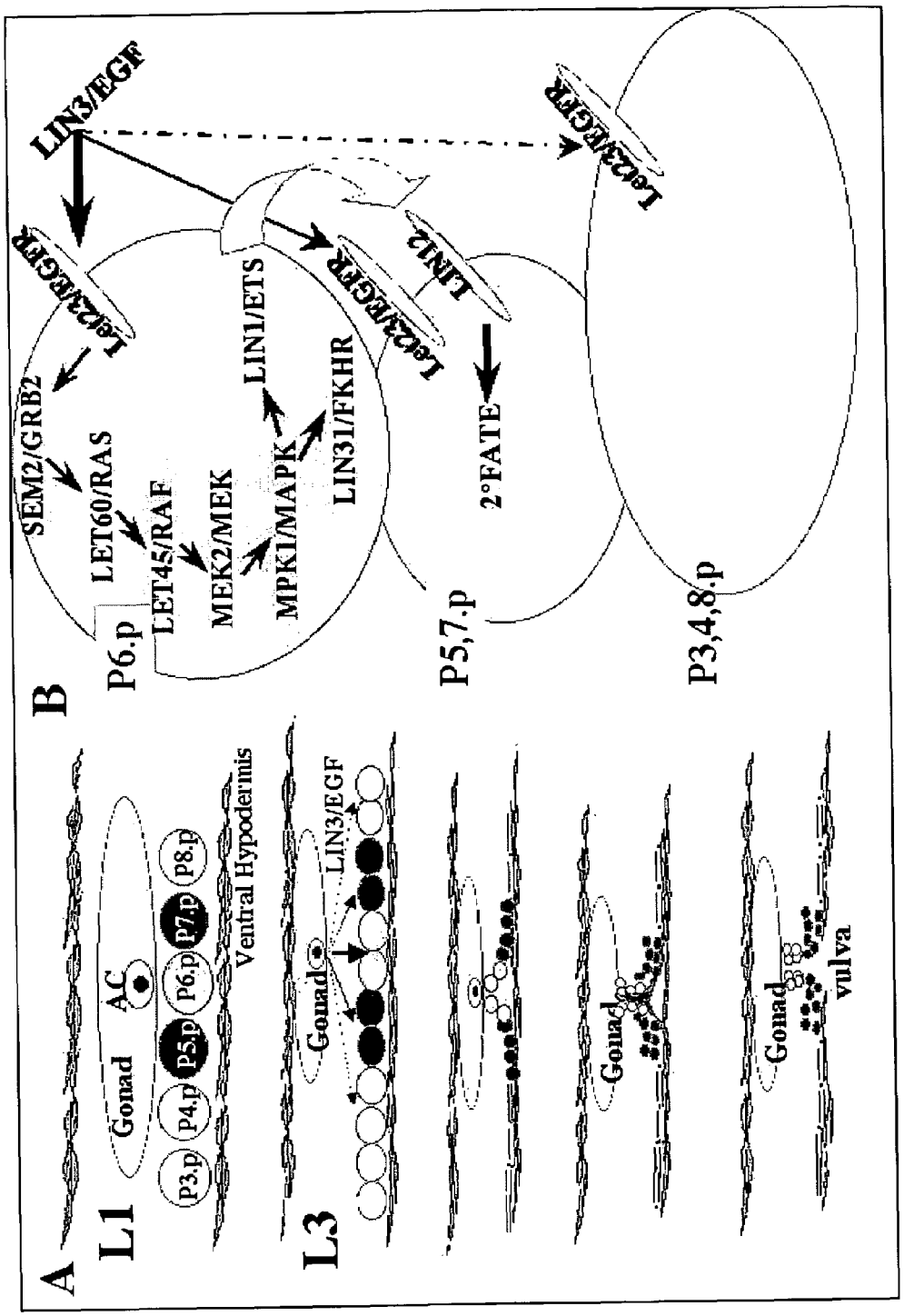
FIG. 5 shows a schematic representation of vulva development (A) and its regulatory pathway (B) in C. elegans.

Vulva Development in *C. elegans*. A Model for the Study of the Role of EGF-RAS-MAPK Pathway in Cell Proliferation and its Negative Regulation by the Retinoblastoma (RB) Pathway The process of vulva development in *C. elegans* provides an excellent model for studying signaling through the EGF>>EGF-R>>GRB2>>RAS>>RAF>>MEK>>MAPK pathway, as well as its negative regulation by two redundant overlapping pathways termed A and B (FIG. 4). In the L3 stage, the Anchor Cell (FIG. 5, A, AC) in the gonad releases LIN-3/EGF that activates the corresponding receptor, LET- 23/EGFR (FIG. 5, B), in the vulva precursor cells (VPC). There are six hypodermal VPCs designated as P3.p-P8.p, each of which has the potential to form the vulva (see FIG. 5, A). Normally P6.p, the nearest VPC to the AC, is the target of most of the LIN-3/EGF released by the AC due to its proximity and assumes the primary (1°) fate responsible for the formation of the vulva (FIG. 5, A, red cells). Lower levels of activation of the EGFR in P5.p and P7.p (blue cells), and a lateral signal produced by P6.p that activates the LIN-12 pathway (FIG. 5, B, thick arrow), determines the secondary (2°) fate of the neighboring P5.p and P7.p cells (FIG. 5, A, blue cells). In the case of P3.p, P4.p and P8.p (FIG. 5, white cells), low levels of stimulation by LIN3/EGF and additional activation of two negative regulatory pathways originated in the surrounding hypodermis (Hyp7), termed A and B (FIG. 4), induce the tertiary (3°) or non-vulval fate.

Cells derived from P5.p and P7.p form the sides of the vulva. In the case of P3.p, P4.p and P8.p (FIG. 5, A, white cells), low levels of stimulation by LIN-3/EGF and additional activation of two negative regulatory pathways originated in the surrounding hypodermis (Hyp7) (FIG. 4), make these cells acquire the tertiary (3°) or non-vulval fate. P3.p, P4.p and P8.p end up fusing with hyp 7, the hypodermal syncytium of the worm. In summary, the pattern of fates for P3.p-P8.p is 3°, 3°, 2°, 1°, 2°, 3°, respectively, and is determined by the gradient of the inductive signal (LIN-3/EGF), the lateral signal from P6.p, and inhibitory signals from the hypodermal syncytium.

Gain- or loss-of-function alterations of the inductive (EGF), lateral, or inhibitory signals may result in Vulvaless or Synthetic Multivulva (SynMuv) phenotypes. In the case of the two hypodermal inhibitory pathways (A and B), the SynMuv phenotype is observed only when genes in both pathways are simultaneously mutated indicating that these pathways are redundant. Genetic studies have identified genes for both pathways. Four genes are known in pathway A: lin-15A, lin-8, lin-38, lin-56. The genes identified in pathway B are lin-15B, lin-9, lin-35, lin-36, lin-37, lin-51, lin-52, lin-53, lin-54, and lin-55. Interestingly, the mammalian counterparts of many of the genes in pathway B correspond to proteins that function in the retinoblastoma (RB) pathway. For instance, lin-35 has homology with RB itself, lin-53 is homologous to E2F, and lin-54 with p48αRβ. This clearly indicates that the B pathway may regulate the cell cycle and differentiation in VPCs and likely in other lineages in C. elegans. A recent report has clearly established that C. elegans LIN-9 regulates $G_1$ downstream of cyclin D/CDK4 however, LIN-9 and RB did not appear to be in the same linear pathway (Boxen et al., 2002, Current Biol. 12:906-911).

Relatedness of Nucleic Acid Molecules and/or Polypeptides

Related nucleic acid molecules include allelic or splice variants of the nucleic acid molecule of SEQ ID NO: 1, SEQ ID NO: 2, SEQ ID NO: 3, or SEQ ID NO: 9, and include sequences which are complementary to any of the above nucleotide sequences. Related nucleic acid molecules also include nucleotide sequences encoding polypeptides comprising substitutions, modifications, additions and/or deletions of one or more amino acid residues compared to the polypeptide as set forth in SEQ ID NO: 4, SEQ ID NO: 5, SEQ ID NO: 6, or SEQ ID NO: 10. Such related BARA polypeptides may comprise, for example, an addition and/or a deletion of one or more N-linked or O-linked glycosylation sites or an addition and/or a deletion of one or more cysteine residues.

Related nucleic acid molecules also include fragments of BARA nucleic acid molecules that encode polypeptides of at least about 25 contiguous amino acids, or about 50 amino acids, or about 75 amino acids, or about 100 amino acids, or about 150 amino acids, or about 200 amino acids, or more than about 200 amino acid residues of the BARA polypeptide of SEQ ID NO: 4, SEQ ID NO: 5, SEQ ID NO: 6, or SEQ ID NO: 10.

In addition, related BARA nucleic acid molecules also include those molecules comprising nucleotide sequences that hybridize under moderately or highly stringent conditions as defined herein with the fully complementary sequence of the BARA nucleic acid molecule of SEQ ID NO: 1, SEQ ID NO: 2, SEQ ID NO: 3, or SEQ ID NO: 9, or of a molecule encoding a polypeptide comprising an amino acid sequence as shown in SEQ ID NO: 4, SEQ ID NO: 5, SEQ ID NO: 6, or SEQ ID NO: 10, or of a nucleic acid fragment as defined herein, or of a nucleic acid fragment encoding a BARA polypeptide as defined herein. Hybridization probes may be prepared using the BARA sequences provided herein to screen cDNA, genomic or synthetic DNA libraries for related sequences. Regions of DNA and/or amino acid sequence of BARA polypeptide that exhibit significant identity to known sequences are readily determined using sequence alignment algorithms as described herein and those regions may be used to design probes for screening.

The term "highly stringent conditions" refers to conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook et al., 1989, Molecular Cloning: A Laboratory Manual (2nd ed., Cold Spring Harbor Laboratory: New York); Anderson et al., Nucleic Acid Hybridisation: A Practical Approach Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples include 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridisation: A Practical Approach Ch. 4 (IRL Press Limited).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching is able to form than could occur under "highly stringent conditions". Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl (6×SSC) for oligonucleotide probes up to about 20 nt is given by:

$$Tm = 2° C. \text{ per } A\text{-}T \text{ base pair} + 4° C. \text{ per } G\text{-}C \text{ base pair}$$

See Suggs et al., 1981, *Developmental Biology Using Purified Genes* 683 (Brown and Fox, eds., Academic Press, New York).

High stringency washing conditions for oligonucleotides are usually at a temperature of 0-5° C. below the $T_m$ of the oligonucleotide in 6×SSC, 0.1% SDS.

In another embodiment, related nucleic acid molecules comprise nucleotide sequences that are at least about 70 percent identical to a nucleotide sequence as shown in SEQ ID NO: 1, SEQ ID NO: 2, SEQ ID NO: 3, or SEQ ID NO: 9. In preferred embodiments, the nucleotide sequences are about 75 percent, or about 80 percent, or about 85 percent, or about 90 percent, or about 95, 96, 97, 98, or 99 percent identical to a nucleotide sequence as shown in SEQ ID NO: 1, SEQ ID NO: 2, SEQ ID NO: 3, or SEQ ID NO: 9. Related nucleic acid molecules encode polypeptides possessing at least one activity of a polypeptide set forth in SEQ ID NO: 4, SEQ ID NO: 5, SEQ ID NO: 6, or SEQ ID NO: 10.

Differences in nucleic acid sequence may result in conservative and/or non-conservative modifications of an amino acid sequence relative to an amino acid sequence of SEQ ID NO: 4, SEQ ID NO: 5, SEQ ID NO: 6, or SEQ ID NO: 10.

Conservative modifications to an amino acid sequence of SEQ ID NO: 4, SEQ ID NO: 5, SEQ ID NO: 6, or SEQ ID NO: 10 (and corresponding modifications to encoding nucleic acids) will produce polypeptides having functional and chemical characteristics similar to those of BARA polypeptides. In contrast, substantial modifications in the functional and/or chemical characteristics of BARA polypeptides may be accomplished by selecting substitutions in an amino acid sequence of SEQ ID NO: 4, SEQ ID NO: 5, SEQ ID NO: 6, or SEQ ID NO: 10 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve exchange of a member of one of these classes for a member from another class. Such substituted residues may be introduced into regions of the human BARA polypeptide that are homologous with non-human BARA polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that substitution of like amino acids can be made effectively on the basis of hydrophilicity, particularly where the biologically functionally equivalent protein or peptide thereby created is intended for use in immunological embodiments. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the BARA polypeptide, or to increase or decrease the affinity of the BARA polypeptides described herein. Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of a polypeptide as set forth in SEQ ID NO: 4, SEQ ID NO: 5, SEQ ID NO: 6, or SEQ ID NO: 10 using well-known techniques. For identifying suitable areas of the molecule that may be changed without destroying biological activity, one skilled in the art may target areas not understood to be important for activity. For example, when similar polypeptides with similar activities from the same species or from other species are known, one skilled in the art may compare the amino acid sequence of a BARA polypeptide to such similar polypeptides. With such a comparison, one can identify residues and portions of the molecules that are conserved among similar polypeptides. It will be appreciated that changes in areas of the BARA molecule that are not conserved relative to such similar polypeptides would be less likely to adversely affect the biological activity and/or structure of a BARA polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a BARA polypeptide that correspond to amino acid residues that are important for activity or structure in similar polypeptides. One skilled in the art may opt for chemically similar amino acid substitutions for such predicted important amino acid residues of BARA polypeptides.

One skilled in the art can also analyze the three-dimensional structure and amino acid sequence in relation to that structure in similar polypeptides. In view of such information, one skilled in the art may predict the alignment of amino acid residues of BARA polypeptide with respect to its three dimensional structure. For example, one skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants can be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996*, Curr. Opin. Biotechnol.* 7:422-27; Chou et al., 1974, *Biochemistry* 13:22245; Chou et al., 1974, *Biochemistry* 113:211-22; Chou et al., 1978, *Adv. Enzymol. Relat. Areas Mol. Biol.* 47:4548; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999*, Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct Biol.* 7:369-76).

Additional methods of predicting secondary structure include "threading" (Jones, 1997*, Curr. Opin. Struct Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

BARA polypeptide variants can include glycosylation variants wherein the number and/or type of glycosylation sites have been altered compared to an amino acid sequence set forth in SEQ ID NO: 4, SEQ ID NO: 5, SEQ ID NO: 6, or SEQ ID NO: 10. In one embodiment, BARA polypeptide variants comprise a greater or a lesser number of N-linked glycosylation sites than an amino acid sequence set forth in SEQ ID NO: 4, SEQ ID NO: 5, SEQ ID NO: 6, or SEQ ID NO: 10. An N-linked glycosylation site is characterized by the sequence: Asn-X-Ser or Asn-X-Thr, wherein the amino acid residue designated as X may be any amino acid residue except proline. Substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Additional preferred BARA variants include cysteine variants, wherein one or more cysteine residues are deleted or substituted with another amino acid (e.g., serine) as compared to an amino acid sequence set forth in SEQ ID NO: 4, SEQ ID NO: 5, SEQ ID NO: 6, or SEQ ID NO: 10. Cysteine variants are useful when BARA polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, BARA polypeptide variants comprise an amino acid sequence as set forth in SEQ ID NO: 4, SEQ ID NO: 5, SEQ ID NO: 6, or SEQ ID NO: 10 with at least one amino acid insertion and wherein the polypeptide has an antigenic, biological or enzymatic activity of a polypeptide set forth in SEQ ID NO: 4, SEQ ID NO: 5, SEQ ID NO: 6, or SEQ ID NO: 10, or an amino acid sequence encoding a polypeptide as set forth in SEQ ID NO: 4, SEQ ID NO: 5, SEQ ID NO: 6, or SEQ ID NO: 10 with at least one amino acid deletion and wherein the polypeptide has an antigenic, biological or enzymatic activity of a polypeptide set forth in SEQ ID NO: 4, SEQ ID NO: 5, SEQ ID NO: 6, or SEQ ID NO: 10. BARA polypeptide variants also comprise an amino acid sequence as set forth in SEQ ID NO: 4, SEQ ID NO: 5, SEQ ID NO: 6, or SEQ ID NO: 10 wherein the polypeptide has a carboxyl- and/or amino-terminal truncation and further wherein the polypeptide has an antigenic, biological or enzymatic activity of the polypeptide set forth in SEQ ID NO: 4, SEQ ID NO: 5, SEQ ID NO: 6, or SEQ ID NO: 10. BARA polypeptide variants further comprise an amino acid sequence as set forth in SEQ ID NO: 4, SEQ ID NO: 5, SEQ ID NO: 6, or SEQ ID NO: 10 with at least one modification that is an amino acid substitution, amino acid insertion, amino acid deletion, carboxyl-terminal truncation, or amino-terminal truncation, and wherein the polypeptide has an antigenic, biological or enzymatic activity of the polypeptide set forth in SEQ ID NO: 4, SEQ ID NO: 5, SEQ ID NO: 6, or SEQ ID NO: 10.

In further embodiments, BARA polypeptide variants comprise an amino acid sequence that is at least about 70 percent identical to an amino acid sequence as set forth in SEQ ID NO: 4, SEQ ID NO: 5, SEQ ID NO: 6, or SEQ ID NO: 10. In preferred embodiments, BARA polypeptide variants comprise an amino acid sequence that is at least about 75 percent, or about 80 percent, or about 85 percent, or about 90 percent, or about 95, 96, 97, 98, or 99 percent identical to an amino acid sequence as set forth in SEQ ID NO: 4, SEQ ID NO: 5, SEQ ID NO: 6, or SEQ ID NO: 10. BARA polypeptide variants possess at least one biological or enzymatic activity of the polypeptide set forth in SEQ ID NO: 4, SEQ ID NO: 5, SEQ ID NO: 6, or SEQ ID NO: 10.

In addition, a polypeptide comprising the amino acid sequence of SEQ ID NO: 4, SEQ ID NO: 5, SEQ ID NO: 6, or SEQ ID NO: 10, or other BARA polypeptide, may be fused to a homologous polypeptide to form a homodimer or to a heterologous polypeptide to form a heterodimer. Heterologous peptides and polypeptides include, but are not limited to: an epitope that permits detection and/or isolation of a BARA fusion polypeptide; a transmembrane receptor protein or a portion thereof, such as an extracellular domain or a transmembrane and intracellular domain; a ligand or a portion thereof that binds to a transmembrane receptor protein; an enzyme or portion thereof that is catalytically active; a polypeptide or peptide that promotes oligomerization, such as a leucine zipper domain; a polypeptide or peptide that increases stability, such as an immunoglobulin constant region; and a polypeptide that has a therapeutic activity different from a polypeptide comprising the amino acid sequence as set forth in SEQ ID NO: 4, SEQ ID NO: 5, SEQ ID NO: 6, or SEQ ID NO: 10, or other BARA polypeptide.

Fusions can be made either at the amino-terminus or at the carboxyl-terminus of a polypeptide comprising an amino acid sequence set forth in SEQ ID NO: 4, SEQ ID NO: 5, SEQ ID NO: 6, or SEQ ID NO: 10, or other BARA polypeptide. Fusions may be direct (with no linker or adapter molecule) or may be through a linker or adapter molecule. A linker or adapter molecule may be one or more amino acid residues, typically from about 20 to about 50 amino acid residues. A linker or adapter molecule may also be designed with a cleavage site in nucleic acid encoding the polypeptide for a DNA restriction endonuclease or for a protease cleavage site in the amino acid sequence that permits separation of the fused moieties. It will be appreciated that once constructed, the fusion polypeptides can be derivatized according to the methods described herein.

In a further embodiment of the invention, a polypeptide comprising the amino acid sequence of SEQ ID NO: 4, SEQ ID NO: 5, SEQ ID NO: 6, or SEQ ID NO: 10, or other BARA polypeptide, is fused to one or more domains of an Fc region of human IgG.

Antibodies comprise two functionally independent parts, a variable domain known as "Fab," that binds an antigen, and a constant domain known as "Fc," that is involved in effector functions such as complement activation and attack by phagocytic cells. An Fc fragment has a long serum half-life, whereas an Fab fragment is short-lived. Capon et al., 1989, Nature 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
| --- | --- | --- | --- |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590-600 |
| IgG1 | TNF receptor | septic shock | Fisher et al., 1996, N. Engl. J. Med. 334: 1697-1702; Van Zee et al., 1996, J. Immunol. 156: 2221-30 |

TABLE II-continued

Fc Fusion with Therapeutic Proteins

| Form of Fc | Fusion partner | Therapeutic implications | Reference |
|---|---|---|---|
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | International Pub. No. WO 97/23614 |
| IgG1 | N-terminus of leptin | anti-obesity | International Pub. No. WO 98/28427 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the amino-terminus or carboxyl-terminus of the BARA polypeptides using methods known to the skilled artisan. In another example, a human IgG hinge, CH2, and CH3 region may be fused at either the amino-terminus or carboxyl-terminus of a BARA polypeptide fragment.

The resulting BARA fusion polypeptide advantageously may be purified by use of a Protein A affinity column. Peptides and proteins fused to an Fc region have been found to exhibit a substantially greater half-life in vivo than the unfused counterpart. Also, a fusion to an Fc region permits dimerization/multimerization of the fusion polypeptide. As used for the fusion proteins disclosed herein, an Fc region may be a naturally occurring Fc region, or may be altered to improve certain qualities, such as therapeutic qualities, circulation time, or reduced aggregation.

Useful modifications of protein therapeutic agents by fusion with the "Fc" domain of an antibody are discussed in detail in U.S. patent application Ser. No. 09/428,082 (International Pub. No. WO 99/25044), which is hereby incorporated by reference in its entirety. That patent application discusses linkage to a "vehicle" such as polyethylene glycol (PEG), dextran, or an Fc region.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heijne, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., BLAST Manual (NCB NLM NIH, Bethesda, Md.); Altschul et al., 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;

Comparison matrix: BLOSUM 62 (Henikoff et al., supra);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, supra;

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

Nucleic acid molecules encoding a polypeptide comprising an amino acid sequence of a BARA polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides nucleic acid molecules as described herein and methods for obtaining such molecules.

Where a gene encoding an amino acid sequence of a BARA polypeptide has been identified from one species, all or a portion of that gene may be used as a probe to identify orthologs or related genes from the same species. Probes or primers may be used to screen cDNA libraries from various tissue sources believed to express the BARA polypeptide. In addition, part or all of a nucleic acid molecule having a sequence as set forth in SEQ ID NO: 1, SEQ ID NO: 2, SEQ ID NO: 3, or SEQ ID NO: 9 may be used to screen a genomic library to identify and isolate a gene encoding the amino acid sequence of a BARA polypeptide. Typically, conditions of moderate or high stringency will be employed for screening to minimize the number of false positives obtained from the screening.

Nucleic acid molecules encoding an amino acid sequence of BARA polypeptides may also be identified by expression cloning, which employs detection of positive clones based upon a property of an expressed protein. Typically, nucleic acid libraries are screened by binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes an amino acid sequence of a BARA polypeptide into an appropriate vector, one skilled in the art can readily produce large quantities of the desired nucleotide sequence. The sequences can then be used to generate detection probes or amplification primers. Alternatively, a polynucleotide encoding an amino acid sequence of a BARA polypeptide can be inserted into an expression vector. By introducing the expression vector into an appropriate host, the encoded BARA polypeptide may be produced in large amounts.

Another method for obtaining a suitable nucleic acid sequence is the polymerase chain reaction (PCR). In this method, cDNA is prepared from poly(A)$^+$ RNA or total RNA using the enzyme reverse transcriptase. Two primers, typically complementary to two separate regions of cDNA encoding the amino acid sequence of a BARA polypeptide, are then added to the cDNA along with a polymerase, preferably a thermostable polymerase such as Taq polymerase, and the polymerase amplifies the cDNA region between the two primers.

Another means of preparing a nucleic acid molecule encoding an amino acid sequence of a BARA polypeptide is chemical synthesis using methods well known to the skilled artisan, such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, DNA encoding an amino acid sequence of a BARA polypeptide will be several hundred nucleotides in length. Nucleic acids larger than about 100 nucleotides can be synthesized as several fragments using these methods. The fragments can then be ligated together to form the full-length nucleotide sequence of a BARA gene. Usually, the DNA fragment encoding the amino-terminus of the polypeptide will have an ATG, which encodes a methionine residue. This methionine may or may not be present on the mature form of the BARA polypeptide, depending on whether the polypeptide produced in the host cell is designed to be secreted from that cell. Other methods known to the skilled artisan may be used as well.

In certain embodiments, nucleic acid variants contain codons that have been altered for optimal expression of a BARA polypeptide in a given host cell. Particular codon alterations will depend upon the BARA polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "Drosophila_high.cod," "Human_high.cod," "Maize_high.cod," and "Yeast_high.cod."

In some cases, it may be desirable to prepare nucleic acid molecules encoding BARA polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding an amino acid sequence of a BARA polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding an amino acid sequence of a BARA polypeptide may be amplified/expressed in prokaryotic, yeast, insect (baculovirus systems) and/or eukaryotic host cells. Selection of the host cell will depend in part on whether a BARA polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the BARA polypeptide to be expressed, and a selectable marker element. Each of these sequences is discussed below.

The vector may also contain a "tag"-encoding sequence, i.e., an oligonucleotide molecule located at the 5' or 3' end of the BARA polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the BARA polypeptide from the host cell. Affinity purification can be accomplished, for example, by column chromatography using antibodies against the tag as an affinity matrix. Optionally, the tag can subsequently be removed from the purified BARA polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences that normally function to regulate BARA polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than BARA gene flanking sequences—will have been previously identified by mapping and/or by restriction endonuclease digestion and can thus be isolated from the proper tissue source using appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan.

The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a BARA polypeptide. If the vector of choice does not contain an origin of replication, one may be chemically synthesized based on a known sequence, and ligated into the vector. For example, the origin of replication from the plasmid pBR322 (New England Biolabs, Beverly, Mass.) is suitable for most gram-negative bacteria, and various virus-derived origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter), at least in part because the vectors do not replicate episomally in mammalian cells.

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in both prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase (TK), particularly promoterless embodiments of TK genes. Mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a BARA polypeptide. As a result, increased quantities of BARA polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a BARA polypeptide to be expressed. The consensus Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a BARA polypeptide out of the host cell. Typically, a nucleotide sequence encoding a signal sequence is positioned in the coding region of a BARA nucleic acid molecule, or directly at the 5' end of a BARA polypeptide coding region. Many signal sequences have been identified, and any of those that are functional in the selected host cell may be used in conjunction with a BARA nucleic acid molecule. Therefore, a signal sequence may be homologous (naturally occurring) or heterologous to the BARA nucleic acid molecule. Additionally, a signal sequence may be chemically synthesized using methods described herein. In most cases, the secretion of a BARA polypeptide from the host cell via the presence of a signal peptide will result in the removal of the signal peptide from the secreted BARA polypeptide. The signal sequence may be a component of the vector, or it may be a part of a BARA nucleic acid molecule that is inserted into the vector.

Included within the scope of this invention is the use of either a nucleotide sequence encoding a native BARA polypeptide signal sequence joined to a BARA polypeptide coding region or a nucleotide sequence encoding a heterologous signal sequence joined to a BARA polypeptide coding region. A heterologous signal sequence selected should be one that is recognized and processed, i.e., cleaved by a signal peptidase, by the host cell. For prokaryotic host cells that do not recognize and process the native BARA polypeptide signal sequence, the signal sequence is substituted by a prokaryotic signal sequence such as, for example, alkaline phosphatase, penicillinase, or heat-stable enterotoxin II leaders. For yeast secretion, a native BARA polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired BARA polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the BARA gene especially where the gene used is a full-length genomic sequence or a fragment thereof. Where the intron is not naturally occurring within the gene (as for most cDNAs), the intron may be obtained from another source. The position of the intron with respect to flanking sequences and the BARA gene is generally important, as the intron must be transcribed to be effective. Thus, when a BARA cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding a BARA polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to a nucleic acid encoding a BARA polypeptide by removing the promoter from the source DNA by restriction enzyme digestion and inserting the desired promoter sequence into the vector. The native BARA promoter sequence may be used to direct amplification and/or expression of a BARA nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling BARA gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto et al., 1980, *Cell* 22:787-97); the herpes thymidine kinase promoter (Wagner et al., 1981, *Proc. Natl. Acad. Sci. U.S.A.* 78:144445); the regulatory sequences of the metallothionine gene (Brinster et al., 1982, *Nature* 296:3942); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:63946; Ornitz et al., 1986, *Cold Spring Harbor Symp. Quant. Biol.* 50:399409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:143644); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-fetoprotein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a BARA polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a BARA nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pLXSN; pcDNA4-βgal; pIND-βgal; pCRII, pCR3, and pcDNA3.1 (Invitrogen, Carlsbad, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (International Pub. No. WO 90/14363) and pFastBacDual (Gibco-BRL, Grand Island, N.Y.).

Additional suitable vectors include, but are not limited to, cosmids, plasmids, or modified viruses, and preferably retroviruses, but it will be appreciated that the vector system must be compatible with the selected host cell. Such vectors include, but are not limited to plasmids such as Bluescript® plasmid derivatives (a high copy number ColE1-based phagemid; Stratagene Cloning Systems; La Jolla Calif.), PCR cloning plasmids designed for cloning Taq-amplified PCR products (e.g., TOPO™ TA Cloning® Kit, PCR2.1® plasmid derivatives; Invitrogen), and mammalian, yeast or virus vectors such as a baculovirus expression system (pBacPAK plasmid derivatives; Clontech; Palo Alto, Calif.).

After a vector has been constructed and a nucleic acid molecule encoding a BARA polypeptide has been inserted into the proper site of the vector, the completed vector may be inserted into a suitable host cell for amplification and/or polypeptide expression. Transformation of an expression vector for a BARA polypeptide into a selected host cell may be accomplished by well known methods including transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, vertebrate or mammalian cells). The host cell, when cultured under appropriate conditions, synthesizes a BARA polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, 3T3 cells, the osteosarcoma line U20S, rodent L-929 and Rat-1 cells, Hela cells, A549 cells, and PA317 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5a, DH10, and MC1061) are well-known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.*

4:564-72; and Lucklow et al., 1993, *J. Virol.,* 67:4566-79. Preferred insect cells are Sf-9 and Hi5 (Invitrogen).

One may also use transgenic animals to express glycosylated BARA polypeptides. For example, one may use a transgenic milk-producing animal (a cow or goat, for example) and obtain the present glycosylated polypeptide in the animal milk. One may also use plants to produce BARA polypeptides, however, in general, the glycosylation occurring in plants is different from that produced in mammalian cells, and may result in a glycosylated product which is not suitable for human therapeutic use.

Polypeptide Production

Host cells comprising a BARA polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a BARA polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a BARA polypeptide has been designed to be secreted from the host cells, the majority of polypeptide may be found in the cell culture medium. If however, the BARA polypeptide is not secreted from the host cells, it will be present in the cytoplasm and/or the nucleus (for eukaryotic host cells) or in the cytosol (for gram-negative bacteria host cells).

For a BARA polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a BARA polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized BARA polypeptide can then be analyzed using gel electrophoresis, immunoprecipitation, or the like. If it is desired to isolate a BARA polypeptide, isolation may be accomplished using standard methods such as those described herein and in Marston et al., 1990, *Meth. Enz.,* 182:264-75.

In some cases, a BARA polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a BARA polypeptide, then the polypeptide will be found primarily in the supernatant after centrifugation of the cell homogenate. The polypeptide may be further isolated from the supernatant using methods such as those described herein.

The purification of a BARA polypeptide from solution can be accomplished using a variety of techniques. If the polypeptide has been synthesized such that it contains a tag such as Hexahistidine (BARA polypeptide/hexaHis) or other small peptide such as FLAG (Eastman Kodak Co., New Haven, Conn.) or myc (Invitrogen) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of BARA polypeptide/polyHis. See, e.g., Current Protocols in Molecular Biology § 10.11.8 (Ausubel et al., eds., Green Publishers Inc. and Wiley and Sons 1993).

Additionally, BARA polypeptides may be purified through the use of a monoclonal antibody that is capable of specifically recognizing and binding to a BARA polypeptide. Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

BARA polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, Solid Phase Peptide Synthesis (Pierce Chemical Co. 1984). Such polypeptides may be synthesized with or without a methionine on the amino-terminus. Chemically synthesized BARA polypeptides may be oxidized using methods set forth in these references to form disulfide bridges. Chemically synthesized BARA polypeptides are expected to have comparable biological activity to the corresponding BARA polypeptides produced recombinantly or purified from natural sources, and thus may be used interchangeably with a recombinant or natural BARA polypeptide.

Another means of obtaining BARA polypeptide is via purification from biological samples such as source tissues and/or fluids in which BARA polypeptides are naturally found. Such purification can be conducted using methods for protein purification as described herein. The presence of the BARA polypeptide during purification may be monitored, for example, using an antibody prepared against recombinantly produced BARA polypeptide or peptide fragments thereof.

A number of additional methods for producing nucleic acids and polypeptides are known in the art, and the methods can be used to produce polypeptides having specificity for BARA polypeptide. See, e.g., Roberts et al., 1997, *Proc. Natl. Acad. Sci. U.S.A.* 94:12297-303, which describes production of fusion proteins between an mRNA and its encoded peptide. See also, Roberts, 1999, Curr. Opin. Chem. Biol. 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in International Pub. No. WO99/15650, the process involving activation of endogenous gene expression or overexpression of a gene by in situ recombination methods. For example, expression of an endogenous gene is activated or increased by integrating a regulatory sequence into the target cell that is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive BARA polypeptide expression libraries, which can subsequently be used for high throughput phenotypic screening in a variety of assays, such as biochemical assays, cellular assays, and whole organism assays (e.g., plant, mouse, etc.).

It will be appreciated by those skilled in the art that the nucleic acid and polypeptide molecules described herein may be produced by recombinant genetic and other means known to those with skill in the art.

Selective Binding Agents

The term "selective binding agent" refers to a molecule that has specificity for one or more BARA polypeptides. Suitable selective binding agents include, but are not limited to, antibodies and derivatives thereof, polypeptides, and small molecules. Suitable selective binding agents may be prepared using methods known in the art. An exemplary BARA polypeptide selective binding agent of the present invention is capable of binding a certain portion of the BARA polypeptide thereby inhibiting the binding of the polypeptide to a BARA polypeptide receptor.

Selective binding agents such as antibodies and antibody fragments that bind BARA polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the BARA polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a BARA polypeptide generally are produced in animals (e.g., rabbits or mice) by means of multiple subcutaneous or intraperitoneal injections of BARA polypeptide and an adjuvant. It may be useful to conjugate a BARA polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response.

After immunization, the animals are bled and the serum is assayed for anti-BARA antibody titer.

Monoclonal antibodies directed toward BARA polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with BARA polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind BARA polypeptides. Using transgenic animals (e.g., mice) that are capable of producing a repertoire of human antibodies in the absence of endogenous immunoglobulin production such antibodies are produced by immunization with a BARA polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is animals having less than the full complement of modifications, are then crossbred to obtain an animal having all of the desired immune system modifications. When administered an immunogen, these transgenic animals produce antibodies with human (rather than, e.g., murine) amino acid sequences, including variable regions that are immunospecific for these antigens. See International Pub. Nos. WO 96/33735 and WO 94/02602. Additional methods are described in U.S. Pat. No. 5,545,807, International Pub. Nos. WO 91/10741 and WO 90/04036, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in International Pub. No. WO 99/10494, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-BARA antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of BARA polypeptides. The antibodies will bind BARA polypeptides with an affinity that is appropriate for the assay method being employed.

For diagnostic applications, in certain embodiments, anti-BARA antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., 1990, *Meth. Enz.* 184:138-63).

Competitive binding assays rely on the ability of a labeled standard (e.g., a BARA polypeptide, or an immunologically reactive portion thereof) to compete with the test sample analyte (an BARA polypeptide) for binding with a limited amount of anti-BARA antibody. The amount of a BARA polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-BARA antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally antagonists or, preferably, agonists, in that they either reduce or enhance, respectively, at least one of the biological activities of a BARA polypeptide. Selective binding agents, including agonist and antagonist anti-BARA polypeptide antibodies, are identified by screening assays that are well known in the art.

The invention also relates to a kit comprising BARA selective binding agents (such as antibodies) and other reagents useful for detecting BARA polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the BARA molecules of the invention, including, but not limited to: identification and validation of BARA disease-related genes as targets for therapeutics; molecular toxicology of related BARA molecules and inhibitors thereof; stratification of populations and generation of surrogate markers for clinical trials; and enhancing related BARA polypeptide small molecule drug discovery by aiding in the identification of selective compounds in high throughput screens.

Chemical Derivatives

Chemically modified derivatives of BARA polypeptides may be prepared by one skilled in the art, given the disclosures described herein. BARA polypeptide derivatives are modified in a manner that is different—either in the type or location of the molecules naturally attached to the polypeptide. Derivatives may include molecules formed by the deletion of one or more naturally-attached chemical groups. The polypeptide comprising an amino acid sequence of SEQ ID NO: 4, SEQ ID NO: 5, SEQ ID NO: 6, or SEQ ID NO: 10, or other BARA polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that may be used to prepare covalently attached BARA polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of SEQ ID NO: 4, SEQ ID NO: 5, SEQ ID NO: 6, or SEQ ID NO: 10, or other BARA polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the BARA polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, BARA polypeptides may be chemically coupled to biotin. The biotin/BARA polypeptide molecules are then allowed to bind to avidin, resulting in tetravalent avidin/biotin/BARA polypeptide molecules. BARA polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present BARA polypeptide derivatives include those described herein for BARA polypeptides. However, the BARA polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native BARA polypeptide have been disrupted (i.e., "knocked out") such that the level of expression of BARA polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a BARA gene for that animal or a heterologous BARA gene is over-expressed by the animal, thereby creating a "transgenic" animal. Such transgenic animals may be prepared using well known methods such as those described in U.S. Pat. No. 5,489,743 and International Pub. No. WO 94/28122.

The present invention further includes non-human animals in which the promoter for one or more of the BARA polypeptides of the present invention is either activated or inactivated (e.g., by using homologous recombination methods) to alter the level of expression of one or more of the native BARA polypeptides.

These non-human animals may be used for drug candidate screening. In such screening, the impact of a drug candidate on the animal may be measured. For example, drug candidates may decrease or, preferably, increase the expression of the BARA gene. In certain embodiments, the amount of BARA polypeptide that is produced may be measured after the exposure of the animal to the drug candidate. Additionally, in certain embodiments, one may detect the actual impact of the drug candidate on the animal. For example, inadequate expression of a particular gene, for example the BARA gene, may result in, or be associated with, a disease or pathological condition. In such cases, one may test a drug candidate's ability to increase expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Modulators of BARA Polypeptide Activity

In some situations, it may be desirable to identify molecules that are modulators, i.e., agonists or antagonists, of the activity of BARA polypeptide. Natural or synthetic molecules that modulate BARA polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a BARA polypeptide. Most commonly, a test molecule will interact directly with a BARA polypeptide. However, it is also contemplated that a test molecule may also modulate BARA polypeptide activity indirectly, such as by affecting BARA gene expression, or by binding to a BARA polypeptide binding partner (e.g., receptor or ligand). In one embodiment, a test molecule will bind to a BARA polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with BARA polypeptides are encompassed by the present invention. In certain embodiments, a BARA polypeptide is incubated with a test molecule under conditions that permit the interaction of the test molecule with a BARA polypeptide, and the extent of the interaction is measured. The test molecule can be screened in a substantially purified form or in a crude mixture.

In certain embodiments, a BARA polypeptide agonist or antagonist may be a protein, peptide, carbohydrate, lipid, or small molecular weight molecule that interacts with BARA polypeptide to regulate its activity. Molecules which regulate BARA polypeptide expression include nucleic acids which are complementary to nucleic acids encoding a BARA polypeptide, or are complementary to nucleic acids sequences which direct or control the expression of BARA polypeptide, and which act as anti-sense regulators of expression.

Once a test molecule has been identified as interacting with a BARA polypeptide, the molecule may be further evaluated for its ability to increase or decrease BARA polypeptide activity. The measurement of the interaction of a test molecule with BARA polypeptide may be carried out in several formats, including cell-based binding assays, membrane binding assays, solution-phase assays, and immunoassays. In general, a test molecule is incubated with a BARA polypeptide for a specified period of time, and BARA polypeptide activity is determined by one or more assays for measuring biological activity.

The interaction of test molecules with BARA polypeptides may also be assayed directly using polyclonal or monoclonal antibodies in an immunoassay. Alternatively, modified forms of BARA polypeptides containing epitope tags as described herein may be used in solution and immunoassays.

In the event that BARA polypeptides display biological activity through an interaction with a binding partner (e.g., a receptor or a ligand), a variety of in vitro assays may be used to measure the binding of a BARA polypeptide to the corresponding binding partner (such as a selective binding agent, receptor, or ligand). These assays may be used to screen test molecules for their ability to increase or decrease the rate and/or the extent of binding of a BARA polypeptide to its binding partner. In one assay, a BARA polypeptide is immobilized in the wells of a microtiter plate. Radiolabeled BARA polypeptide binding partner (for example, iodinated BARA polypeptide binding partner) and a test molecule can then be added either one at a time (in either order) or simultaneously to the wells. After incubation, the wells can be washed and counted for radioactivity, using a scintillation counter, to determine the extent to which the binding partner bound to the BARA polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing BARA polypeptide binding partner to the microtiter plate wells, incubating with the test molecule and radiolabeled BARA polypeptide, and determining the extent of BARA polypeptide binding. See, e.g., *Current Protocols in Molecular Biology*, chap. 18 (Ausubel et al., eds., Green Publishers Inc. and Wiley and Sons 1995).

As an alternative to radiolabeling, a BARA polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a BARA polypeptide or to a BARA polypeptide binding partner, and which is conjugated to biotin, may also be used for purposes of detection following incubation of the complex with enzyme-linked streptavidin linked to AP or HRP.

A BARA polypeptide or a BARA polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a BARA polypeptide and its binding partner can be assessed using the methods described herein. Alternatively, the substrate-protein complex can be immobilized in a column with the test molecule and complementary protein passing through the column. The formation of a complex between a BARA polypeptide and its binding partner can then be assessed using any of the techniques described herein (e.g., radiolabeling or antibody binding).

Another in vitro assay that is useful for identifying a test molecule that increases or decreases the formation of a complex between a BARA polypeptide binding protein and a BARA polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either BARA polypeptide or a BARA polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a BARA polypeptide and a BARA polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a BARA polypeptide and BARA polypeptide binding partner. The assays may be automated to screen compounds generated in phage display, synthetic peptide, and chemical synthesis libraries.

Compounds which increase or decrease the formation of a complex between a BARA polypeptide and a BARA polypeptide binding partner may also be screened in cell culture using cells and cell lines expressing either BARA polypeptide or BARA polypeptide binding partner. Cells and cell lines may be obtained from any mammal, but preferably will be from human or other primate, canine, or rodent sources. The binding of a BARA polypeptide to cells expressing BARA polypeptide binding partner at the surface is evaluated in the presence or absence of test molecules, and the extent of binding may be determined by, for example, flow cytometry using a biotinylated antibody to a BARA polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the BARA gene. In certain embodiments, the amount of BARA polypeptide or a BARA polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 8) of the HIV tat protein (termed the "protein transduction domain," or TAT PTD) has been described as mediating delivery across the cytoplasmic membrane and the nuclear membrane of a cell. See Schwarze et al., 1999, *Science* 285:1569-72; and Nagahara et al., 1998, *Nat Med.* 4:1449-52. In these procedures, FITC-constructs (FITC-labeled G-G-G-G-Y-G-R-K-K-R-R-Q-R-R-R; SEQ ID NO: 7), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a BARA antagonist (such as an anti-BARA selective binding agent, small molecule, soluble receptor, or antisense oligonucleotide) can be administered intracellularly to inhibit the activity of a BARA molecule. As used herein, the term "BARA molecule" refers to both BARA nucleic acid molecules and BARA polypeptides as defined herein. Where desired, the BARA protein itself may also be internally administered to a cell using these procedures. See also, Straus, 1999, *Science* 285:1466-67.

Cell Source Identification Using BARA Polypeptide

In accordance with certain embodiments of the invention, it may be useful to be able to determine the source of a certain cell type associated with a BARA polypeptide. For example, it may be useful to determine the origin of a disease or pathological condition as an aid in selecting an appropriate therapy. In certain embodiments, nucleic acids encoding a BARA polypeptide can be used as a probe to identify cells described herein by screening the nucleic acids of the cells with such a probe. In other embodiments, one may use anti-BARA polypeptide antibodies to test for the presence of BARA polypeptide in cells, and thus, determine if such cells are of the types described herein.

BARA Polypeptide Compositions and Administration

Therapeutic compositions are within the scope of the present invention. Such BARA polypeptide pharmaceutical compositions may comprise a therapeutically effective amount of a BARA polypeptide or a BARA nucleic acid molecule in admixture with a pharmaceutically or physiologically acceptable formulation agent selected for suitability with the mode of administration. Pharmaceutical compositions may comprise a therapeutically effective amount of one or more BARA polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the BARA molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute.

In one embodiment of the present invention, BARA polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the BARA polypeptide product may be formulated as a lyophilizate using appropriate excipients such as sucrose.

The BARA polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired BARA molecule in a pharmaceutically acceptable vehicle. A particularly suitable vehicle for parenteral injection is sterile distilled water in which a BARA molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, BARA polypeptide may be formulated as a dry powder for inhalation. BARA polypeptide or nucleic acid molecule inhalation solutions may also be formulated with a propellant for aerosol delivery. In yet another embodiment, solutions may be nebulized. Pulmonary administration is further described in International Pub. No. WO 94/20069, which describes the pulmonary delivery of chemically modified proteins.

It is also contemplated that certain formulations may be administered orally. In one embodiment of the present invention, BARA polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the BARA polypeptide. Diluents, flavorings, low melting point waxes, vegetable oils, lubricants, suspending agents, tablet disintegrating agents, and binders may also be employed.

Another pharmaceutical composition may involve an effective quantity of BARA polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional BARA polypeptide pharmaceutical compositions will be evident to those skilled in the art, including formulations involving BARA polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., International Pub. No. WO 93/15722, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(-)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The BARA pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a BARA pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the BARA molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the BARA molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use BARA polypeptide pharmaceutical compositions in an ex vivo manner. In such instances, cells, tissues, or organs that have been removed from the patient are exposed to BARA polypeptide pharmaceutical compositions after which the cells, tissues, or organs are subsequently implanted back into the patient.

In other cases, a BARA polypeptide can be delivered by implanting certain cells that have been genetically engineered, using methods such as those described herein, to express and secrete the BARA polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more BARA polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent BARA gene, or an under-expressed gene, and thereby produce a cell which expresses therapeutically efficacious amounts of BARA polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; and International Pub. Nos. WO 91/09955 and WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a BARA polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired BARA polypeptide. The control element controls a portion of the DNA present in the host cell genome. Thus, the expression of the desired BARA polypeptide may be achieved not by transfection of DNA that encodes the BARA gene itself, but rather by the use of targeting DNA (containing regions of homology with the endogenous gene of interest) coupled with DNA regulatory segments that provide the endogenous gene sequence with recognizable signals for transcription of a BARA gene.

In an exemplary method, the expression of a desired targeted gene in a cell (i.e., a desired endogenous cellular gene) is altered via homologous recombination into the cellular genome at a preselected site, by the introduction of DNA that includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, BARA polypeptide production from a cell's endogenous BARA gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic BARA polypeptide coding region. A plasmid containing a recombination site homologous to the site that was placed just upstream of the genomic BARA polypeptide coding region is introduced into the modified cell line along with the appropriate recombinase enzyme. This recombinase causes the plasmid to integrate, via the plasmid's recombination site, into the recombination site located just upstream of the genomic BARA polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased BARA polypeptide production from the cell's endogenous BARA gene.

A further method to use the cell line in which the site specific recombination sequence had been placed just upstream of the cell's endogenous genomic BARA polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol.*, 225:890-900) that would create a new or modified transcriptional unit resulting in de novo or increased BARA polypeptide production from the cell's endogenous BARA gene.

An additional approach for increasing, or causing, the expression of BARA polypeptide from a cell's endogenous BARA gene involves increasing, or causing, the expression of a gene or genes (e.g., transcription factors) and/or decreasing the expression of a gene or genes (e.g., transcriptional repressors) in a manner which results in de novo or increased BARA polypeptide production from the cell's endogenous BARA gene. This method includes the introduction of a non-naturally occurring polypeptide (e.g., a polypeptide comprising a site specific DNA binding domain fused to a transcriptional factor domain) into the cell such that de novo or increased BARA polypeptide production from the cell's endogenous BARA gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of BARA polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a BARA polypeptide, which nucleotides may be used as targeting sequences.

BARA polypeptide cell therapy, e.g., the implantation of cells producing BARA polypeptides, is also contemplated. This embodiment involves implanting cells capable of synthesizing and secreting a biologically active form of BARA polypeptide. Such BARA polypeptide-producing cells can be cells that are natural producers of BARA polypeptides or may be recombinant cells whose ability to produce BARA polypeptides has been augmented by transformation with a gene encoding the desired BARA polypeptide or with a gene augmenting the expression of BARA polypeptide. Such a modification may be accomplished by means of a vector suitable for delivering the gene as well as promoting its expression and secretion. In order to minimize a potential immunological reaction in patients being administered a BARA polypeptide, as may occur with the administration of a polypeptide of a foreign species, it is preferred that the natural cells producing BARA polypeptide be of human origin and produce human BARA polypeptide. Likewise, it is preferred that the recombinant cells producing BARA polypeptide be transformed with an expression vector containing a gene encoding a human BARA polypeptide.

Implanted cells may be encapsulated to avoid the infiltration of surrounding tissue. Human or non-human animal cells may be implanted in patients in biocompatible, semipermeable polymeric enclosures or membranes that allow the release of BARA polypeptide, but that prevent the destruction of the cells by the patient's immune system or by other detrimental factors from the surrounding tissue. Alternatively, the patient's own cells, transformed to produce BARA polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (International Pub. No. WO 95/05452 and International Pub. No. WO 95/05452) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in International Pub. No. WO 91/10425 (Aebischer et al.). See also, International Pub. No. WO 91/10470 (Aebischer et al.); Winn et al., 1991, *Exper. Neurol.* 113:322-29; Aebischer et al., 1991, *Exper. Neurol* 111:269-75; and Tresco et al., 1992, *ASAIO* 38:17-23.

In vivo and in vitro gene therapy delivery of BARA polypeptides is also envisioned. One example of a gene therapy technique is to use the BARA gene (either genomic DNA, cDNA, and/or synthetic DNA) encoding a BARA polypeptide that may be operably linked to a constitutive or inducible promoter to form a "gene therapy DNA construct." The promoter may be homologous or heterologous to the endogenous BARA gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the BARA gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see International Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and International Pub. Nos. WO 96/40911 and WO 97/10337.

Yet another control system uses ecdysone (a fruit fly steroid hormone) that binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and International Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding BARA polypeptide into cells via local injection of a BARA nucleic acid molecule or by other appropriate viral or non-viral delivery vectors. Hefti 1994, Neurobiology 25:1418-35. For example, a nucleic acid molecule encoding a BARA polypeptide may be contained in an adeno-associated virus (MV) vector for delivery to the targeted cells (see, e.g., International Pub. Nos. WO 95/34670 and WO 95/34670). The recombinant MV genome typically contains MV inverted terminal repeats flanking a DNA sequence encoding a BARA polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and International Pub. No. WO 96/40958 (involving nuclear ligands).

It is also contemplated that BARA gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous BARA polypeptide expression in a cell via gene therapy is to insert one or more enhancer elements into the BARA polypeptide promoter, where the enhancer elements can serve to increase transcriptional activity of the BARA gene. The enhancer elements used will be selected based on the tissue in which one desires to activate the gene—enhancer elements known to confer promoter activation in that tissue will be selected. For example, if a gene encoding a BARA polypeptide is to be "turned on" in T-cells, the Ick promoter enhancer element may be used. Here, the functional portion of the transcriptional element to be added may be inserted into a fragment of DNA containing the BARA polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease BARA polypeptide expression by modifying the nucleotide sequence of the endogenous promoter. Such modification is typically accomplished via homologous recombination methods. For example, a DNA molecule containing all or a portion of the promoter of the BARA gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding BARA gene. The deletion of the TATA box or the transcription activator binding site in the promoter may be accomplished by generating a DNA construct comprising all or the relevant portion of the BARA polypeptide promoter (from the same or a related species as the BARA gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

BARA nucleic acid molecules, polypeptides, and agonists and antagonists thereof can be used to treat, ameliorate, or prevent diseases, disorders, or conditions related to the proliferation of cells, including those recited herein.

BARA polypeptide antagonists and agonists include those molecules which regulate BARA polypeptide activity and either decrease or increase at least one activity of the mature form of the BARA polypeptide. Agonists or antagonists may be co-factors, such as a protein, peptide, carbohydrate, lipid, or small molecular weight molecule, which interact with BARA polypeptide and thereby regulate its activity. Potential polypeptide agonists or antagonists include antibodies that react with BARA polypeptides of the invention.

BARA polypeptides play a role in the control of apoptosis and senescence, i.e., cell death, and can exert such effects on neoplastic cells. Accordingly, BARA nucleic acid molecules, polypeptides, and agonists thereof may be useful for the treatment or diagnosis of diseases involving uncontrolled cellular proliferation. Examples of such diseases include, but are not limited to, malignant or benign examples of: bone cancers, brain tumors, breast cancer, endocrine system cancers, gastrointestinal cancers, gynecologic cancers, head and neck cancers, leukemia, lung cancers, lymphomas, myelomas, pediatric cancers, penile cancer, prostate cancer, sarcomas, skin cancers, testicular cancer, thyroid cancer, and urinary tract cancers. Other proliferative diseases are encompassed within the scope of the invention.

Antagonists or agonists of BARA polypeptide function may be used (simultaneously or sequentially) in combination with one or more cytokines, growth factors, antibiotics, anti-inflammatories, and/or chemotherapeutic agents as is appropriate for the condition being treated.

The ability of BARA to induce p53, and perhaps other targets that decrease cell proliferation and induce senescence apoptosis/cells death, can be used to screen for proteins that inhibit the induction of p53 through BARA. These proteins will be potential therapeutic targets because their inhibition will result in an increase in p53 with the consequent effects on senescence, apoptosis/cell death and/or cell proliferation. Further, since BARA associates with the type I interferon receptor β chain, it may have antiviral effects by itself or increase the antiviral response of cells to type I interferon (IFN) treatment.

Other diseases or disorders caused by or mediated by undesirable levels of BARA polypeptides are encompassed within the scope of the invention. Undesirable levels include excessive levels of BARA polypeptides and sub-normal levels of BARA polypeptides.

Diagnostic and Other Uses of BARA Nucleic Acids and Polypeptides

BARA nucleic acid molecules (including those that do not themselves encode biologically active polypeptides), may be useful as hybridization probes in diagnostic assays to test, either qualitatively or quantitatively, for the presence of a BARA nucleic acid molecule in mammalian tissue or bodily fluid samples.

Since BARA plays a role in senescence and apoptosis, different types of cancers may have alteration of the BARA gene such as: (i) mutations in its protein coding or non-coding region (regulatory regions such as promoter, introns, 3' and 5' untranslated region, etc), (ii) deletions of one or both alleles, (iii) promoter silencing due to methylation, and (iv) chromosomal translocations that involve the BARA locus. Detection of these alterations by methods such as, but not limited to, PCR and Southern blot analysis can utilize BARA nucleic acid sequences. Additionally, diseases that involved accelerated cell death such as many degenerative diseases of the central and peripheral nervous system, β-cell of the pancreas in diabetes mellitus, and others can have increased levels of expression of the BARA protein due to amplification of the BARA gene. Amplification of the BARA gene can be detected using PCR and other methods that require BARA nucleic acid sequences.

Other methods may also be employed where it is desirable to enhance the activity of one or more BARA polypeptides. Such enhancement may be effected the introduction of BARA nucleic acids, under the control of endogenous or exogenous transcription control sequences, into the affected cells or tissue by, for example, gene therapy techniques. For example, the DNA encoding a BARA polypeptide can be prepared and introduced into the cells of a patient using either viral or non-viral methods as described herein. Each such exogenous BARA nucleic acid is designed to be transcribed by the cellular machinery, which then increases the amount of active BARA in the target cells. Consequently, BARA activity increases in the target cells.

In addition, a BARA polypeptide, whether biologically active or not, may be used as an immunogen, that is, the polypeptide contains at least one epitope to which antibodies may be raised. Selective binding agents that bind to a BARA polypeptide (as described herein) may be used for in vivo and in vitro diagnostic purposes, including, but not limited to, use in labeled form to detect the presence of BARA polypeptide in a body fluid or cell sample. The antibodies may also be used to diagnose a number of diseases and disorders, including those recited herein. While antibodies may bind to a BARA polypeptide so as to diminish or block at least one activity characteristic of a BARA polypeptide, generally a greater amount of wild type BARA activity, with its consequent suppression of cellular proliferation, is desired.

BARA polypeptides can be used to clone BARA ligands using an "expression cloning" strategy. Radiolabeled ($^{125}$Iodine) BARA polypeptide or "affinity/activity-tagged" BARA polypeptide (such as an Fc fusion or an alkaline phosphatase fusion) can be used in binding assays to identify a cell type, cell line, or tissue that expresses a BARA ligand. RNA isolated from such cells or tissues can then be converted to cDNA, cloned into a mammalian expression vector, and transfected into mammalian cells (e.g., COS or 293) to create an expression library. Radiolabeled or tagged BARA polypeptide can then be used as an affinity reagent to identify and isolate the subset of cells in this library expressing a BARA ligand. DNA is then isolated from these cells and transfected into mammalian cells to create a secondary expression library in which the fraction of cells expressing the BARA ligand would be many-fold higher than in the original library. This enrichment process can be repeated iteratively until a single recombinant clone containing the BARA ligand is isolated. Isolation of BARA ligands is useful for identifying or developing novel agonists and antagonists of the BARA signaling pathway. Such agonists and antagonists include BARA ligands, anti-BARA ligand antibodies, small molecules or antisense oligonucleotides.

The following examples are intended for illustration purposes only, and should not be construed as limiting the scope of the invention in any way.

EXAMPLE 1

Cloning of Human and Mouse lin-9/BARA

Generally, materials and methods as described in Sambrook et al. supra were used to clone and analyze the genes encoding human and murine BARA polypeptides.

Although the Jak-Stat pathway is required for the antiviral and antiproliferative effects of IFNs, other pathways also contribute to these effects. The most significant example is the P13K pathway whose activation contributes to the antiviral effect through the induction of cell survival of the infected cells. To find new pathways directly activated by the IFNαR, a two-hybrid system screening using as bait the entire cytoplasmic domains of the α and βL subunits of the receptor were performed. The entire cytoplasmic domains of the human α (aa 465-557) and βL chains (aa 265-515) were fused to the GAL4 activating domain and used to screen a human lymphocyte cDNA library fused to the GAL4 activation domain (pACT vector, Clonetech). No true interactions were isolated when the α chain was used as bait, while three clones that corresponded to true interactions were isolated using the IFNαRβL chain. Clone 16 was particularly interesting due to its homology with the C-terminal region of the *C. elegans* LIN-9 protein. *C. elegans* LIN-9 is part of a negative regulatory pathway that includes the tumor suppressor gene retinoblastoma (RB), suggesting that human LIN-9 may contribute to the growth inhibitory effect of type I IFNs. The human homolog of *C. elegans* LIN-9 was later designated as β-subunit Associated Regulator of Apoptosis, or BARA, due to its effect on cell survival.

Figure 6:
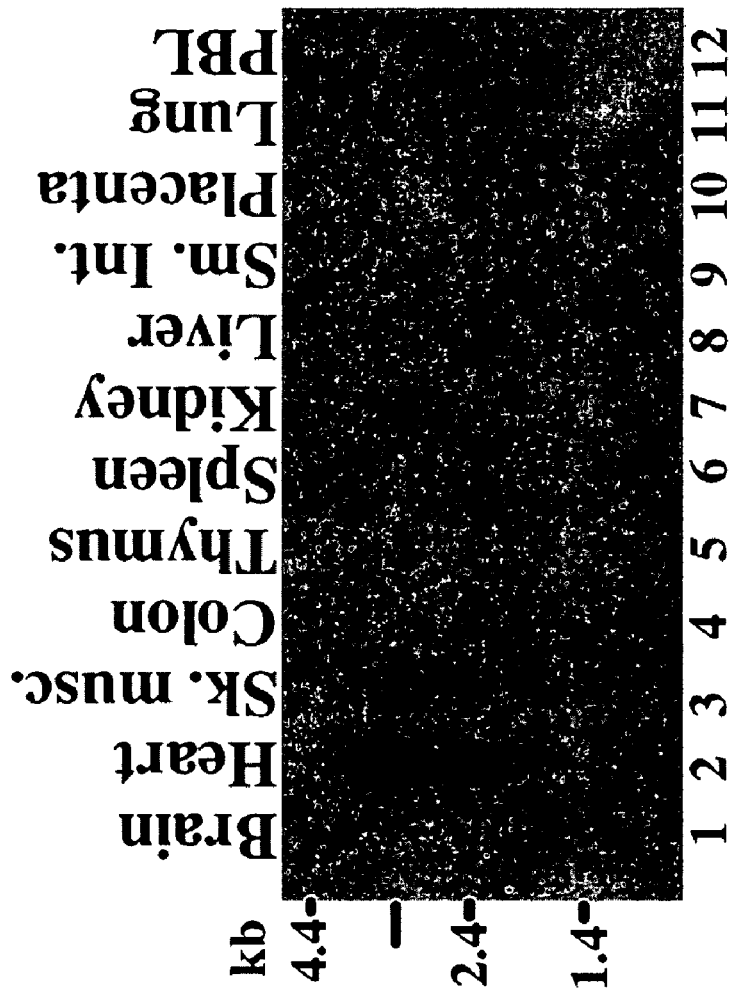
FIG. 6 shows a Northern blot of different tissues used to study the expression of BARA/LIN9.

Since clone 16 did not have a start codon and was shorter than the mRNA observed in Northen blots, human (U266 myeloma cell) and mouse (fibroblast) cDNA libraries were screened to obtain full-length cDNAs encoding the human and murine BARA. Nine human and 2 mouse cDNA clones were obtained out of a total of about $3\times10^6$ and $1\times10^6$ screened, respectively. Four of the clones for human BARA contained inserts of almost 3 kb, which were close to the predicted size for the human transcript as determined by Northern blot analysis (FIG. 6). The remaining clones contained shorter inserts of approximately 1.6 kb probably originated by internal priming since no transcripts of this size were detected. A single 3.0-3.1 kb transcript for human BARA (huBARA; human LIN9/BARA) in human multiple tissue Northern blot was detected (FIG. 6). The highest expression was observed in heart and skeletal muscle, while lower levels, evident in long exposures of the autoradiograms, were present in colon, thymus, spleen, kidneys, liver, small intestine, placenta, lung and peripheral blood. Brain did not show detectable transcripts.

The four 3 kb inserts encoded two splice variants of huBARA/lin-9 that were identified as huBARA short and long (huBARA-S and huBARA-L, respectively). 5' RACE yielded only 20 more nucleotides upstream of the previous sequence, resulting in a total of 3005 nucleotides for the huBARA-L cDNA. A search of the Human Genome Project Database identified a BAC clone (BAC-RP11-588H15) mapped to human chromosome 1q41-1q42, which contained the whole huBARA gene. There are 3 polyadenylation signals at positions 2264, 2806 and 2984 of the human cDNAs. The latter is 16 nucleotides from the polyA tail found in the long cDNAs.

The predicted protein product for huBARA-L, using the ATG in position +34 of the cDNA as a translation initiation site, is 541 amino acids long, highly basic (PI=9.37) and has a predicted molecular mass of 61,906 Daltons. The huBARA-S protein lacks exon 4, which encodes residues 54-88, and therefore, is 35 amino acids shorter (FIG. 7, double headed arrow indicates the residues absent in the short form).

Figure 7:
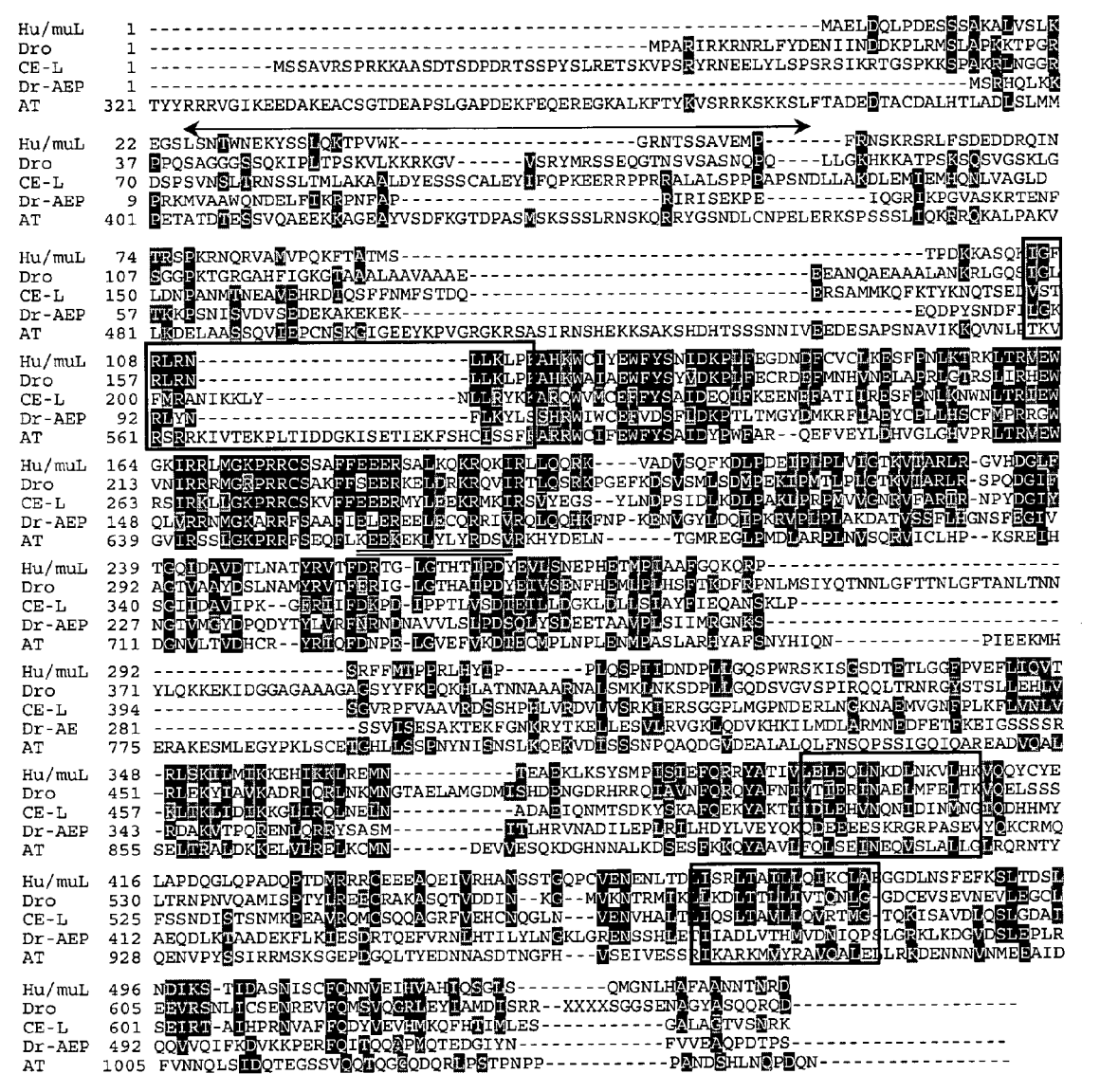

The human and murine proteins differ by only 12 amino acids, 11 of which are conserved substitutions. FASTA searches of databases with the human and murine BARA proteins revealed homology with a previously reported family of proteins which include two *D. Melanogaster* proteins 86E4.4 (35%, accession number 046093) and Always Early Protein (AEP, 21.2%) (42), *C. elegans* LIN-9 (30.9% with the long form, accession number MF76192, (43), *Arabidopsis Thaliana* (22.3%, accession number BAB03055) and *Saccharomyces cerevisiae* (17.9%, acces. number Q12481) (42, 43). A nuclear localization signal (NLS) (FIG. 7, KPRR starting at position 172 of the human sequence) appears to be conserved in all members of this family. There are three leucine rich regions that may correspond to putative nuclear export signals (NES) at positions 105-115, 392407, and 462475 (FIG. 7 Boxes), and a cyclin destruction box (CDB) (FIG. 7, residues 258-264, double line). The CDB is highly homologous to the consensus for cyclins A and B (44). Using the computer program Block Maker (Baylor College of Medicine Launcher), 7 blocks that are conserved in the different homologs were identified (M correspond to huBARA: block 1 AA53-62; block 2 AA108-153; block 3 AA148-179; block 4 AA209-240; block 5 AA337-371; block 6 AA384-414; and block 7 AA417-425). No other functional motifs are present in human or murine BARA.

EXAMPLE 2

Expression of Endogenous BARA/LIN9 mRNA

The β-chain Associated Regulator of Apoptosis gene encodes a protein that interacts with the β chain of the Interferon α receptor. However, further characterization of BARA indicated that it also has interferon-independent functions. A single 3.0-3.1 kb transcript for huBARA was detected in 11 of 12 samples of human multiple tissue Northern blot (FIG. 6). The highest expression was observed in heart and skeletal muscle, while lower levels were present in colon, thymus, spleen, kidneys, liver, small intestine, and placenta. Expression in lung and peripheral blood was barely detectable in long exposures of the autoradiograms (data not shown). Brain tissue appeared to be negative.

EXAMPLE 3

Expression of Endogenous BARA/LIN9 Protein

Figure 9:
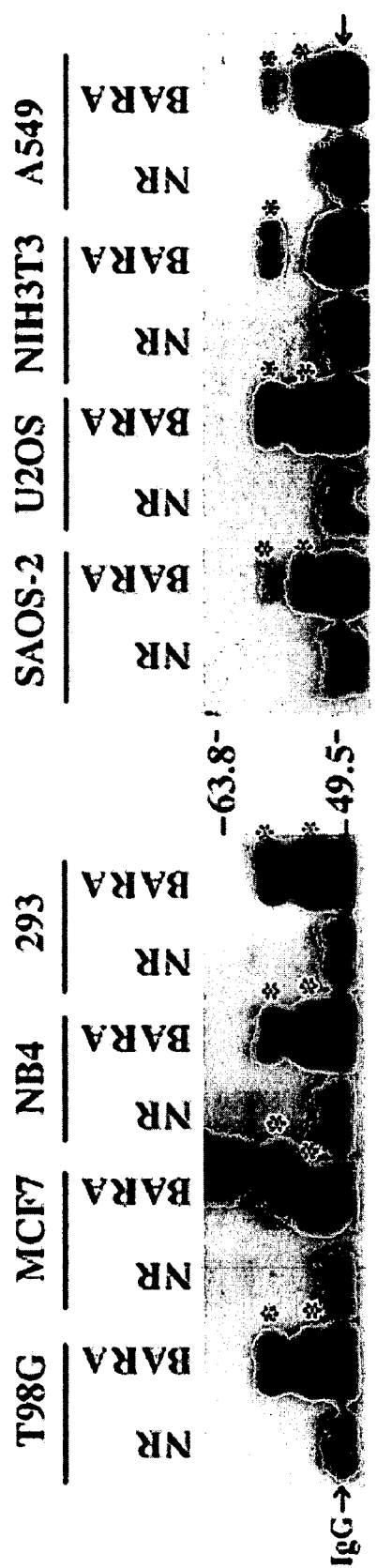
FIG. 9 shows the expression of BARA in different cell lines. Immunoprecipitation assays (IPs) were performed with an anti-BARA serum or normal rabbit control (NR) followed by western blot analysis (WB) with mAb#6. The migration of BARA-L and -S is indicated with asterisks. Arrows indicate the heavy chain of IgG.

The expression of BARA in different cell lines was investigated using two monoclonal antibodies (mAbs) that allow us to discriminate between long and short-for BARA and IgG, which migrates closely to the forms of BARA. One of these mAbs (mAb#1) recognizes an epitope within exon 4 and therefore, it only detects BARA-L, while mAb#6 recognizes both forms of the BARA protein (data not shown). A deposit of the hybridoma cell line that produces mAb#6 was made with the American Type Culture Collection (ATCC, Manassas, Va.) on May 9, 2003 under the terms of the Budapest Treaty. The deposited hybridoma cell line has been assigned Patent Deposit Number PTA-5191. Immunoprecipitation with a polyclonal sera followed by Western blotting with mAb#6 allowed us to identify the long and short forms of BARA (FIG. 9, asterisks), even though the short form migrates very close to the heavy chain of the IgG (FIG. 9, arrow). Most cell lines studied express equivalent amount of BARA-L and BARA-S with the exceptions of A549 and SAOS-2 that express higher levels of BARA-S and NIH3T3, which does express detectable amount of BARA-S. Other murine lines such as L929 and PA317 expressed equivalent amount of the long and short forms.

EXAMPLE 4

BARA Interacts with IFNαRβL

Figure 8:
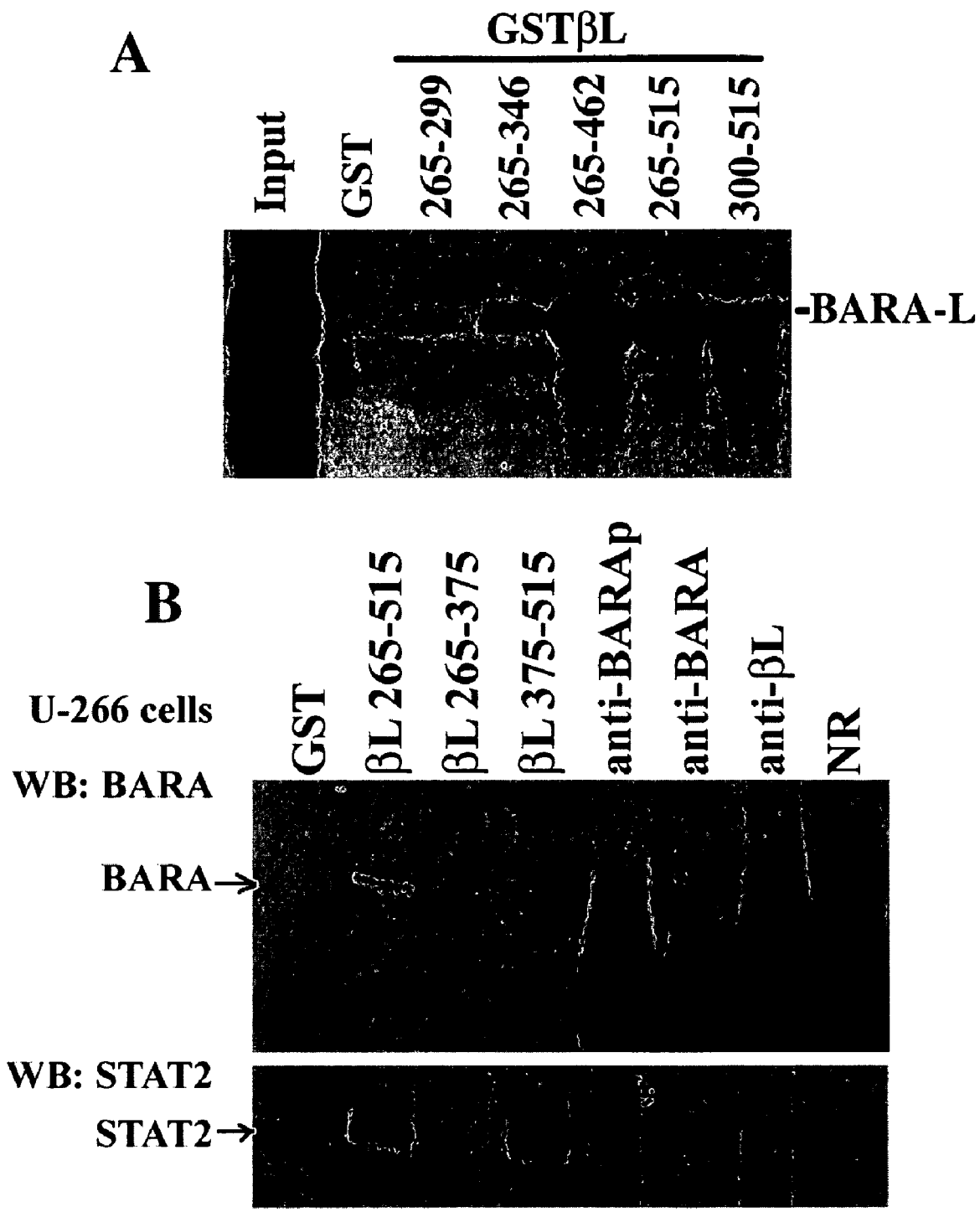
FIG. 8 shows pull-down assays performed with GST fusion proteins encoding the different regions of the cytoplasmic domain of IFNαRβL and in vitro translated BARA-L (A) or cell lysates (B, U266 cells) as a source for BARA. Note that although the 375-515 construct does not interact with BARA it still interacts with STAT2 (bottom panel).

To confirm that BARA interacts with the IFNαR, pull-down experiments using GST fusion proteins encoding different regions of the cytoplasmic of βL were performed. FIG. 8A shows that GST fusion proteins containing the full-length cytoplasmic domain (265-515), and with deletions of the first 35 (300-515) or last 53 (265462) amino acids interact with BARA. However, a GST fusion protein encoding residues 265-346 bound significantly lower amounts of BARA-L, while the binding of a GST-βL composed of only the initial 35 amino acids (265-299) was similar to the GST control. In a separate experiment using cell lysates as a source of BARA-L, BARA was able to interact with residues 265-375, but not 375-515 of βL (FIG. 8B). The lack of binding of GSTβL375-515 is not due to a conformational problem since this GST was able to interact with STAT2 (FIG. 8B, lower panel). These data indicate that the BARA binding site of IFNαRβL involves the region surrounding amino acid 346.

EXAMPLE 5

Figure 10:
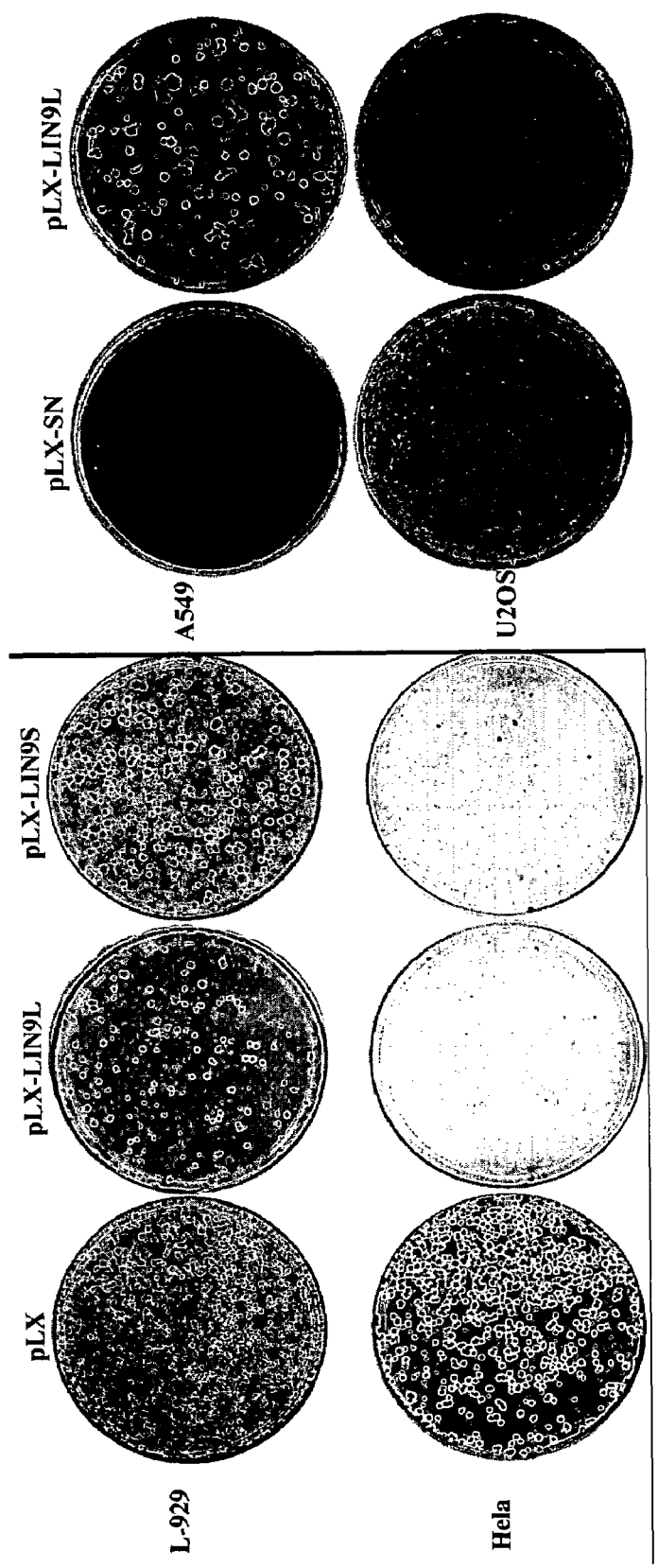
FIG. 10 shows a colony assay in cells infected with a recombinant retrovirus encoding BARA-L, BARA-S (indicated as LIN9-L and LIN9-S) and vector control.

BARA/LIN9 Regulates Cell Proliferation in Mammalian, C. elegans, and Yeast Systems A. Expression of BARA in Mammalian Cells using Retroviral Vectors Inhibits Colony Formation BARA was subcloned into the retroviral vector pLXSN, pLX-BARA-S and pLX-BARA-L, retroviruses were packaged in PA317 cells, and virus-containing supernatants were used to infect a variety of cell lines including rodent L-929 and Rat1 cells, and human U2OS, Hela, and A549 cells. As shown in FIG. 10, very few or no colonies were recovered after G418 selection for U2OS, Hela, and Rat1 cells infected with pLX-LIN9/BARA-S and pLX-LIN9/BARA-L (FIG. 10 pLX-LIN9S and pLX-LIN9L, respectively). Infection of these cell lines with empty retrovirus yielded several hundred colonies in all cases. Although colonies were recovered from A549 cells infected with BARA/LIN9-S and BARA/LIN9-L, the numbers were lower than in control virus. These results indicate that enforced expression of BARA/LIN9 inhibits colony formation in some cell types. This toxic effect was observed in U2OS cells that expressed wild type RB, as well as in Hela cells in which RB and other pocket proteins are rendered non-functional by viral oncoproteins (e.g., E7). Human BARA/LIN9 likely regulates S phase entry as in C. elegans, and thus is localized downstream of RB or downstream of Cyclin D/CDK4 in a pathway parallel to RB as is known for C. elegans LIN9. Boxen et al., 2002, Current Biol. 12:906-911).

Figure 11:
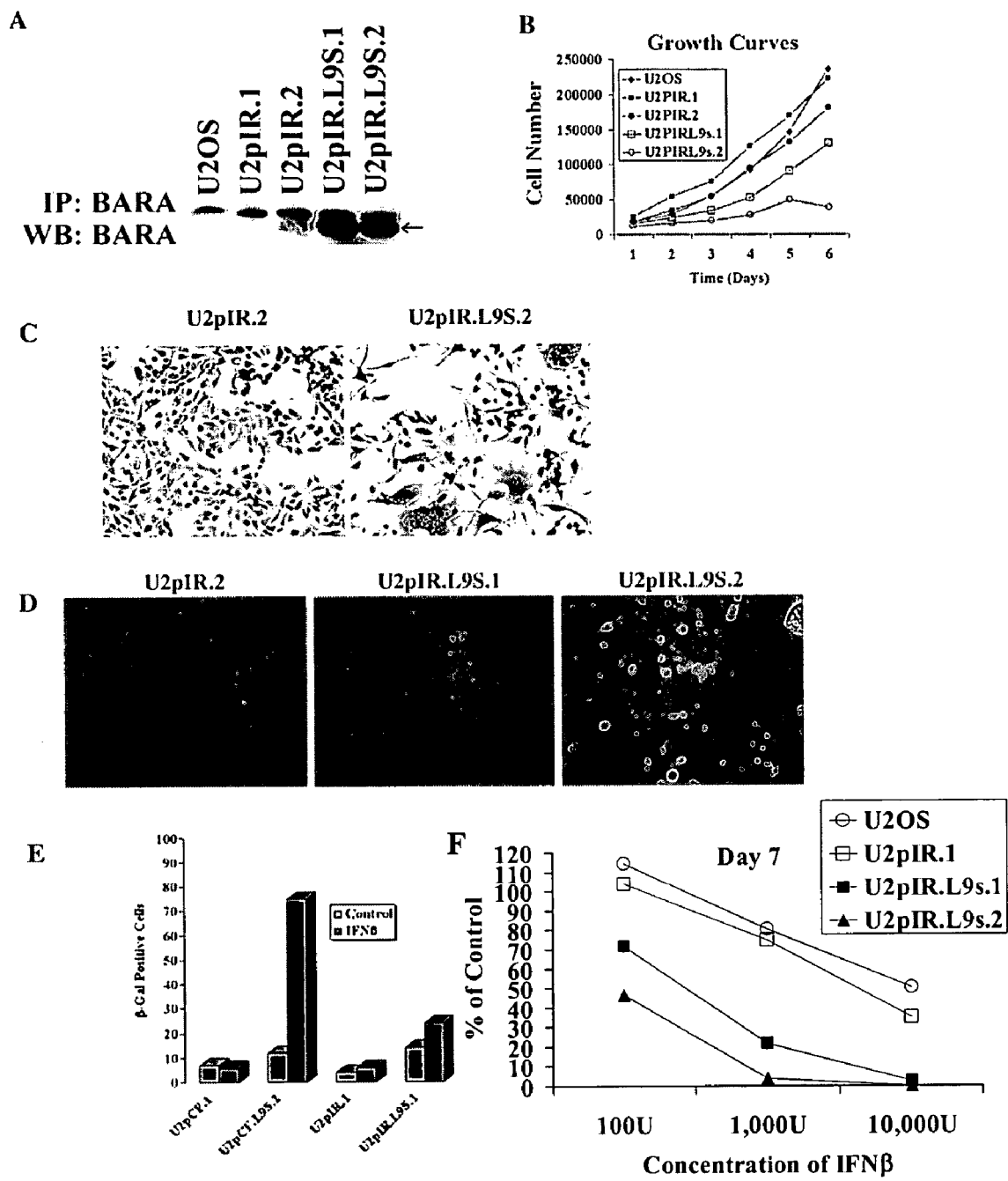
FIG. 11A shows the expression of BARA-S in stable transfectants. Cell lysates were precipitated with an anti-BARA rabbit serum and then immunoblotted with anti-BARA mouse sera. The migration of the transfected BARA-S is indicated. The band above BARA-S corresponds to endogenous BARA-L.
FIG. 11B shows proliferation of BARA-S expressing cells. Cells were seeded at about 20,000 cells/well in 24-well plates and counted every day.
FIGS. 11C and 11D show Giemsa and beta-galalactosidase staining, respectively, of U2pIR.L9S.1, -2 and control U2pIR.1 cells.
FIG. 11E show detection of beta-gal positive cells after IFNβ treatment.
FIG. 11F shows MTT assay results showing the effect of IFNβ on the proliferation of cells expressing BARA.

B. Stable Expression of BARA-S Impairs Cell Proliferation and Stabilizes P53 Expression The development of cell lines stably expressing BARA-L or -S was achieved after following the fate of cells transfected with a pCMV-driven bicistronic vector system in which BARA and EGFP were separated by an IRES (pIRES2-BARA-S). U2OS cells were transfected and selected in G418. After more than 45 days in selection two clones weakly positive for EGFP were isolated. Expression of BARA-S was confirmed by immunoprecipitation (IP) with the rabbit anti-BARA antibody followed by Western blotting (WB) with a mouse anti-BARA antibody (FIG. 11A). Both clones expressing BARA-S (U2pIRL9s.1 and U2pIRL9s.2) proliferated at a slower rate than control cells (parental U2OS, and U2OS transfected with empty vector-U2pIR.1 and U2pIR.2) (FIG. 11B). Interestingly, microscopic examination of the clone in which cell proliferation was more severely affected (U2pIR.L9S.2), revealed cells that were large and flat resembling senescent cells (FIG. 11C). FIG. 11D shows that the senescent nature of these cells was confirmed by staining with β-galactosidase (46).

Whether the lower levels of senescence detected in U2pIR.LS9.1 would be increased by treatment with IFNβ was then determined. For these experiments, another independent clone obtained by cotransfection of a membrane-linked form (farnesylated) of EGFP and BARA-S was utilized (U2 pCF.L9S.2; as distinguished from U2pIR.L9S.2 above), which proliferated slower than the corresponding control (U2 pCF.1) and had few senescent cells. FIG. 11E shows that IFNβ treatment for 6 days increased the levels of β-gal positive cells significantly in U2 pCF.L9S.2 and to a lesser extent in U2pIR.L9S.1. Increased levels of apoptotic cells were also detected in both cell lines. FIG. 11F shows the effect of IFNβ treatment on proliferation of two independent clones expressing BARA, which results indicate a combined induction of apoptosis and senescence. Altogether, these data indicate that BARA is a regulator of cell proliferation and senescence. Additionally, the effect on cell senescence and apoptosis can be induced by treatment with IFNβ.

It is important to point out that the presence of senescent cells in tumor cell lines is unusual and indicates that some cells have lost their immortal phenotype possibly because BARA has re-established a check point previously lost during tumor development. Moreover, there are no previous reports indicating that type I IFNs can induce senescence. BARA's ability to induce cell death in tumor cells lines may be exploited to treat mammalian tumors.

Figure 12:
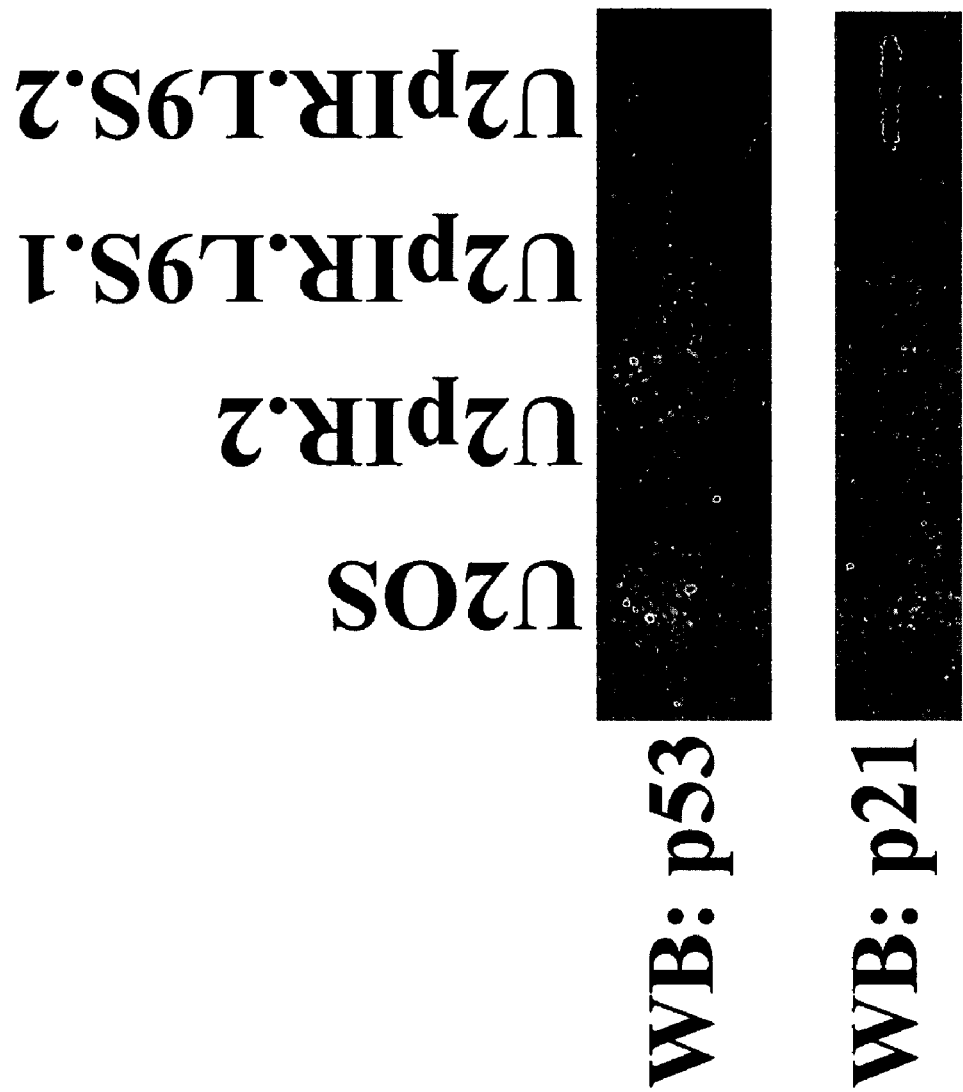
FIG. 12 shows the expression of p53 and p21 in U20S cells stably transfected with BARA-S.

The presence of senescent cells in one of the stable clones, U2pIR.L9S.2, raised the question as to whether the p53-p21 pathway was activated in these cells. FIG. 12 shows that the levels of p53 were increased in both clones, however, U2pIR.L9S.2 cells show remarkably higher levels of p53 and p21 which correlate with the slower proliferation rate and the presence of senescent and apoptotic cells. These results indicate that overexpression of BARA can result in induction and/or stabilization of p53.

c. The Function of BARA is Conserved from Yeast to Mammalian Cells

To determine whether the function of human/mouse and C. elegans BARA/LIN9 was conserved, the multivulva phenotype observed in lin8;lin9 and lin15a;lin9 worm mutants was rescued using huLIN9/BARA. Table 3 shows that huLIN9/BARA-S, which is less toxic than the long form in human cells, was able to rescue 10% of the animals. This result indicates that huBARA has conserved some of the functions of C. elegans LIN9. Additionally, the injection of huBARA-S and L was systematically toxic as demonstrated by the reduced progeny obtained. The toxic effect was observed not only in Muv animals, but also in wild type worms indicating that huBARA is also toxic in C. elegans.

Figure 18:
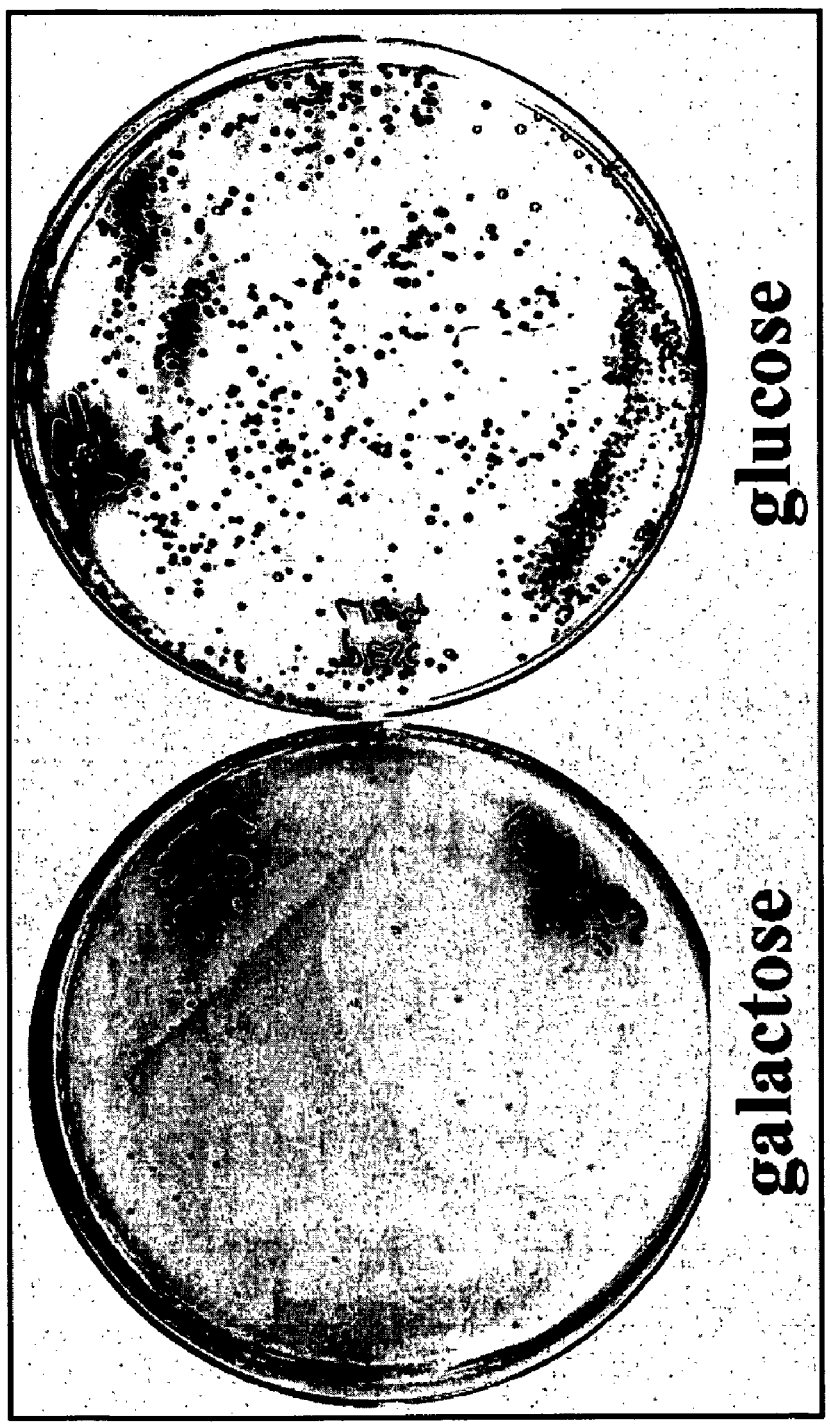
FIG. 18 shows recombinant expression of BARA in yeast. Cells were transformed with an expression plasmid carrying BARA under the control of a gal4 promoter. Positive clones were then plated in galactose or glucose containing medium.

To test if the pathway was also present in yeast, huBARA was subcloned in a vector under the control of an inducible system (Gal4), and introduced it into yeast. Cells grown in glucose plates formed normal colonies however, when they were plated in medium containing galactose just a few small and pale colonies were obtained (FIG. 18). These data further suggest that the growth regulatory pathway activated by BARA is conserved from yeast to humans.

TABLE 3

Expression of huLIN9/BARA in *C. Elegans*.

| Worm Genotype/Phenotype | animals injected(gene) | Brood/ worm | Muv | Normal | Comment |
|---|---|---|---|---|---|
| 1 lin8(n111); lin9(n112)/Muv | 5 (huBARA-S) | 40 | 90% | 10% | Low Brood |
| 2 lin15(n309); lin9(n112)/Muv | 5 (huBARA-L) | 18 | 100% | 0% | Low Brood |
| 3 MT111, lin8(n111)/WT | 6 (control vec) | 120 | 0% | 100% | Normal Progeny |
| 4 MT111, lin8(n111)/WT | 5 huBARAs | 45 | 0% | 100% | Embryonic Lethal |
| 5 N2/WT | 5 vector; rol-6 | 112 | 0% | 100% | Normal Progeny |

The first column describes the mutated genes and the phenotypes observed. Worms with mutations in a gene in pathway A (lin8 or lin15a) and lin9 (pathway B) were used as source of multivulva animals.

EXAMPLE 6

Figure 13:
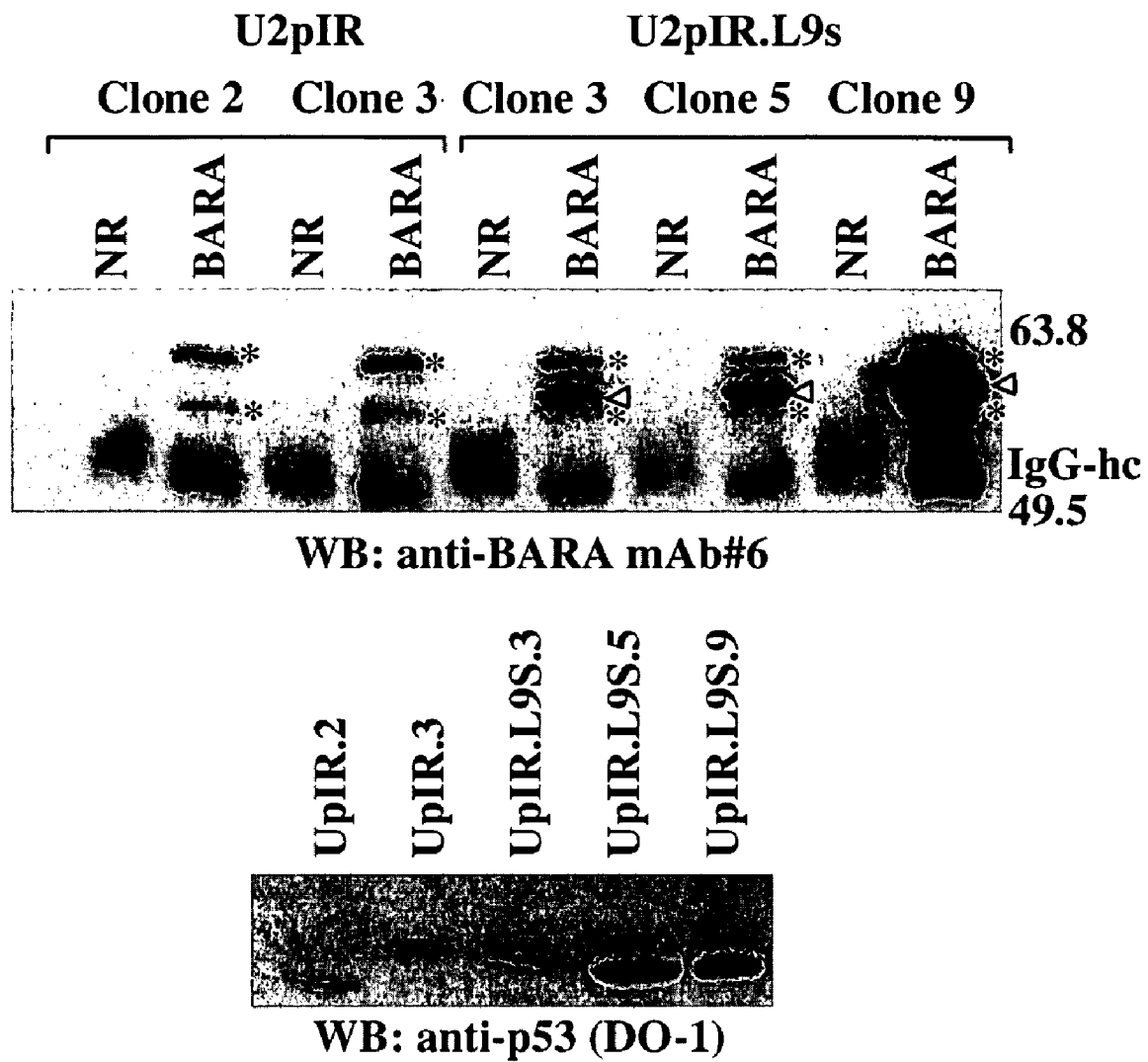
FIG. 13 shows the stable expression of BARA. The migration of the BARA-S and BARA-L is indicated. IPs were performed with normal rabbit serum (NR) or anti-BARA antibody (BARA) followed by Western blot with the anti-BARA mAb#6.

BARA Stabilizes the Expression of P53 and Negatively Regulates Cell Proliferation in U20S To determine if the stabilization of p53 is a constant event observed after the overexpression of BARA, new transfections and selected again for stable clones that express EGFP were performed. FIG. 13 shows that clones UpIR.L9S.3, 0.5 and 0.9 express exogenous recombinant BARA, while clone U2pIR.2 and U2pIR.3 corresponding to U2OS transfected with empty express only endogenous BARA-S and -L. It is worth mentioning that the transfected BARA-S migrates slightly slower (FIG. 13, arrow head) than the endogenous protein (lower asterisk) due to the inclusion of a C-terminal HA-tag. All clones that stably express BARA also contain higher levels of p53, indicating that BARA plays a role in the regulation of this tumor suppressor protein.

To further explore the role of BARA in the p53 pathway, different combinations of pCMV-BARA-S and p53 with trace amounts of a membrane-associated form (farnesylated) of the EGFP (ratio BARA-S to EGFP of 10/1) were cotransfected into SAOS-2 cells. Cotransfection of BARA and p53 increase the number of dead cells to 37%, from 23% observed in cells transfected with p53 alone. The finding that coexpression of BARA-S and p53 induced apoptosis in SAOS-2 (p53$^{-/-}$) cells indicates that BARA participates in a p53-dependent apoptotic pathway.

EXAMPLE 7

Production of BARA$^{-/-}$ KO Mice

Figure 14:
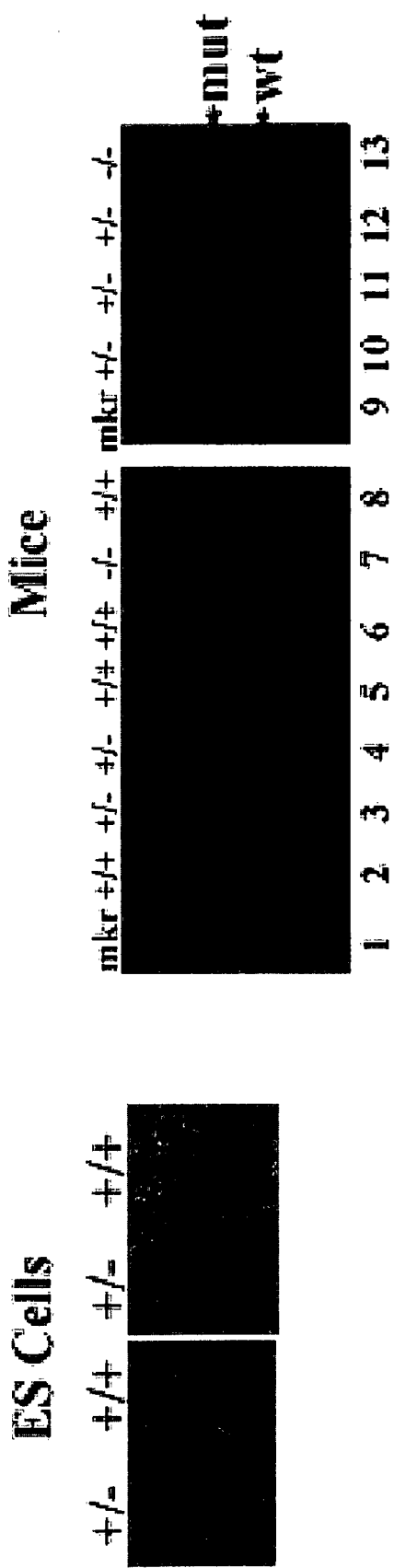
FIG. 14 demonstrates production of BARA$^{-/-}$ mice. Southern blots show ES cells (left) and mice (center) with targeted disruption of the BARA gene. The mutant (mut) and wild type (wt) alleles are indicated. IP/Western blot analyses using polyclonal (BA) and mAb #6, respectively, and cell lysates from MEF-BARA$^{+/+}$ and MEF-BARA$^{-/-}$ from two different embryos.

The production of mice null for BARA is important for the understanding of the physiological role of this gene. This will also allow us to study cells from those KO animals, i.e., MEF, and determine if BARA is part of the p53 pathway. BAC clones carrying the entire mouse BARA gene from a RW4 library were obtained. One of these clones was used to characterize the exon-intron organization of the mouse gene and to produce a targeting construct that replaced exons 2-3 with the neo cassette. The targeting construct was electroporated into ES-RW4 cells. After selection in G418/Gancyclovir, five ES clones out of 175 screened carried a disruption of one allele of the BARA gene (FIG. 14, ES cells). Four of these clones were injected into blastocysts of C57BL/6 mice and obtained 9 chimeric mice that were then bred into a C57BL/6 background. Heterozygous mice were bred to obtain BARA null mice (FIG. 14, Mice). BARA-/- mice were obtained in the appropriate ratio for Mendelian transmission of the mutation (expected 25%-/-, 25%+/+, 50%+/-) and are fertile. Interestingly, one of the first null mice obtained developed an abdominal tumor localized to the left flank 6 months after birth (January, 2003). The tumor is well tolerated and the animal has not yet been sacrificed to determine its nature. The remaining animals from that first litter of null mice do not show yet any evidence of tumors. Immunoprecipitation/ Western blotting performed with MEFs derived from wild type and BARA$^{-/-}$ embryos showed a disappearance of the long and short forms of the BARA protein in null embryos. A weak band with a MW of approximately 49 kDa observed in wild type and BARA null cells is likely to correspond to cross-reactivity with the heavy chain of the rabbit IgG although this remain to be confirmed (data not shown). Alternatively, the 49 kDa band could correspond to a small remnant of the BARA protein due to a partial knockout of the BARA gene. The targeted disruption and analysis of the phenotype of BARA$^{-/-}$ is performed in close collaboration with Dr. Hiroaki Kiyokawa.

Figure 15:
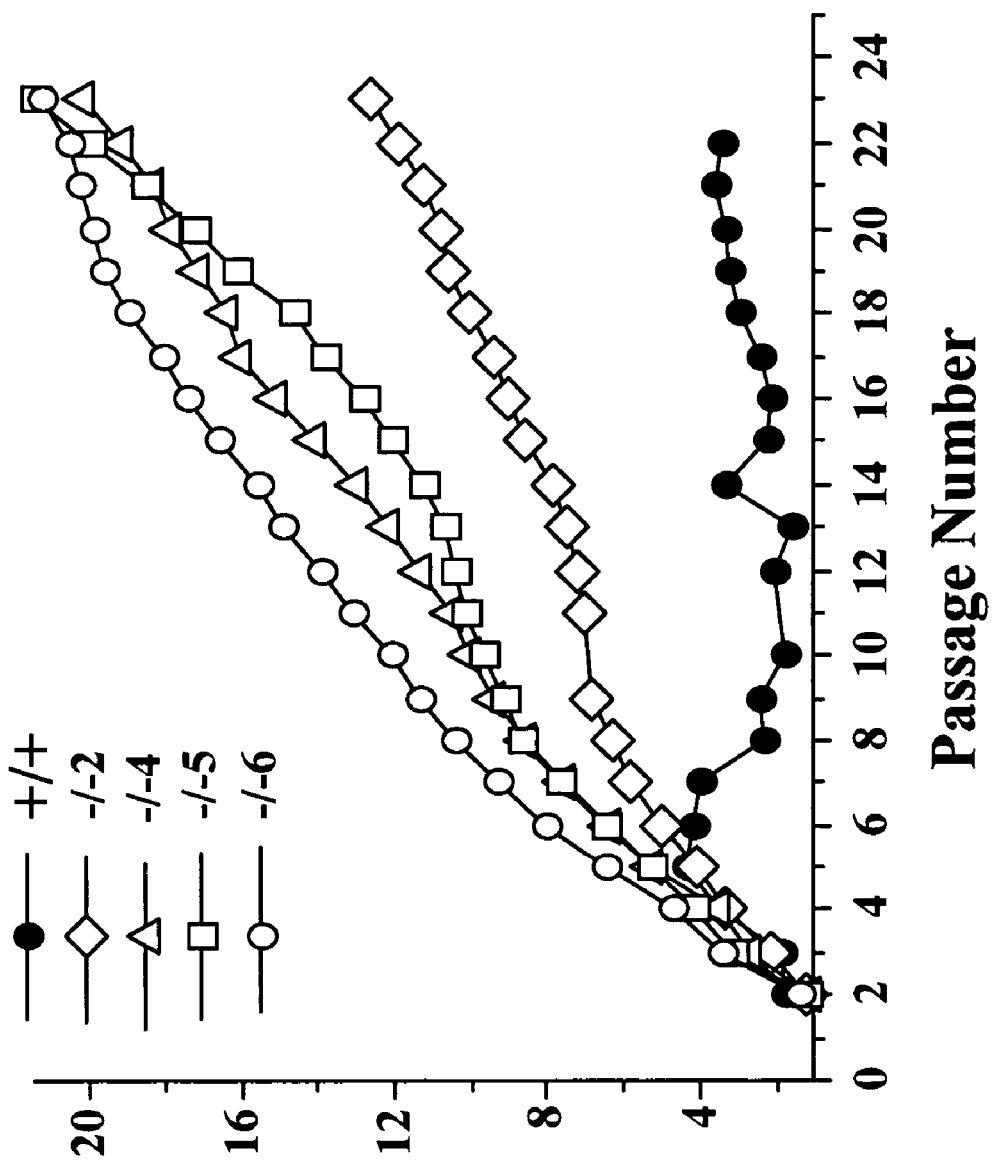
FIG. 15 shows a pool of mouse embryonic fibroblasts (MEFs) derived from more than 30 BARA$^{+/+}$ embryos and BARA$^{-/-}$ MEFs from 4 embryos were grown in culture following a 3T3 protocol for 23 passages.

MEFs null for BARA were developed from 4 separate embryos. The growth of MEF-BARA$^{-/-}$ and MEF-WT (corresponding to a pool of approximately 30 embryos) were studied using a 3T3 protocol. FIG. 15 shows that BARA$^{-/-}$ cells, unlike MEF+/+, did not undergo senescence. Although proliferation of some BARA$^{-/-}$ cells slowed down between passages 9-12, they never stall completely as observed with wild type cells.

Figure 16:
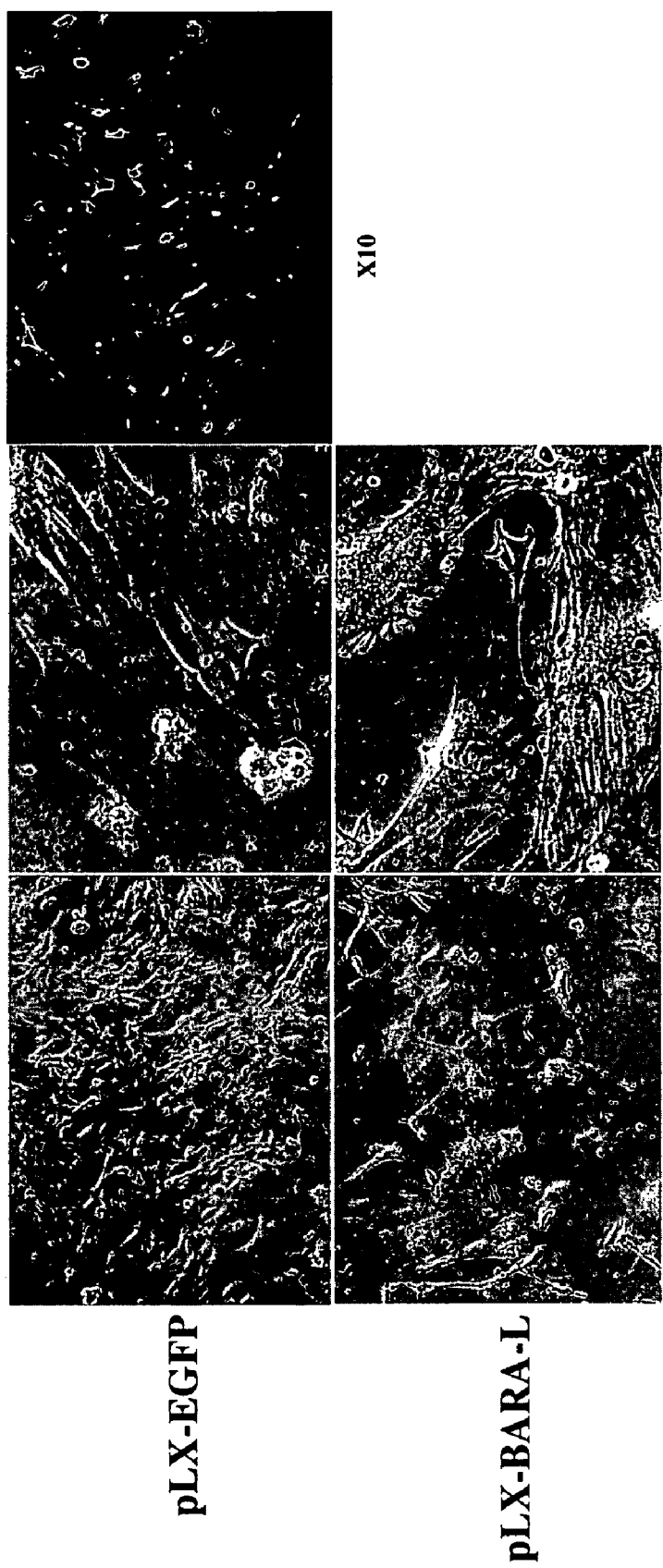
FIG. 16 demonstrates that expression of BARA induces senescence in wildtype (wt) MEFs. wtMEFs were transduced with EGFP or BARA-L retroviruses, selected with G-418 for 5 days, and further cultured for 6 days. Pictures were taken using a CCD camera connected to a Nikon microscope. The fluorescent image corresponds to the X10 bright field.

To further demonstrate the role of BARA in senescence, wild type MEFs were infected with a retrovirus carrying the EGFP (pLX-EGFP) or BARA-L (pLX-BARA-L), selected for 5 days in 750 µg/ml of G-418, and the assessed for senescence by morphology and senescence-associated β galactosidase (SA-βgal) staining. FIG. 16 shows that fewer numbers of cells were present in cultures infected with BARA-L. Moreover, BARA-L infected cells had the typical enlarged and flat morphology of senescent cells. SA-βgal staining showed that 39% of the BARA-L infected cells were positive, while only 15% positive cells were detected in cells infected with the EGFP virus.

In summary, the data obtained with MEF-BARA$^{-/-}$ and by overexpression of BARA in wild type MEFs indicate a role of BARA in senescence.

EXAMPLE 8

BARA Co-Localizes with ARF in the Nucleolus

Figure 17:
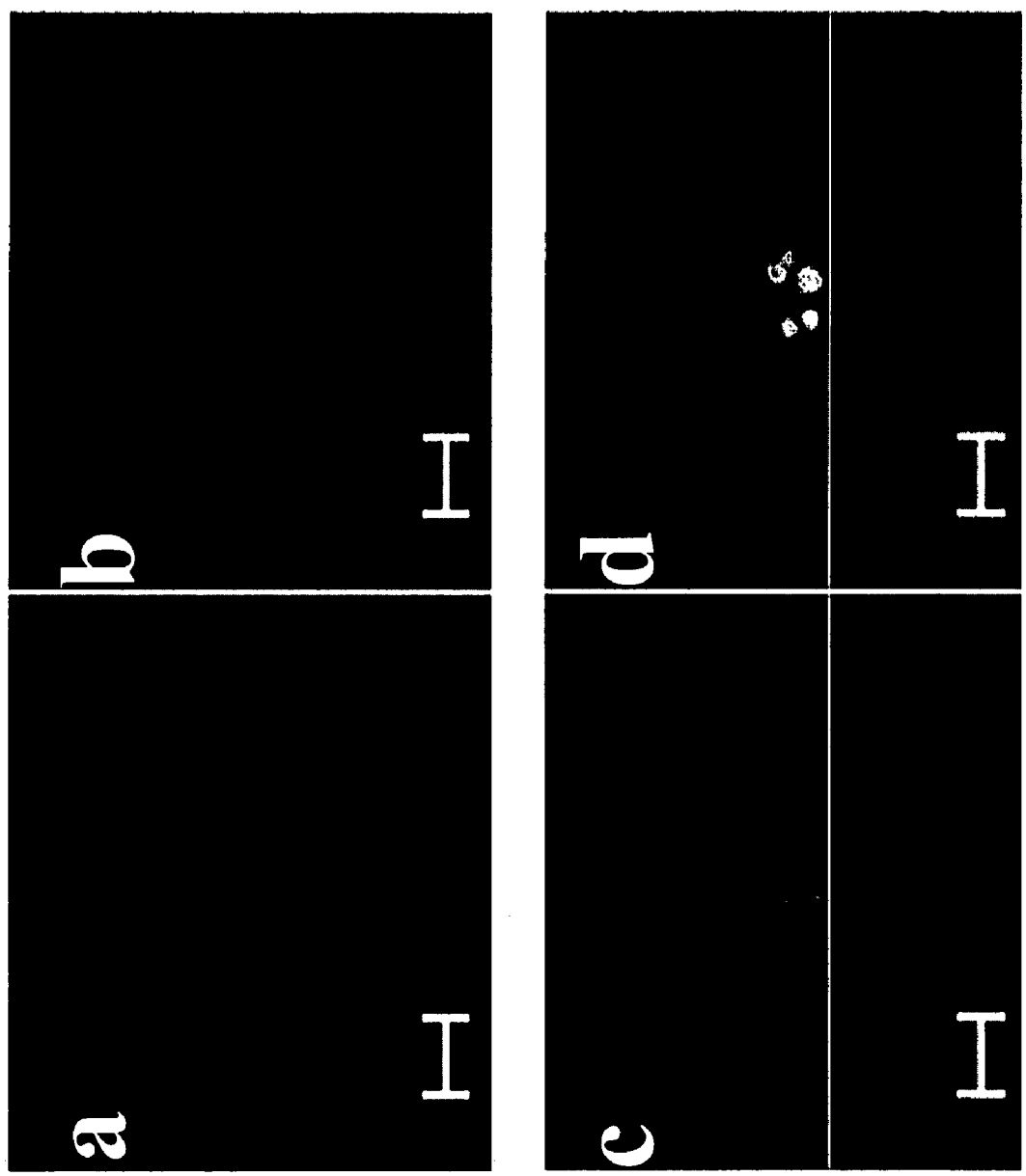
FIG. 17 shows ARF-RFP (a, red) and GFP-BARA (c, green) co-localize (d, merge) in Hoechst (b, blue) negative areas. Hash-mark equals 10 micron.

A critical step in the regulation of p53 involves its stabilization through the inhibition of HDM2/MDM2 (the underlined H and M stand for human and murine, homologs of this gene, respectively), which is responsible for p53 degradation. ARF can sequester MDM2/HDM2 in the nucleolus allowing p53 to remain in the nucleoplasm and induce specific genes that can induce apoptosis, or cell cycle arrest/senescence. In order to determine the subcellular localization of BARA, a BARA:EGFP fusion protein (green) was transiently expressed and, as a nucleolar marker, used an ARF-RFP (red) fusion protein for confocal microscopy studies. FIG. 17 shows that 48 hours after transfection BARA co-localizes with ARF in nucleoli. Interestingly, PA317 and U2OS cells overexpressing BARA:EGFP, but not control EGFP become apoptotic 48-72 hours after transfection and almost no BARA:EGFP positive cell are detected by day 5 (data not shown). Altogether, the nucleolar localization, the induction of p53 in stable clones, and the induction of senescence and apoptosis indicate that BARA may exert its effect on p53.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A purified antibody or antigen-binding fragment thereof produced by a hybridoma having American Type Culture Collection (ATCC) patent deposit number PTA-5191, wherein said antibody or antigen-binding fragment thereof specifically binds a BARA polypeptide.

2. The antibody of claim 1, wherein the antibody is a humanized, chimeric, or CDR-grafted antibody, or antigen-binding fragment thereof.

3. The antigen-binding fragment of claim 1, wherein the antigen-binding fragment is a variable region fragment.

4. The variable region fragment of claim 3, wherein the variable region fragment is a Fab or Fab' fragment.

5. The antibody or antigen-binding fragment thereof of claim 1, wherein said antibody or antigen-binding fragment thereof antagonizes BARA polypeptide biological activity.

6. A composition comprising the antibody or antigen-binding fragment thereof of claim 1 and a pharmaceutically acceptable formulation agent, wherein the pharmaceutically acceptable formulation agent is a carrier, adjuvant, solubilizer, stabilizer, or anti-oxidant.

7. A method of detecting or quantitating the amount of BARA polypeptide in a sample, the method comprising contacting the sample with the anti-BARA antibody or antigen-binding fragment thereof of claim 1.

8. A hybridoma that produces an antibody capable of binding an isolated BARA polypeptide, wherein the hybridoma has ATCC patent deposit number PTA-5191.

* * * * *

SEQUENCE LISTING

<160> NUMBER OF SEQ ID NOS: 10

<210> SEQ ID NO 1
<211> LENGTH: 2908
<212> TYPE: DNA
<213> ORGANISM: Homo sapiens

<400> SEQUENCE: 1

```
cagcctttga aaaagcggcg cggctcgttc aagatggcgg agctcgacca gttgcctgac      60
gagagctctt cagcaaaagc ccttgtcagt ttaaaagaag gaagcttatc taacacgtgg     120
aatgaaaagt acagttcttt acagaaaaca cctgtttgga aaggcaggaa tacaagctct     180
gctgtggaaa tgaaatttac agcaacaatg tcaacaccag ataagaaagc ttcacagaag     240
attggttttc gattacgtaa tctgctcaag cttcctaaag cacataaatg gtgtatatac     300
gagtggttct attcaaatat agataaacca cttttgaag gtgataatga cttttgtgta     360
tgtctaaagg aatctttcc taatttgaaa acaagaaagt taacaagagt agaatgggga     420
aaaattcggc ggcttatggg aaaaccacgg agatgttctt ctgcattttt tgaggaagag     480
agatcagcat taaaacagaa acggcagaaa ataaggctct tacaacaaag gaaagttgca     540
gatgtttcac attcaaagat ctcccagatg aaattccttt gcctctggtt attggaacga     600
aagttacagc acgattacgt ggtgttcatg atggtttgtt cactggacaa atagatgctg     660
tggatactct taatgctact tatagagtaa cttttgatag gacagggctt ggaacccata     720
ccatccctga ctatgaagtt ctcagtaatg aacctcatga gacaatgcca attgctgcct     780
ttggacaaaa acagcggcct tctcgatttt ttatgacccc accacggtta cattatactc     840
ctcctctcca gtcaccaatt atagataatg atcctttatt aggacagtcg ccgtggagaa     900
gtaaaatttc tggctctgac actgaaacat taggtggttt tccagtagaa tttcttatcc     960
aagtgaccag attatcaaaa attctcatga ttaaaaagga acatatcaag aaattaaggg    1020
aaatgaacac agaagcagaa aaattgaaat catattccat gcccatcagc attgaatttc    1080
agcggagata tgcaacaatt gttctggagc ttgaacagct gaacaaggac ctaaacaaag    1140
ttttgcataa agttcaacag tattgctatg agcttgctcc agaccagggg ctccagcctg    1200
cagatcagcc aacagatatg agacgcaggt gtgaggaaga agcacaggaa attgttcggc    1260
atgcaaattc ctcaacagga cagccctgcg ttgaaaatga aatctgaca gacttaattt    1320 ccaggcttac agctattttg ttacaaatta agtgtctagc agaaggagga gacctgaatt    1380
cctttgaatt caaatcactt acagactcat taatgatat caagagtaca atagacgctt    1440
ctaatatcag ttgctttcag aataatgtag aaatccatgt tgcacatatt cagagtggcc    1500
tgagccagat gggaaactta catgcctttg cagcaaataa caccaacaga gactgagtaa    1560
agatttcatt attccaactg cacgggacat tgttttgag aagttctttt cctttatata    1620
```

```
ggcttccaac accaaataac ctaactgctg gaaaacaagg gaaatttaaa tctccaaata    1680
aggcatttta atagactgta ctgcttctta aaccagcatt gctgaccagc attatattta    1740
tttttctttt attattcaga tgcagtagca ttgcttatgt tacatatgtt tatattcaca    1800 aatatttta aactgaaata tctgaacata atataatttc gtggaagaat acattgacca     1860
ttttttttaa tgtgcatgaa ttcaccgcaa cacatgcaga caactgctgc aatggagagt    1920
atgaagaaac ctggtctttt tattcatgtc ggtggcagtg tggaaattcc atccagaaaa    1980
ttacaactcc acttgattta gttgatcacc atctcagtct tcaaaagata acatcatgag    2040
gtgtgggaag tcctagtttt aaggaaacca ctgaaatata gatgggaaat gtggacttta    2100
caagtatatg ttatatatac ttgcaatgtg acatggttct gtagatcatt ttataataat    2160
aaatatttta atttatcata acatataaaa gaaacctttg ttgtttgttg aaagaaaatg    2220
aaggaacagg gggaaaaaag gtgcaaaatg ctaaatttct aaaaatggat ttggcatgtc    2280
ttcccatcag ttcaggtcaa aagtgcattg ttgtgagatt tattaaaaaa aaaatgataa    2340
cacactattt tcatattttt ttgtttattt gcacaacttt taaaccagat tactggttaa    2400
aatccaacag tacacaattt ataaagtaaa aagattttat aaggaaaaca aatataataa    2460
ccagtgctgt gaaatgcaga agaaaggctt gttttggttg ttttttcttt ttaggaaaac    2520
gctgcctaaa atgttaatct tgtaaaaagt atgtatttgg aattttcttc gttttaatag    2580
aatattataa actcaaaata taaattttt tcaaatttgg agtttaagat atagctgtag     2640
aggtggtttt aattccttta gatgtctcat aaaatgagac tttttatatg ttaatgtata    2700
ataaaactga aacaagatta ttttccattt gaaattttg tatagtttaa aaaggcttcc     2760
gtattctttg ttggtattgt gccactgcag aactttagtg cagagtttat atttagctaa    2820
actgttatgt taattaagaa atgcataaat cttctattct taatatttgt aattctaaat    2880
aaattgatct atgaaaatta ttattttc                                       2908
```

<210> SEQ ID NO 2
<211> LENGTH: 3005
<212> TYPE: DNA
<213> ORGANISM: Homo sapiens

<400> SEQUENCE: 2

```
cagcctttga aaaagcggcg cggctcgttc aagatggcgg agctcgacca gttgcctgac    60
gagagctctt cagcaaaagc ccttgtcagt ttaaaagaag gaagcttatc taacacgtgg    120
aatgaaaagt acagttcttt acagaaaaca cctgtttgga aaggcaggaa tacaagctct    180
gctgtggaaa tgccttttcag aaattcaaaa cgaagtcgac ttttttctga tgaagatgat    240
aggcaaataa atacaaggtc acctaaaaga aaccagaggg ttgcaatggt tccacagaaa    300
tttacagcaa caatgtcaac accagataag aaagcttcac agaagattgg ttttcgatta    360
cgtaatctgc tcaagcttcc taaagcacat aaatggtgta tatacgagtg gttctattca    420
aatatagata aaccacttt tgaaggtgat aatgacttt gtgtatgtct aaaggaatct    480
tttcctaatt tgaaaacaag aaagttaaca agagtagaat ggggaaaaat tcggcggctt    540
atgggaaaac cacggagatg ttcttctgca ttttttgagg aagagagatc agcattaaaa    600
cagaaacggc agaaaataag gctcttacaa caaaggaaag ttgcagatgt tcacaattc     660 aaagatctcc cagatgaaat tcctttgcct ctggttattg gaacgaaagt tacagcacga    720
ttacgtggtg ttcatgatgg ttttgttcact ggacaaatag atgctgtgga tactcttaat   780
```

-continued

```
gctacttata gagtaacttt tgataggaca gggcttggaa cccataccat ccctgactat    840
gaagttctca gtaatgaacc tcatgagaca atgccaattg ctgcctttgg acaaaaacag    900
cggccttctc gatttttat gaccccacca cggttacatt atactcctcc tctccagtca    960
ccaattatag ataatgatcc tttattagga cagtcgccgt ggagaagtaa aatttctggc   1020
tctgacactg aaacattagg tggttttcca gtagaatttc ttatccaagt gaccagatta   1080
tcaaaaattc tcatgattaa aaaggaacat atcaagaaat taagggaaat gaacacagaa   1140
gcagaaaaat tgaaatcata ttccatgccc atcagcattg aatttcagcg gagatatgca   1200
acaattgttc tggagcttga acagctgaac aaggacctaa acaaagtttt gcataaagtt   1260
caacagtatt gctatgagct tgctccagac caggggctcc agcctgcaga tcagccaaca   1320
gatatgagac gcaggtgtga ggaagaagca caggaaattg ttcggcatgc aaattcctca   1380
acaggacagc cctgcgttga aaatgaaaat ctgacagact taatttccag gcttacagct   1440
attttgttac aaattaagtg tctagcagaa ggaggagacc tgaattcctt tgaattcaaa   1500
tcacttacag actcattaaa tgatatcaag agtacaatag acgcttctaa tatcagttgc   1560
tttcagaata atgtagaaat ccatgttgca catattcaga gtggcctgag ccagatggga   1620
aacttacatg cctttgcagc aaataacacc aacagagact gagtaaagat ttcattattc   1680
caactgcacg ggacattgtt tttgagaagt tcttttcctt tatataggct tccaacacca   1740
aataacctaa ctgctggaaa acaagggaaa tttaaatctc caaataaggc attttaatag   1800
actgtactgc ttcttaaacc agcattgctg accagcatta tatttatttt tcttttatta   1860
ttcagatgca gtagcattgc ttatgttaca tatgtttata ttcacaaata ttttaaact   1920
gaaatatctg aacataatat aatttcgtgg aagaatacat tgaccatttt ttttaatgtg   1980
catgaattca ccgcaacaca tgcagacaac tgctgcaatg gagagtatga agaaacctgg   2040
tctttttatt catgtcggtg gcagtgtgga aattccatcc agaaaattac aactccactt   2100
gatttagttg atcaccatct cagtcttcaa aagataacat catgaggtgt gggaagtcct   2160
agttttaagg aaaccactga atatagatg gaaatgtgg actttacaag tatatgttat   2220
atatacttgc aatgtgacat ggttctgtag atcatttat aataataaat attttaattt   2280
atcataacat ataaaagaaa cctttgttgt ttgttgaaag aaaatgaagg aacaggggga   2340
aaaaaggtgc aaaatgctaa atttctaaaa atggatttgg catgtcttcc catcagttca   2400
ggtcaaaagt gcattgttgt gagatttatt aaaaaaaaaa tgataacaca ctattttcat   2460
attttttgt ttatttgcac aacttttaaa ccagattact ggttaaaatc caacagtaca   2520
caatttataa agtaaaaaga ttttataagg aaaacaaata taataaccag tgctgtgaaa   2580
tgcagaagaa aggcttgttt tggttgtttt tctttttag gaaaacgctg cctaaaatgt   2640
taatcttgta aaaagtatgt atttggaatt ttcttcgttt taatagaata ttataaactc   2700
aaaatataaa ttttttcaa atttggagtt taagatatag ctgtagaggt ggttttaatt   2760
cctttagatg tctcataaaa tgagactttt tatatgttaa tgtataataa aactgaaaca   2820
agattatttt ccatttgaaa ttttgtata gttaaaaag gcttccgtat tctttgttgg   2880
tattgtgcca ctgcagaact ttagtgcaga gtttatattt agctaaactg ttatgttaat   2940
taagaaatgc ataatcttc tattcttaat atttgtaatt ctaaataaat tgatctatga   3000
aaatt                                                              3005
```

<210> SEQ ID NO 3
<211> LENGTH: 1720

<212> TYPE: DNA
<213> ORGANISM: Mus musculus

<400> SEQUENCE: 3

```
cagcctttga aaaagcggcg cggctcgttc aagatggcgg agctcgacca gttgcctgac    60
gagagcttgg cccctteccc tgggactaca ggtggccctg acctttccg gagatgatcc   120
agccgggata cagtgccgag gctcttcagc aaaagccctt gtcagtttaa agagggaag   180
tttatctaac acatggaatg aaaagtacag ttctttacag aaaactcctg tttggaaagg   240
caggaatgcg ggccctgctg tagaaatgcc tttcagaaat tcaaaagaa gtcgactctt   300
ttctgatgaa gatgacagac aaataaatac aaagtcacct aaaagaaacc agagagtggc   360
aatgatccca cagaaattta cagcaacgat gtcaacacca gataagaaag catcacagaa   420
gattggtttt cgattacgga acctactcaa gcttcccaaa gcacataagt ggtgcatata   480
tgagtggttc tactcaaaca tagacaagcc acttttgaa ggagataatg acttttgtgt   540
atgcctaaag gaatcctttc ctaatttgaa acaagaaaa ttaacaagag tagaatgggg   600
aaaaatcagg agactgatgg gaaaacctcg gagatgttct tctgcatttt ttgaggaaga   660
gaggtcagcc ttaaaacaga agcggcagaa aatcaggctg ttacaacaaa ggaaagttgc   720
agatgtttca cagttcaaag atctccccga tgaaatccct ctaccctgg ttattggaac   780
caaagttaca gcgcggttac gtggcattca cgatggcctg tttactggtc agatagatgc   840
agtggacact cttaatgcta cttacagagt aactttcgat aggacaggcc ttgggactca   900
caccattcct gactatgaag ttcttagtaa tgagcctcat gagacaatgc caatctctgc   960
ctttggacaa aaacagcggc ttctcggtt ttttatgacc cccccacggt tacattatac  1020
ccctcctctc cagtcaccaa ttacagatgg cgatcctta ctggggcagt caccttggag  1080
aagtaaagtt tctggctctg acacggagac gttaggaggc tttccagtgg aattccttat  1140
ccaggtgact aagttatcaa aaattctcat gataaaaaaa gagcatataa agaaattaag  1200
ggagatgaac acagaagcag aaaagctgaa atcctattcc atgcccattg cattgagtt   1260
tcagcggaga tacgcaacga tcgtcctgga gcttgagcag ctgaacaagg acctgaacaa  1320
agttctgcat aaagttcagc agtattgcta tgagcttgca ccagaccagg gactccagcc  1380
tgccgatcag ccaacagaca tgagacggag gtgtgaggaa gaagcccagg aaatcgtccg  1440
gcaagccaac tctgcttccg gacagccctg tgtagaaaac gaaaatctga cggacttgat  1500
ctccaggctc actgcgattt tattacaaat taagtgtctg gcagagggag gagacctgaa  1560
ttcctttgaa ttcaaatctc tcacagattc attaaatgac ataaaaaaca caatagatgc  1620
ttctaatatc agttgttttc agaataacgt agaaatccat gttgcacata tccagagtgg  1680
cctgagtcag atgggaaact acacgcctt tgcagccaac                         1720
```

<210> SEQ ID NO 4
<211> LENGTH: 507
<212> TYPE: PRT
<213> ORGANISM: Homo sapiens

<400> SEQUENCE: 4

```
Met Ala Glu Leu Asp Gln Leu Pro Asp Glu Ser Ser Ala Lys Ala
 1               5                  10                  15

Leu Val Ser Leu Lys Glu Gly Ser Leu Ser Asn Thr Trp Asn Glu Lys
                20                  25                  30

Tyr Ser Ser Leu Gln Lys Thr Pro Val Trp Lys Gly Arg Asn Thr Ser
            35                  40                  45
```

```
Ser Ala Val Glu Met Lys Phe Thr Ala Thr Met Ser Thr Pro Asp Lys
 50                  55                  60

Lys Ala Ser Gln Lys Ile Gly Phe Arg Leu Arg Asn Leu Leu Lys Leu
 65                  70                  75                  80

Pro Lys Ala His Lys Trp Cys Ile Tyr Glu Trp Phe Tyr Ser Asn Ile
                 85                  90                  95

Asp Lys Pro Leu Phe Glu Gly Asp Asn Asp Phe Cys Val Cys Leu Lys
            100                 105                 110

Glu Ser Phe Pro Asn Leu Lys Thr Arg Lys Leu Thr Arg Val Glu Trp
        115                 120                 125

Gly Lys Ile Arg Arg Leu Met Gly Lys Pro Arg Arg Cys Ser Ser Ala
    130                 135                 140

Phe Phe Glu Glu Glu Arg Ser Ala Leu Lys Gln Lys Arg Gln Lys Ile
145                 150                 155                 160

Arg Leu Leu Gln Gln Arg Lys Val Ala Asp Val Ser Gln Phe Lys Asp
                165                 170                 175

Leu Pro Asp Glu Ile Pro Leu Pro Leu Val Ile Gly Thr Lys Val Thr
            180                 185                 190

Ala Arg Leu Arg Gly Val His Asp Gly Leu Phe Thr Gly Gln Ile Asp
        195                 200                 205

Ala Val Asp Thr Leu Asn Ala Thr Tyr Arg Val Thr Phe Asp Arg Thr
    210                 215                 220

Gly Leu Gly Thr His Thr Ile Pro Asp Tyr Glu Val Leu Ser Asn Glu
225                 230                 235                 240

Pro His Glu Thr Met Pro Ile Ala Ala Phe Gly Gln Lys Gln Arg Pro
                245                 250                 255

Ser Arg Phe Phe Met Thr Pro Pro Arg Leu His Tyr Thr Pro Pro Leu
            260                 265                 270

Gln Ser Pro Ile Ile Asp Asn Asp Pro Leu Leu Gly Gln Ser Pro Trp
        275                 280                 285

Arg Ser Lys Ile Ser Gly Ser Asp Thr Glu Thr Leu Gly Gly Phe Pro
    290                 295                 300

Val Glu Phe Leu Ile Gln Val Thr Arg Leu Ser Lys Ile Leu Met Ile
305                 310                 315                 320

Lys Lys Glu His Ile Lys Lys Leu Arg Glu Met Asn Thr Glu Ala Glu
                325                 330                 335

Lys Leu Lys Ser Tyr Ser Met Pro Ile Ser Ile Glu Phe Gln Arg Arg
            340                 345                 350

Tyr Ala Thr Ile Val Leu Glu Leu Glu Gln Leu Asn Lys Asp Leu Asn
        355                 360                 365

Lys Val Leu His Lys Val Gln Gln Tyr Cys Tyr Glu Leu Ala Pro Asp
    370                 375                 380

Gln Gly Leu Gln Pro Ala Asp Gln Pro Thr Asp Met Arg Arg Arg Cys
385                 390                 395                 400

Glu Glu Glu Ala Gln Glu Ile Val Arg His Ala Asn Ser Ser Thr Gly
                405                 410                 415

Gln Pro Cys Val Glu Asn Glu Asn Leu Thr Asp Leu Ile Ser Arg Leu
            420                 425                 430

Thr Ala Ile Leu Leu Gln Ile Lys Cys Leu Ala Glu Gly Gly Asp Leu
        435                 440                 445

Asn Ser Phe Glu Phe Lys Ser Leu Thr Asp Ser Leu Asn Asp Ile Lys
450                 455                 460
```

```
Ser Thr Ile Asp Ala Ser Asn Ile Ser Cys Phe Gln Asn Asn Val Glu
465                 470                 475                 480

Ile His Val Ala His Ile Gln Ser Gly Leu Ser Gln Met Gly Asn Leu
                485                 490                 495

His Ala Phe Ala Ala Asn Asn Thr Asn Arg Asp
            500                 505

<210> SEQ ID NO 5
<211> LENGTH: 542
<212> TYPE: PRT
<213> ORGANISM: Homo sapiens

<400> SEQUENCE: 5

Met Ala Glu Leu Asp Gln Leu Pro Asp Glu Ser Ser Ala Lys Ala
1               5                   10                  15

Leu Val Ser Leu Lys Glu Gly Ser Leu Ser Asn Thr Trp Asn Glu Lys
                20                  25                  30

Tyr Ser Ser Leu Gln Lys Thr Pro Val Trp Lys Gly Arg Asn Thr Ser
            35                  40                  45

Ser Ala Val Glu Met Pro Phe Arg Asn Ser Lys Arg Ser Arg Leu Phe
        50                  55                  60

Ser Asp Glu Asp Asp Arg Gln Ile Asn Thr Arg Ser Pro Lys Arg Asn
65                  70                  75                  80

Gln Arg Val Ala Met Val Pro Gln Lys Phe Thr Ala Thr Met Ser Thr
                85                  90                  95

Pro Asp Lys Lys Ala Ser Gln Lys Ile Gly Phe Arg Leu Arg Asn Leu
            100                 105                 110

Leu Lys Leu Pro Lys Ala His Lys Trp Cys Ile Tyr Glu Trp Phe Tyr
        115                 120                 125

Ser Asn Ile Asp Lys Pro Leu Phe Glu Gly Asp Asn Asp Phe Cys Val
130                 135                 140

Cys Leu Lys Glu Ser Phe Pro Asn Leu Lys Thr Arg Lys Leu Thr Arg
145                 150                 155                 160

Val Glu Trp Gly Lys Ile Arg Arg Leu Met Gly Lys Pro Arg Arg Cys
                165                 170                 175

Ser Ser Ala Phe Phe Glu Glu Arg Ser Ala Leu Lys Gln Lys Arg
            180                 185                 190

Gln Lys Ile Arg Leu Leu Gln Gln Arg Lys Val Ala Asp Val Ser Gln
        195                 200                 205

Phe Lys Asp Leu Pro Asp Glu Ile Pro Leu Pro Leu Val Ile Gly Thr
210                 215                 220

Lys Val Thr Ala Arg Leu Arg Gly Val His Asp Gly Leu Phe Thr Gly
225                 230                 235                 240

Gln Ile Asp Ala Val Asp Thr Leu Asn Ala Thr Tyr Arg Val Thr Phe
                245                 250                 255

Asp Arg Thr Gly Leu Gly Thr His Thr Ile Pro Asp Tyr Glu Val Leu
            260                 265                 270

Ser Asn Glu Pro His Glu Thr Met Pro Ile Ala Ala Phe Gly Gln Lys
        275                 280                 285

Gln Arg Pro Ser Arg Phe Phe Met Thr Pro Arg Leu His Tyr Thr
290                 295                 300

Pro Pro Leu Gln Ser Pro Ile Ile Asp Asn Asp Pro Leu Leu Gly Gln
305                 310                 315                 320

Ser Pro Trp Arg Ser Lys Ile Ser Gly Ser Asp Thr Glu Thr Leu Gly
                325                 330                 335
```

```
Gly Phe Pro Val Glu Phe Leu Ile Gln Val Thr Arg Leu Ser Lys Ile
                340                 345                 350

Leu Met Ile Lys Lys Glu His Ile Lys Lys Leu Arg Glu Met Asn Thr
            355                 360                 365

Glu Ala Glu Lys Leu Lys Ser Tyr Ser Met Pro Ile Ser Ile Glu Phe
        370                 375                 380

Gln Arg Arg Tyr Ala Thr Ile Val Leu Glu Leu Glu Gln Leu Asn Lys
385                 390                 395                 400

Asp Leu Asn Lys Val Leu His Lys Val Gln Gln Tyr Cys Tyr Glu Leu
                405                 410                 415

Ala Pro Asp Gln Gly Leu Gln Pro Ala Asp Gln Pro Thr Asp Met Arg
            420                 425                 430

Arg Arg Cys Glu Glu Ala Gln Glu Ile Val Arg His Ala Asn Ser
        435                 440                 445

Ser Thr Gly Gln Pro Cys Val Glu Asn Glu Asn Leu Thr Asp Leu Ile
450                 455                 460

Ser Arg Leu Thr Ala Ile Leu Leu Gln Ile Lys Cys Leu Ala Glu Gly
465                 470                 475                 480

Gly Asp Leu Asn Ser Phe Glu Phe Lys Ser Leu Thr Asp Ser Leu Asn
                485                 490                 495

Asp Ile Lys Ser Thr Ile Asp Ala Ser Asn Ile Ser Cys Phe Gln Asn
            500                 505                 510

Asn Val Glu Ile His Val Ala His Ile Gln Ser Gly Leu Ser Gln Met
        515                 520                 525

Gly Asn Leu His Ala Phe Ala Ala Asn Asn Thr Asn Arg Asp
    530                 535                 540

<210> SEQ ID NO 6
<211> LENGTH: 485
<212> TYPE: PRT
<213> ORGANISM: Mus musculus

<400> SEQUENCE: 6

Met Pro Phe Arg Asn Ser Lys Arg Ser Arg Leu Phe Ser Asp Glu Asp
1               5                   10                  15

Asp Arg Gln Ile Asn Thr Lys Ser Pro Lys Arg Asn Gln Arg Val Ala
            20                  25                  30

Met Ile Pro Gln Lys Phe Thr Ala Thr Met Ser Thr Pro Asp Lys Lys
        35                  40                  45

Ala Ser Gln Lys Ile Gly Phe Arg Leu Arg Asn Leu Leu Lys Leu Pro
    50                  55                  60

Lys Ala His Lys Trp Cys Ile Tyr Glu Trp Phe Tyr Ser Asn Ile Asp
65                  70                  75                  80

Lys Pro Leu Phe Glu Gly Asp Asn Asp Phe Cys Val Cys Leu Lys Glu
                85                  90                  95

Ser Phe Pro Asn Leu Lys Thr Arg Lys Leu Thr Arg Val Glu Trp Gly
            100                 105                 110

Lys Ile Arg Arg Leu Met Gly Lys Pro Arg Arg Cys Ser Ser Ala Phe
        115                 120                 125

Phe Glu Glu Glu Arg Ser Ala Leu Lys Gln Lys Arg Gln Lys Ile Arg
    130                 135                 140

Leu Leu Gln Gln Arg Lys Val Ala Asp Val Ser Gln Phe Lys Asp Leu
145                 150                 155                 160

Pro Asp Glu Ile Pro Leu Pro Leu Val Ile Gly Thr Lys Val Thr Ala
```

-continued

```
                165                 170                 175
Arg Leu Arg Gly Ile His Asp Gly Leu Phe Thr Gly Gln Ile Asp Ala
            180                 185                 190

Val Asp Thr Leu Asn Ala Thr Tyr Arg Val Thr Phe Asp Arg Thr Gly
        195                 200                 205

Leu Gly Thr His Thr Ile Pro Asp Tyr Glu Val Leu Ser Asn Glu Pro
    210                 215                 220

His Glu Thr Met Pro Ile Ser Ala Phe Gly Gln Lys Gln Arg Pro Ser
225                 230                 235                 240

Arg Phe Phe Met Thr Pro Pro Arg Leu His Tyr Thr Pro Pro Leu Gln
                245                 250                 255

Ser Pro Ile Thr Asp Gly Asp Pro Leu Leu Gly Gln Ser Pro Trp Arg
            260                 265                 270

Ser Lys Val Ser Gly Ser Asp Thr Glu Thr Leu Gly Gly Phe Pro Val
        275                 280                 285

Glu Phe Leu Ile Gln Val Thr Lys Leu Ser Lys Ile Leu Met Ile Lys
    290                 295                 300

Lys Glu His Ile Lys Lys Leu Arg Glu Met Asn Thr Glu Ala Glu Lys
305                 310                 315                 320

Leu Lys Ser Tyr Ser Met Pro Ile Gly Ile Glu Phe Gln Arg Arg Tyr
                325                 330                 335

Ala Thr Ile Val Leu Glu Leu Glu Gln Leu Asn Lys Asp Leu Asn Lys
            340                 345                 350

Val Leu His Lys Val Gln Gln Tyr Cys Tyr Glu Leu Ala Pro Asp Gln
        355                 360                 365

Gly Leu Gln Pro Ala Asp Gln Pro Thr Asp Met Arg Arg Arg Cys Glu
    370                 375                 380

Glu Glu Ala Gln Glu Ile Val Arg Gln Ala Asn Ser Ala Ser Gly Gln
385                 390                 395                 400

Pro Cys Val Glu Asn Glu Leu Thr Asp Leu Ile Ser Arg Leu Thr
                405                 410                 415

Ala Ile Leu Leu Gln Ile Lys Cys Leu Ala Glu Gly Gly Asp Leu Asn
            420                 425                 430

Ser Phe Glu Phe Lys Ser Leu Thr Asp Ser Leu Asn Asp Ile Lys Asn
        435                 440                 445

Thr Ile Asp Ala Ser Asn Ile Ser Cys Phe Gln Asn Asn Val Glu Ile
    450                 455                 460

His Val Ala His Ile Gln Ser Gly Leu Ser Gln Met Gly Asn Leu His
465                 470                 475                 480

Ala Phe Ala Ala Asn
                485
```

<210> SEQ ID NO 7
<211> LENGTH: 15
<212> TYPE: PRT
<213> ORGANISM: Artificial
<220> FEATURE:
<223> OTHER INFORMATION: FITC-labeled protein internalization signal
      based on an 11 amino acid sequence from HIV tat protein, which is
      included as SEQ ID NO: 8.
<220> FEATURE:
<221> NAME/KEY: MISC_FEATURE
<222> LOCATION: (1)..(1)
<223> OTHER INFORMATION: FITC label

<400> SEQUENCE: 7

Gly Gly Gly Gly Tyr Gly Arg Lys Lys Arg Arg Gln Arg Arg Arg

-continued

```
1               5                   10                  15

<210> SEQ ID NO 8
<211> LENGTH: 11
<212> TYPE: PRT
<213> ORGANISM: Artificial
<220> FEATURE:
<223> OTHER INFORMATION: 11 amino acid protein internalization sequence
      signal based on the HIV tat protein.

<400> SEQUENCE: 8

Tyr Gly Arg Lys Lys Arg Arg Gln Arg Arg Arg
1               5                   10

<210> SEQ ID NO 9
<211> LENGTH: 1644
<212> TYPE: DNA
<213> ORGANISM: Mus musculus
<220> FEATURE:
<221> NAME/KEY: CDS
<222> LOCATION: (34)..(1644)

<400> SEQUENCE: 9
cagcctttga aaagcggcg cggctcgttc aag atg gcg gag ctc gac cag ttg       54
                                   Met Ala Glu Leu Asp Gln Leu
                                   1               5 cct gac gag agc tct tca gca aaa gcc ctt gtc agt tta aaa gag gga      102
Pro Asp Glu Ser Ser Ser Ala Lys Ala Leu Val Ser Leu Lys Glu Gly
            10                  15                  20 agt tta tct aac aca tgg aat gaa aag tac agt tct tta cag aaa act      150
Ser Leu Ser Asn Thr Trp Asn Glu Lys Tyr Ser Ser Leu Gln Lys Thr
        25                  30                  35 cct gtt tgg aaa ggc agg aat gcg ggc cct gct gta gaa atg cct ttc      198
Pro Val Trp Lys Gly Arg Asn Ala Gly Pro Ala Val Glu Met Pro Phe
40                  45                  50                  55 aga aat tca aaa aga agt cga ctc ttt tct gat gaa gat gac aga caa      246
Arg Asn Ser Lys Arg Ser Arg Leu Phe Ser Asp Glu Asp Asp Arg Gln
                60                  65                  70 ata aat aca aag tca cct aaa aga aac cag aga gtg gca atg atc cca      294
Ile Asn Thr Lys Ser Pro Lys Arg Asn Gln Arg Val Ala Met Ile Pro
            75                  80                  85 cag aaa ttt aca gca acg atg tca aca cca gat aag aaa gca tca cag      342
Gln Lys Phe Thr Ala Thr Met Ser Thr Pro Asp Lys Lys Ala Ser Gln
        90                  95                  100 aag att ggt ttt cga tta cgg aac cta ctc aag ctt ccc aaa gca cat      390
Lys Ile Gly Phe Arg Leu Arg Asn Leu Leu Lys Leu Pro Lys Ala His
105                 110                 115 aag tgg tgc ata tat gag tgg ttc tac tca aac ata gac aag cca ctt      438
Lys Trp Cys Ile Tyr Glu Trp Phe Tyr Ser Asn Ile Asp Lys Pro Leu
120                 125                 130                 135 ttt gaa gga gat aat gac ttt tgt gta tgc cta aag gaa tcc ttt cct      486
Phe Glu Gly Asp Asn Asp Phe Cys Val Cys Leu Lys Glu Ser Phe Pro
                140                 145                 150 aat ttg aaa aca aga aaa tta aca aga gta gaa tgg gga aaa atc agg      534
Asn Leu Lys Thr Arg Lys Leu Thr Arg Val Glu Trp Gly Lys Ile Arg
            155                 160                 165 aga ctg atg gga aaa cct cgg aga tgt tct tct gca ttt ttt gag gaa      582
Arg Leu Met Gly Lys Pro Arg Arg Cys Ser Ser Ala Phe Phe Glu Glu
        170                 175                 180 gag agg tca gcc tta aaa cag aag cgg cag aaa atc agg ctg tta caa      630
Glu Arg Ser Ala Leu Lys Gln Lys Arg Gln Lys Ile Arg Leu Leu Gln
    185                 190                 195
```

| | | | | | | | | | | | | | | |
|---|---|---|---|---|---|---|---|---|---|---|---|---|---|---|
| caa | agg | aaa | gtt | gca | gat | gtt | tca | cag | ttc | aaa | gat | ctc | ccc | gat | gaa | 678 |
| Gln | Arg | Lys | Val | Ala | Asp | Val | Ser | Gln | Phe | Lys | Asp | Leu | Pro | Asp | Glu |
| 200 | | | | 205 | | | | | 210 | | | | | 215 | |

| | | | | | | | | | | | | | | |
|---|---|---|---|---|---|---|---|---|---|---|---|---|---|---|
| atc | cct | cta | ccc | ctg | gtt | att | gga | acc | aaa | gtt | aca | gcg | cgg | tta | cgt | 726 |
| Ile | Pro | Leu | Pro | Leu | Val | Ile | Gly | Thr | Lys | Val | Thr | Ala | Arg | Leu | Arg |
| | | | 220 | | | | | 225 | | | | | 230 | | |

| | | | | | | | | | | | | | | |
|---|---|---|---|---|---|---|---|---|---|---|---|---|---|---|
| ggc | att | cac | gat | ggc | ctg | ttt | act | ggt | cag | ata | gat | gca | gtg | gac | act | 774 |
| Gly | Ile | His | Asp | Gly | Leu | Phe | Thr | Gly | Gln | Ile | Asp | Ala | Val | Asp | Thr |
| | | | 235 | | | | | 240 | | | | | 245 | | |

| | | | | | | | | | | | | | | |
|---|---|---|---|---|---|---|---|---|---|---|---|---|---|---|
| ctt | aat | gct | act | tac | aga | gta | act | ttc | gat | agg | aca | ggc | ctt | ggg | act | 822 |
| Leu | Asn | Ala | Thr | Tyr | Arg | Val | Thr | Phe | Asp | Arg | Thr | Gly | Leu | Gly | Thr |
| | 250 | | | | | 255 | | | | | 260 | | | | |

| | | | | | | | | | | | | | | |
|---|---|---|---|---|---|---|---|---|---|---|---|---|---|---|
| cac | acc | att | cct | gac | tat | gaa | gtt | ctt | agt | aat | gag | cct | cat | gag | aca | 870 |
| His | Thr | Ile | Pro | Asp | Tyr | Glu | Val | Leu | Ser | Asn | Glu | Pro | His | Glu | Thr |
| 265 | | | | | 270 | | | | | 275 | | | | | |

| | | | | | | | | | | | | | | |
|---|---|---|---|---|---|---|---|---|---|---|---|---|---|---|
| atg | cca | atc | tct | gcc | ttt | gga | caa | aaa | cag | cgg | cct | tct | cgg | ttt | ttt | 918 |
| Met | Pro | Ile | Ser | Ala | Phe | Gly | Gln | Lys | Gln | Arg | Pro | Ser | Arg | Phe | Phe |
| 280 | | | | | 285 | | | | | 290 | | | | | 295 |

| | | | | | | | | | | | | | | |
|---|---|---|---|---|---|---|---|---|---|---|---|---|---|---|
| atg | acc | ccc | cca | cgg | tta | cat | tat | acc | cct | cct | ctc | cag | tca | cca | att | 966 |
| Met | Thr | Pro | Pro | Arg | Leu | His | Tyr | Thr | Pro | Pro | Leu | Gln | Ser | Pro | Ile |
| | | | 300 | | | | | 305 | | | | | 310 | | |

| | | | | | | | | | | | | | | |
|---|---|---|---|---|---|---|---|---|---|---|---|---|---|---|
| aca | gat | ggc | gat | cct | tta | ctg | ggg | cag | tca | cct | tgg | aga | agt | aaa | gtt | 1014 |
| Thr | Asp | Gly | Asp | Pro | Leu | Leu | Gly | Gln | Ser | Pro | Trp | Arg | Ser | Lys | Val |
| | | | 315 | | | | | 320 | | | | | 325 | | |

| | | | | | | | | | | | | | | |
|---|---|---|---|---|---|---|---|---|---|---|---|---|---|---|
| tct | ggc | tct | gac | acg | gag | acg | tta | gga | ggc | ttt | cca | gtg | gaa | ttc | ctt | 1062 |
| Ser | Gly | Ser | Asp | Thr | Glu | Thr | Leu | Gly | Gly | Phe | Pro | Val | Glu | Phe | Leu |
| | | | 330 | | | | | 335 | | | | | 340 | | |

| | | | | | | | | | | | | | | |
|---|---|---|---|---|---|---|---|---|---|---|---|---|---|---|
| atc | cag | gtg | act | aag | tta | tca | aaa | att | ctc | atg | ata | aaa | aaa | gag | cat | 1110 |
| Ile | Gln | Val | Thr | Lys | Leu | Ser | Lys | Ile | Leu | Met | Ile | Lys | Lys | Glu | His |
| 345 | | | | | 350 | | | | | 355 | | | | | |

| | | | | | | | | | | | | | | |
|---|---|---|---|---|---|---|---|---|---|---|---|---|---|---|
| ata | aag | aaa | tta | agg | gag | atg | aac | aca | gaa | gca | gaa | aag | ctg | aaa | tcc | 1158 |
| Ile | Lys | Lys | Leu | Arg | Glu | Met | Asn | Thr | Glu | Ala | Glu | Lys | Leu | Lys | Ser |
| 360 | | | | | 365 | | | | | 370 | | | | | 375 |

| | | | | | | | | | | | | | | |
|---|---|---|---|---|---|---|---|---|---|---|---|---|---|---|
| tat | tcc | atg | ccc | att | ggc | att | gag | ttt | cag | cgg | aga | tac | gca | acg | atc | 1206 |
| Tyr | Ser | Met | Pro | Ile | Gly | Ile | Glu | Phe | Gln | Arg | Arg | Tyr | Ala | Thr | Ile |
| | | | 380 | | | | | 385 | | | | | 390 | | |

| | | | | | | | | | | | | | | |
|---|---|---|---|---|---|---|---|---|---|---|---|---|---|---|
| gtc | ctg | gag | ctt | gag | cag | ctg | aac | aag | gac | ctg | aac | aaa | gtt | ctg | cat | 1254 |
| Val | Leu | Glu | Leu | Glu | Gln | Leu | Asn | Lys | Asp | Leu | Asn | Lys | Val | Leu | His |
| | | | 395 | | | | | 400 | | | | | 405 | | |

| | | | | | | | | | | | | | | |
|---|---|---|---|---|---|---|---|---|---|---|---|---|---|---|
| aaa | gtt | cag | cag | tat | tgc | tat | gag | ctt | gca | cca | gac | cag | gga | ctc | cag | 1302 |
| Lys | Val | Gln | Gln | Tyr | Cys | Tyr | Glu | Leu | Ala | Pro | Asp | Gln | Gly | Leu | Gln |
| | | | 410 | | | | | 415 | | | | | 420 | | |

| | | | | | | | | | | | | | | |
|---|---|---|---|---|---|---|---|---|---|---|---|---|---|---|
| cct | gcc | gat | cag | cca | aca | gac | atg | aga | cgg | agg | tgt | gag | gaa | gaa | gcc | 1350 |
| Pro | Ala | Asp | Gln | Pro | Thr | Asp | Met | Arg | Arg | Arg | Cys | Glu | Glu | Glu | Ala |
| 425 | | | | | 430 | | | | | 435 | | | | | |

| | | | | | | | | | | | | | | |
|---|---|---|---|---|---|---|---|---|---|---|---|---|---|---|
| cag | gaa | atc | gtc | cgg | caa | gcc | aac | tct | gct | tcc | gga | cag | ccc | tgt | gta | 1398 |
| Gln | Glu | Ile | Val | Arg | Gln | Ala | Asn | Ser | Ala | Ser | Gly | Gln | Pro | Cys | Val |
| 440 | | | | | 445 | | | | | 450 | | | | | 455 |

| | | | | | | | | | | | | | | |
|---|---|---|---|---|---|---|---|---|---|---|---|---|---|---|
| gaa | aac | gaa | aat | ctg | acg | gac | ttg | atc | tcc | agg | ctc | act | gcg | att | tta | 1446 |
| Glu | Asn | Glu | Asn | Leu | Thr | Asp | Leu | Ile | Ser | Arg | Leu | Thr | Ala | Ile | Leu |
| | | | 460 | | | | | 465 | | | | | 470 | | |

| | | | | | | | | | | | | | | |
|---|---|---|---|---|---|---|---|---|---|---|---|---|---|---|
| tta | caa | att | aag | tgt | ctg | gca | gag | gga | gga | gac | ctg | aat | tcc | ttt | gaa | 1494 |
| Leu | Gln | Ile | Lys | Cys | Leu | Ala | Glu | Gly | Gly | Asp | Leu | Asn | Ser | Phe | Glu |
| | | | 475 | | | | | 480 | | | | | 485 | | |

| | | | | | | | | | | | | | | |
|---|---|---|---|---|---|---|---|---|---|---|---|---|---|---|
| ttc | aaa | tct | ctc | aca | gat | tca | tta | aat | gac | ata | aaa | aac | aca | ata | gat | 1542 |
| Phe | Lys | Ser | Leu | Thr | Asp | Ser | Leu | Asn | Asp | Ile | Lys | Asn | Thr | Ile | Asp |
| | | | 490 | | | | | 495 | | | | | 500 | | |

| | | | | | | | | | | | | | | |
|---|---|---|---|---|---|---|---|---|---|---|---|---|---|---|
| gct | tct | aat | atc | agt | tgt | ttt | cag | aat | aac | gta | gaa | atc | cat | gtt | gca | 1590 |
| Ala | Ser | Asn | Ile | Ser | Cys | Phe | Gln | Asn | Asn | Val | Glu | Ile | His | Val | Ala |
| | | | 505 | | | | | 510 | | | | | 515 | | |

```
cat atc cag agt ggc ctg agt cag atg gga aac tta cac gcc ttt gca        1638
His Ile Gln Ser Gly Leu Ser Gln Met Gly Asn Leu His Ala Phe Ala
520                 525                 530                 535 gcc aac                                                                1644
Ala Asn
```

<210> SEQ ID NO 10
<211> LENGTH: 537
<212> TYPE: PRT
<213> ORGANISM: Mus musculus

<400> SEQUENCE: 10

```
Met Ala Glu Leu Asp Gln Leu Pro Asp Glu Ser Ser Ala Lys Ala
1               5                   10                  15

Leu Val Ser Leu Lys Glu Gly Ser Leu Ser Asn Thr Trp Asn Glu Lys
                20                  25                  30

Tyr Ser Ser Leu Gln Lys Thr Pro Val Trp Lys Gly Arg Asn Ala Gly
            35                  40                  45

Pro Ala Val Glu Met Pro Phe Arg Asn Ser Lys Arg Ser Arg Leu Phe
        50                  55                  60

Ser Asp Glu Asp Asp Arg Gln Ile Asn Thr Lys Ser Pro Lys Arg Asn
65                  70                  75                  80

Gln Arg Val Ala Met Ile Pro Gln Lys Phe Thr Ala Thr Met Ser Thr
                85                  90                  95

Pro Asp Lys Lys Ala Ser Gln Lys Ile Gly Phe Arg Leu Arg Asn Leu
            100                 105                 110

Leu Lys Leu Pro Lys Ala His Lys Trp Cys Ile Tyr Glu Trp Phe Tyr
        115                 120                 125

Ser Asn Ile Asp Lys Pro Leu Phe Glu Gly Asp Asn Asp Phe Cys Val
130                 135                 140

Cys Leu Lys Glu Ser Phe Pro Asn Leu Lys Thr Arg Lys Leu Thr Arg
145                 150                 155                 160

Val Glu Trp Gly Lys Ile Arg Arg Leu Met Gly Lys Pro Arg Arg Cys
                165                 170                 175

Ser Ser Ala Phe Phe Glu Glu Glu Arg Ser Ala Leu Lys Gln Lys Arg
            180                 185                 190

Gln Lys Ile Arg Leu Leu Gln Gln Arg Lys Val Ala Asp Val Ser Gln
        195                 200                 205

Phe Lys Asp Leu Pro Asp Glu Ile Pro Leu Pro Leu Val Ile Gly Thr
    210                 215                 220

Lys Val Thr Ala Arg Leu Arg Gly Ile His Asp Gly Leu Phe Thr Gly
225                 230                 235                 240

Gln Ile Asp Ala Val Asp Thr Leu Asn Ala Thr Tyr Arg Val Thr Phe
                245                 250                 255

Asp Arg Thr Gly Leu Gly Thr His Thr Ile Pro Asp Tyr Glu Val Leu
            260                 265                 270

Ser Asn Glu Pro His Glu Thr Met Pro Ile Ser Ala Phe Gly Gln Lys
        275                 280                 285

Gln Arg Pro Ser Arg Phe Phe Met Thr Pro Arg Leu His Tyr Thr
    290                 295                 300

Pro Pro Leu Gln Ser Pro Ile Thr Asp Gly Asp Pro Leu Leu Gly Gln
305                 310                 315                 320

Ser Pro Trp Arg Ser Lys Val Ser Gly Ser Asp Thr Glu Thr Leu Gly
                325                 330                 335
```

-continued

```
Gly Phe Pro Val Glu Phe Leu Ile Gln Val Thr Lys Leu Ser Lys Ile
            340             345             350

Leu Met Ile Lys Lys Glu His Ile Lys Lys Leu Arg Glu Met Asn Thr
            355             360             365

Glu Ala Glu Lys Leu Lys Ser Tyr Ser Met Pro Ile Gly Ile Glu Phe
        370             375             380

Gln Arg Arg Tyr Ala Thr Ile Val Leu Glu Leu Glu Gln Leu Asn Lys
385             390             395                         400

Asp Leu Asn Lys Val Leu His Lys Val Gln Gln Tyr Cys Tyr Glu Leu
                405             410             415

Ala Pro Asp Gln Gly Leu Gln Pro Ala Asp Gln Pro Thr Asp Met Arg
            420             425             430

Arg Arg Cys Glu Glu Glu Ala Gln Glu Ile Val Arg Gln Ala Asn Ser
            435             440             445

Ala Ser Gly Gln Pro Cys Val Glu Asn Glu Asn Leu Thr Asp Leu Ile
        450             455             460

Ser Arg Leu Thr Ala Ile Leu Leu Gln Ile Lys Cys Leu Ala Glu Gly
465             470             475                         480

Gly Asp Leu Asn Ser Phe Glu Phe Lys Ser Leu Thr Asp Ser Leu Asn
                485             490             495

Asp Ile Lys Asn Thr Ile Asp Ala Ser Asn Ile Ser Cys Phe Gln Asn
            500             505             510

Asn Val Glu Ile His Val Ala His Ile Gln Ser Gly Leu Ser Gln Met
        515             520             525

Gly Asn Leu His Ala Phe Ala Ala Asn
530             535
```